US010945984B2

(12) United States Patent
Cundy et al.

(10) Patent No.: US 10,945,984 B2
(45) Date of Patent: *Mar. 16, 2021

(54) METHODS OF ADMINISTERING MONOMETHYL FUMARATE AND PRODRUGS THEREOF HAVING REDUCED SIDE EFFECTS

(71) Applicant: Arbor Pharmaceuticals, LLC, Atlanta, GA (US)

(72) Inventors: Kenneth C. Cundy, Redwood City, CA (US); Sami Karaborni, Cupertino, CA (US); Peter A. Virsik, Portola Valley, CA (US)

(73) Assignee: Arbor Pharmaceuticals, LLC, Atlanta, GA (US)

( * ) Notice: Subject to any disclaimer, the term of this patent is extended or adjusted under 35 U.S.C. 154(b) by 427 days.

This patent is subject to a terminal disclaimer.

(21) Appl. No.: 13/973,700

(22) Filed: Aug. 22, 2013

(65) Prior Publication Data

US 2014/0057917 A1 Feb. 27, 2014
US 2014/0350018 A9 Nov. 27, 2014

Related U.S. Application Data

(60) Provisional application No. 61/841,513, filed on Jul. 1, 2013, provisional application No. 61/837,796, filed on Jun. 21, 2013, provisional application No. 61/800,132, filed on Mar. 15, 2013, provisional application No. 61/769,513, filed on Feb. 26, 2013, provisional application No. 61/733,234, filed on Dec. 4, 2012, provisional application No. 61/713,897, filed on Oct. 15, 2012, provisional application No. 61/713,961, filed on Oct. 15, 2012, provisional application No. 61/692,174, filed on Aug. 22, 2012, provisional application No. 61/692,168, filed on Aug. 22, 2012.

(51) Int. Cl.

| A61K 31/535 | (2006.01) |
|---|---|
| A61K 47/00 | (2006.01) |
| A61K 31/225 | (2006.01) |
| A61K 9/28 | (2006.01) |
| A61K 31/5375 | (2006.01) |

(52) U.S. Cl.
CPC .......... *A61K 31/225* (2013.01); *A61K 9/2846* (2013.01); *A61K 9/2866* (2013.01); *A61K 9/2886* (2013.01); *A61K 31/5375* (2013.01)

(58) Field of Classification Search
CPC .............. A61K 31/225; A61K 31/5375; A61K 9/2866; A16K 9/2886
See application file for complete search history.

(56) References Cited

U.S. PATENT DOCUMENTS

| 3,139,395 A | 6/1964 | Griffin |
|---|---|---|
| 3,336,364 A | 8/1967 | Dill |
| 4,851,439 A | 7/1989 | Speiser et al. |
| 4,863,916 A | 9/1989 | Habich et al. |
| 4,919,938 A * | 4/1990 | Lovegrove ........... A61K 9/2013 424/473 |
| 4,959,389 A | 9/1990 | Speiser et al. |
| 5,073,641 A | 12/1991 | Bundgaard et al. |
| 5,145,684 A | 9/1992 | Liversidge et al. |
| 5,149,695 A | 9/1992 | Speiser et al. |
| 5,424,332 A | 6/1995 | Speiser et al. |
| 5,451,667 A | 9/1995 | Speiser et al. |
| 5,534,250 A | 7/1996 | Klaveness et al. |
| 6,130,248 A | 10/2000 | Nudelman et al. |
| 6,277,882 B1 | 8/2001 | Joshi et al. |
| 6,359,003 B1 | 3/2002 | Joshi et al. |
| 6,355,676 B1 | 4/2002 | Joshi et al. |
| 6,379,697 B1 | 4/2002 | Gregoriadis et al. |
| 6,436,992 B1 | 8/2002 | Joshi et al. |
| 6,509,376 B1 | 1/2003 | Joshi et al. |
| 6,613,800 B1 | 9/2003 | Smith |
| 6,709,868 B2 | 3/2004 | Law et al. |
| 6,723,508 B2 | 4/2004 | Sprenger et al. |
| 6,858,750 B2 | 2/2005 | Joshi et al. |
| 7,157,423 B2 | 1/2007 | Joshi et al. |
| 7,320,999 B2 | 1/2008 | Joshi et al. |
| 7,432,240 B2 | 10/2008 | Joshi et al. |
| 7,612,110 B2 | 11/2009 | Joshi et al. |
| 7,619,001 B2 | 11/2009 | Joshi et al. |
| 7,638,118 B2 | 12/2009 | Flachsmann et al. |
| 7,790,916 B2 | 9/2010 | Joshi et al. |
| 7,803,840 B2 | 9/2010 | Joshi et al. |
| 7,906,659 B2 | 3/2011 | Joshi et al. |
| 7,915,310 B2 | 3/2011 | Joshi et al. |
| 8,067,467 B2 | 11/2011 | Joshi et al. |

(Continued)

FOREIGN PATENT DOCUMENTS

| CN | 1616400 | 5/2005 |
|---|---|---|
| CN | 101318901 | 12/2008 |

(Continued)

OTHER PUBLICATIONS

Carter, et al., Chemotherapy of Cancer, 2nd ed., 1981, pp. 362-365.*
U.S. Appl. No. 12/544,133, filed Aug. 19, 2009, Gangakhedkar et al.
U.S. Appl. No. 13/274,282, filed Oct. 14, 2011, Gangakhedkar et al.
U.S. Appl. No. 13/274,284, filed Oct. 14, 2011, Gangakhedkar et al.
U.S. Appl. No. 14/298,668, filed Jun. 6, 2014, Gangakhedkar et al.
U.S. Appl. No. 13/761,864, filed Feb. 7, 2013, Cundy et al.
U.S. Appl. No. 13/967,283, filed Aug. 14, 2013, Cundy et al.
U.S. Appl. No. 14/072,138, filed Nov. 5, 2013, Mao et al.
U.S. Appl. No. 13/906,155, filed May 30, 2013, Virsik et al.
U.S. Appl. No. 14/661,698, filed Mar. 18, 2015, Cundy.
U.S. Appl. No. 14/223,026, filed Mar. 24, 2014, Karaborni et al.

(Continued)

*Primary Examiner* — Shobha Kantamneni
(74) *Attorney, Agent, or Firm* — King & Spalding

(57) ABSTRACT

Methods of reducing undesirable side effects during therapeutic treatment using monomethyl fumarate and prodrugs of monomethyl fumarate are disclosed.

12 Claims, 16 Drawing Sheets

(56) References Cited

U.S. PATENT DOCUMENTS

| | | |
|---|---|---|
| 8,148,414 B2 | 4/2012 | Gangakhedkar et al. |
| 8,399,514 B2 | 3/2013 | Lukashev et al. |
| 8,524,773 B2 | 9/2013 | Joshi et al. |
| 8,669,281 B1 | 3/2014 | Zeidan et al. |
| 8,759,393 B2 | 6/2014 | Joshi et al. |
| 8,778,991 B2 | 7/2014 | Gangakhedkar et al. |
| 8,785,443 B2 | 7/2014 | Gangakhedkar et al. |
| 8,906,420 B2 | 12/2014 | Nilsson et al. |
| 8,952,006 B2 | 2/2015 | Cundy et al. |
| 2003/0018072 A1 | 1/2003 | Joshi et al. |
| 2004/0054001 A1 | 3/2004 | Joshi et al. |
| 2004/0102525 A1 | 5/2004 | Kozachuk |
| 2005/0095292 A1 | 5/2005 | Benjamin et al. |
| 2005/0096369 A1 | 5/2005 | Hoang |
| 2005/0101779 A1 | 5/2005 | Sagi et al. |
| 2005/0148664 A1 | 7/2005 | Joshi et al. |
| 2005/0208133 A1 | 9/2005 | Tsutsumi et al. |
| 2006/0205659 A1 | 9/2006 | Joshi et al. |
| 2006/0269925 A1 | 11/2006 | Nunes et al. |
| 2007/0027076 A1 | 2/2007 | Joshi et al. |
| 2007/0021330 A1 | 9/2007 | Liu et al. |
| 2007/0231382 A1 | 10/2007 | Karnachi et al. |
| 2007/0248663 A1 | 10/2007 | Joshi et al. |
| 2007/0253902 A1 | 11/2007 | Lobb et al. |
| 2008/0004344 A1 | 1/2008 | Nilsson et al. |
| 2008/0033199 A1 | 2/2008 | Lai et al. |
| 2008/0089861 A1 | 4/2008 | Went et al. |
| 2008/0089896 A1 | 4/2008 | Wang et al. |
| 2008/0227847 A1 | 9/2008 | Nilsson et al. |
| 2008/0233185 A1 | 9/2008 | Joshi et al. |
| 2008/0299196 A1 | 12/2008 | Nilsson et al. |
| 2008/0300217 A1 | 12/2008 | Nilsson |
| 2009/0011986 A1 | 1/2009 | Joshi et al. |
| 2009/0181085 A1 | 7/2009 | Joshi et al. |
| 2009/0182047 A1 | 7/2009 | Joshi et al. |
| 2009/0304790 A1 | 12/2009 | Nilsson et al. |
| 2010/0048651 A1 | 2/2010 | Gangakhedkar et al. |
| 2010/0099907 A1 | 4/2010 | Raillard et al. |
| 2010/0105784 A1 | 4/2010 | Remon et al. |
| 2010/0130607 A1 | 5/2010 | Gold |
| 2010/0144651 A1 | 6/2010 | Nilsson et al. |
| 2010/0226981 A1 | 9/2010 | Karaborni et al. |
| 2010/0247642 A1 | 9/2010 | Wu et al. |
| 2010/0260755 A1 | 10/2010 | Gammans et al. |
| 2011/0112196 A1 | 5/2011 | Lukashev |
| 2011/0124615 A1 | 5/2011 | Joshi et al. |
| 2011/0212169 A1 | 9/2011 | Bae et al. |
| 2011/0293711 A1 | 12/2011 | Joshi et al. |
| 2012/0034274 A1 | 2/2012 | Nilsson et al. |
| 2012/0034303 A1 | 2/2012 | Nilsson et al. |
| 2012/0095003 A1 | 4/2012 | Gangakhedkar et al. |
| 2012/0157523 A1 | 6/2012 | Gangakhedkar et al. |
| 2012/0165404 A1 | 6/2012 | Lukashev |
| 2013/0065909 A1 | 3/2013 | Milne et al. |
| 2013/0172391 A1 | 7/2013 | Kahrs |
| 2013/0203753 A1 | 8/2013 | Cundy et al. |
| 2013/0259856 A1 | 10/2013 | Kaye |
| 2013/0259906 A1 | 10/2013 | Joshi et al. |
| 2013/0295169 A1 | 11/2013 | Goldman et al. |
| 2013/0302410 A1 | 11/2013 | Gold |
| 2013/0317103 A1 | 11/2013 | Lukashev |
| 2013/0324539 A1 | 12/2013 | Virsik et al. |
| 2014/0051705 A1 | 2/2014 | Cundy et al. |
| 2014/0056973 A1 | 2/2014 | Ma et al. |
| 2014/0056978 A1 | 2/2014 | Karaborni et al. |
| 2014/0057918 A1 | 2/2014 | Wustrow et al. |
| 2014/0065211 A1 | 3/2014 | Karaborni et al. |
| 2014/0066505 A1 | 3/2014 | Joshi et al. |
| 2014/0099364 A2 | 4/2014 | Nilsson et al. |
| 2014/0163100 A1 | 6/2014 | Dawson et al. |
| 2014/0179778 A1 | 6/2014 | Mao et al. |
| 2014/0179779 A1 | 6/2014 | Chao |
| 2014/0193386 A1 | 7/2014 | Preiss-Bloom et al. |
| 2014/0193387 A1 | 7/2014 | Gruskin et al. |
| 2014/0193388 A1 | 7/2014 | Velders et al. |
| 2014/0193390 A1 | 7/2014 | Valenzano et al. |
| 2014/0193392 A1 | 7/2014 | Annunziata et al. |
| 2014/0193393 A1 | 7/2014 | Gulati |
| 2014/0193495 A1 | 7/2014 | Nilsson |
| 2014/0194427 A1 | 7/2014 | Chao |
| 2014/0200272 A1 | 7/2014 | Nilsson et al. |
| 2014/0200273 A1 | 7/2014 | Nilsson et al. |
| 2014/0200363 A1 | 7/2014 | Guzowski et al. |
| 2014/0205659 A1 | 7/2014 | Nilsson et al. |
| 2014/0275048 A1 | 9/2014 | Zeidan et al. |
| 2014/0275250 A1 | 9/2014 | Cundy et al. |
| 2014/0284245 A1 | 9/2014 | Karaborni et al. |
| 2014/0323570 A1 | 10/2014 | Gold |
| 2014/0329818 A1 | 11/2014 | Gangakhedkar et al. |
| 2014/0336151 A1 | 11/2014 | Chao |
| 2014/0364604 A1 | 12/2014 | Raillard et al. |
| 2014/0378542 A1 | 12/2014 | Mao et al. |
| 2015/0038499 A1 | 2/2015 | Virsik |
| 2015/0073049 A1 | 3/2015 | Mao et al. |
| 2015/0079180 A1 | 3/2015 | Karaborni et al. |
| 2015/0190360 A1 | 7/2015 | Cundy |

FOREIGN PATENT DOCUMENTS

| | | |
|---|---|---|
| CN | 101774913 A | 7/2010 |
| DE | 1165586 | 3/1964 |
| DE | 10360869 A1 | 4/2005 |
| EP | 2692344 A1 | 2/2014 |
| GB | 1153927 A | 6/1969 |
| GB | 1404989 A | 9/1975 |
| GB | 2285805 A | 7/1995 |
| JP | S60181047 | 9/1985 |
| JP | H03294245 | 12/1991 |
| JP | 2001158760 | 6/2001 |
| JP | 2002-027998 A | 1/2002 |
| PL | 153592 | 10/1991 |
| WO | WO 1996/036613 | 11/1996 |
| WO | WO 1998/029114 | 7/1998 |
| WO | WO 1998/052549 | 11/1998 |
| WO | WO 1998/053803 | 12/1998 |
| WO | WO99/21559 | 5/1999 |
| WO | WO 1999/049858 | 10/1999 |
| WO | WO 1999/051191 | 10/1999 |
| WO | WO 1999/062973 | 12/1999 |
| WO | WO 2000/010560 | 3/2000 |
| WO | WO 2000/012072 | 3/2000 |
| WO | WO 2002/055063 | 7/2002 |
| WO | WO 2002/055066 | 7/2002 |
| WO | WO 2002/055067 | 7/2002 |
| WO | WO 2003/087174 | 10/2003 |
| WO | WO 2005/023241 | 3/2005 |
| WO | WO 2005/027899 | 3/2005 |
| WO | WO 2006/037342 | 4/2006 |
| WO | WO 2006/050730 | 5/2006 |
| WO | WO 2006/122652 | 11/2006 |
| WO | WO 2007/006307 | 1/2007 |
| WO | WO 2007/006308 | 1/2007 |
| WO | WO 2007/042034 | 4/2007 |
| WO | WO 2007/042035 | 4/2007 |
| WO | WO 2008/096271 | 8/2008 |
| WO | WO 2008/097596 | 8/2008 |
| WO | WO 2010/022177 | 2/2010 |
| WO | WO 2010/079221 | 7/2010 |
| WO | WO 2010/079222 | 7/2010 |
| WO | WO 2010/126605 | 11/2010 |
| WO | WO 2011/080344 | 7/2011 |
| WO | WO 2011/100589 | 8/2011 |
| WO | WO 2012/162669 | 11/2012 |
| WO | WO 2012/170923 | 12/2012 |
| WO | WO 2013/022882 | 2/2013 |
| WO | WO 2013/076216 | 5/2013 |
| WO | WO 2013/119677 | 8/2013 |
| WO | WO 2013/119791 | 8/2013 |
| WO | WO 2014/020156 | 2/2014 |
| WO | WO 2014/031894 | 2/2014 |
| WO | WO 2014/031897 | 2/2014 |
| WO | WO 2014/071371 | 5/2014 |
| WO | WO 2014/096425 | 6/2014 |
| WO | WO 2014/100728 | 6/2014 |

(56) References Cited

FOREIGN PATENT DOCUMENTS

| WO | WO 2014/190056 | 11/2014 |
|---|---|---|
| WO | WO 2015/028472 | 3/2015 |
| WO | WO 2015/028473 | 3/2015 |

OTHER PUBLICATIONS

U.S. Appl. No. 14/311,020, filed Jun. 20, 2014, Mao et al.
U.S. Appl. No. 14/478,627, filed Sep. 5, 2014, Mao et al.
U.S. Appl. No. 14/298,713, filed Jun. 6, 2014, Raillard et al.
U.S. Appl. No. 14/449,513, filed Aug. 1, 2014, Virsik.
U.S. Appl. No. 14/663,649, filed Mar. 20, 2015, Manthati et al.
U.S. Appl. No. 14/490,277, filed Sep. 18, 2014, Karaborni et al.
Altmeyer et al., Antipsoriatic effect of fumaric acid derivatives, J. Amer. Acad. Derm. (1994), 30(6): 977-981.
Ashe, Learning and memory in transgenic mice modeling Alzheimer's disease. Learning & Memory (2001), 8, 301-308.
Atreya et al., NF-κB in inflammatory bowel disease. J Intern Med (2008), 263, 591-596.
Author Unknown, BG 00012, BG 12/oral fumarate, FAG-201, second-generation fumarate derivative—Fumapharm/Biogen Idec, Drugs RD (2005), 6(4): 229-230.
Bardgett et al., NMDA receptor blockade and hippocampal neuronal loss impair fear conditioning and position habit reversal in C57B1/6 mice. Brain Res Bull (2003), 60, 131-142.
Barnes, Mediators of chronic obstructive pulmonary disease. Pharmacological Reviews (2004), 56(4), 515-548.
Behari et al., Baseline characteristics of a subpopulation of Indian patients enrolled in two phase 3 trials for oral BG-12 in relapsing-remitting multiple sclerosis, 62nd Ann Mtg. Amer. Acad. Neurol. (2010), poster, 2 pages.
Bhagavathula et al., 7-Chloro-5-(4-hydroxyphenyl)-1-methyl-3-(naphthalen-2-ylmethyl)-4,5-dihydro-1H-benzo[b][1,4]diazepin-2(3H)-one (Bz-423), a benzodiazepine, suppresses keratinocyte proliferation and has antipsoriatic activity in the human skin-severe, combined immunodeficient mouse transplant model. J Pharmacol Expt'l Therapeutics (2008), 324(3), 938-947.
Blad, et al., "Biological and Pharmacological Roles of HCA Receptors", Advances in Pharmacology, 2011, 62: 219-250.
D10* Blandini, et al., Glutamate and Parkinson's disease. Mol. Neurobiol. (1996), 12(1), 73-94.
Brewer, et al., "Fumaric acid esters in the management of severe psoriasis", Clinical Experimental Dermatology, 2007, 32: 246-249.
Bundgaard et al., Esters of N,N-Disubstituted 2-Hydroxyacetamides as a Novel Highly Biolabile Prodrug Type for Carboxylic Acid Agents, J. Med. Chem. (1987), 30(3): 451-454.
Bundgaard et al., Glycolamide esters as a novel biolabile prodrug type for non-steroidal anti-inflammatory carboxylic acid drugs, Int. J. Pharm. (1988) 43: 101-110.
Capello, et al., "Marburg type and Balo's concentric sclerosis: Rare and acute variants of multiple sclerosis", Neurological Sciences 200411 IT, vol. 25, No. Suppl. 4, Nov. 2004, pp. S361-S363.
Cavarra et al., Effects of cigarette smoke in mice with different levels of α1-proteinase inhibitor and sensitivity to oxidants. Am J Respir Crit Care Med (2001), 164, 886-890.
Champion, et al., "Flushing and Flushing Syndromes, Rosacea and Perioral Dermatitis", Rook Wilkinson Ebling Textbook of Dermatology, 6th ed. vol. 3, Oxford, UK: Blackwell Scientific, 1998, pp. 2099-2104.
Cockcroft et al., Bronchial reactivity to inhaled histamine: a method and clinical survey. Clin Allergy (1977), 7, 235-243.
Cross, et al. Dimethyl Fumarate, an Immune Modulator and Inducer of the Antioxidant Response, Suppresses HIV Replication and Macrophage-Mediated Neurotoxicity: A Novel Candidate for HIV Neuroprotection. The Journal of Immunology, (2011), 187(10): 5015-5025.
D'Acquisto et al., Inhibition of nuclear factor kappa B (NF-κB): an emerging theme in anti-inflammatory therapies. Molecular Interventions (2002), 2(1), 22-35.

Dawson et al., "Bioequivalence of BG-12 (Dimethyl Fumarate) Administered as a Single 240 mg Capsule and Two 120 mg Capsules: Findings from a Randomized, Two-period Crossover Study", Poster P913 presented at the 28th Congress of the European Committee for Treatment and Research in Multiple Sclerosis, Oct. 10-13, 2012, Lyon France, 1 page.
De Jong et al., Selective stimulation of T helper 2 cytokine responses by the anti-psoriasis agent monomethylfunarate, Eur. J. Immunol. (1996), 26: 2067-2074.
Dibbert, et al.,: "Detection of fumarate-glutathione adducts in the portal vein blood of rats: Evidence for rapid dimethyl fumarate metabolism", Archives of Dermatological Research 2013 Springer Verlag Deu, vol. 305, No. 5, Jul. 2013 (Jul. 2013), pp. 447-451.
Dymicky, Preparation of Monomethyl Fumarate, Organic Preparations and Procedures International, vol. 15 No. 4 (1983), pp. 233-238.
Eberle, et al. Fumaric Acid Esters in Severe Ulcerative Necrobiosis Lipoidica: A Case Report and Evaluation of Current Therapies. Acta Dermato-Venereologica (2010) 90(1): 104-106.
Ellrichmann et al., Efficacy of fumaric acid esters in the R6/2 and YAC128 models of Huntington's disease, PLOS One (2011), 6(1): 11 pages.
Eugster et al., Superantigen overcomes resistance of IL-6 deficient mice towards MOG-induced EAE by a TNFR1 controlled pathway. Eur J Immunol (2001), 31, 2302-2312.
European Commission Health & Consumer Protection Directorate-General, Report of the scientific committee on animal nutrition on the safety of fumaric acid, adopted Jan. 22, 2003: 18 pages.
Feinstein et al., Anti-inflammatory and prometabolic effects of BG-12 in glial cells, 26th Congress Eur. Cmtee. Treat. Res. Mult. Scler. (2010), poster: 1 page.
Fox et al., Baseline characteristics of patients in a randomized, multicenter, placebo-controlled and active comparator trial evaluating efficacy and safety of BG-12 in relapsing-remitting multiple sclerosis: the CONFIRM trial, 62nd Ann Mtg. Amer. Acad. Neurol. (2010), poster, 2 pages.
Fox et al., Placebo-controlled phase 3 study of oral BG-12 or glatiramer in multiple sclerosis, N Engl J Med. Sep. 20, 2012;367(12):1087-97. Erratum in: N Engl J Med. Oct. 25, 2012;367(17):1673.
Frycak et al., Evidence of covalent interaction of fumaric acid esters with sulfhydryl groups in peptides, J. Mass. Spectrom. (2005), 40: 1309-1318.
Gadad et al., Synthesis, spectral studies and anti-inflammatory activity of glycolamide esters of niflumic acid as potential prodrugs, Arzneim Forsch Drug Res. (2002), 52(11): 817-821.
Gambichler, et al. Clearance of Necrobiosis lipoidica with Fumaric Acid Esters. Dermatology (2003), 207(4): 422-424.
Gesser et al., Dimethylfumarate specifically inhibits the mitogen and stress-activated kinases 1 and 2 (MSK1/2): Possible role for its anti-psoriatic effect. J Investigative Dermatology (2007), 127, 2129-2137.
Goke et al., Effect of a Specific Serine Protease Inhibitor on the Rat Pancreas: Systemic Administration of Camostate and Exocrine Pancreatic Secretion, Digestion (1984) 30: 171-178.
Gogas et al., Comparison of the efficacy and tolerability of a novel methyl hydrogen fumarate prodrug with dimethyl fumarate in rodent EAE and GI irritation models, XenoPort, Inc.; 26th Congress of the European Committee for Treatment and Research in Multiple Sclerosis (ECTRIMS), 2010 (Poster #671), 1 page.
Gold et al., Baseline characteristics of patients in the DEFINE trial: a randomized, multicenter, double blind, placebo-controlled, phase 3 study of BG-12 in relapsing-remitting multiple sclerosis, 62nd Ann Mtg. Amer. Acad. Neurol. (2010), poster, 2 pages.
Gold et al., Placebo-controlled phase 3 study of oral BG-12 for relapsing multiple sclerosis, N Engl J Med. Sep. 20, 2012;367(12):1098-107, Erratum in: N Engl J Med. Dec. 13, 2012;367(24):2362.
Ghoreschi Kamran, et al., "Furmarates improve psoriasis and multiple sclerosis by inducing type II dendritic cells", The Journal of Experimental Medicine, Rockefeller University Press, US, vol. 208, No. 11, Oct. 24, 2011 (Oct. 24, 2011), pp. 2291-2303.

(56) References Cited

OTHER PUBLICATIONS

Grigorian et al., Control of T-cell mediated autoimmunity by metabolite flux to N-glycan biosynthesis, J. Bio. Chem. (2007), 282(27): 20027-20035.
Guenther, et al., Macular Exanthema Due to Fumaric Acid Esters. Annals of Pharmacotherapy (2003), 37(2): 234-236.
Gurney et al., Motor neuron degeneration in mice that express a human Cu,Zn superoxide dismutase mutation. Science (1994), 264, 1772-1775.
Hanson et al., Nicotinic acid- and monomethyl funarate-induced flushing involves GPR109A expressed by keratinocytes and COX-2-dependent prostanoid formation in mice, J. Clin. Invest. (2010), 120(8): 2910-2919.
Heiligenhaus, et al. Influence of dimethylfumarate on experimental HSV-1 necrotizing keratitis. Graefe's Archive for Clinical and Experimental Ophthalmology (2004), 242(10): 870-877.
Heiligenhaus, et al. Improvement of herpetic stromal keratitis with fumaric acid derivate is associated with systemic induction of T helper 2 cytokines. Clinical and Experimental Immunology (2011), 142(1): 180-187.
Hiraku et al., Absorption and Excretion of Camostat Orally Administered to Male Rabbit and Healthy Subject, Iyakuhin Kenkyu (1982) 13(3): 756-765.
Hoefnagel, et al., "Long-term safety aspects of systemic therapy with fumaric acid esters in severe psoriasis", British Journal of Dermatology, 2003, 149: 363-369.
Horig et al., From bench to clinic and back: Perspective on the 1st IQPC Translational Research Conference, J. Transl. Med. (2004), 2(44), 8 pages.
Hoxtermann et al., Fumaric acid esters suppress peripheral CD4- and CD8-positive lymphocytes in psoriasis, Dermatology (1998), 196: 223-230.
Hurd et al., Vinylation and the Formation of Acylals:, J. Am. Chem. Soc.; vol. 78; Jan. 5, 1956; pp. 104-106.
Iyer et al., Synthesis of iodoalkylacylates and their use in the preparation of S-alkyl phosphorothiolates. Synth Commun (1995), 25(18), 2739-2749.
Jennings, Squamous cell carcinoma as a complication of fumaric acid ester immunosuppression, J. Eur. Acad. Dermatol. Venereol. (2009), DOI: 10.1111/j.1468-3083.2009.03234.x, 1 page.
Jurjus et al., Animal models of inflammatory bowel disease. J Pharmacol Toxicol Methods (2004), 50, 81-92.
Kappos et al., Efficacy and safety of oral fumarate in patients relapsing-remitting multiple sclerosis: a multicentre, randomised, double-blind, placebo controlled phase IIb study, Lancet (2008), 372: 1463-1472.
Kamimura et al., "Stereoselective formation of optically active 2-oxy-1,3-oxazolidin-4-ones from chiral O-acylmandelamides or lactamides", Tetrahedron 58, 2002, 8763-8770.
Khan et al., Synthesis and biological evaluation of glycolamide esters as potential prodrugs of some non-steroidal anti-inflammatory drugs, Ind. J. Chem. (2002) 41B: 2172-2175.
Klein, et al. Off-label use of fumarate therapy for granulomatous and inflammatory skin diseases other than psoriasis vulgaris: a retrospective study. (2012), Journal of the European Academy of Dermatology and venereology (2012), 26(11): 1400-1406 (also on-line ref: Klein, et al., (2011), J Eur Acad Dermatol Venereol doi: 10.1111/j.1468-3083.2011.04303.x).
Kreuter et al., Fumaric acid esters in necrobiosis lipoidica: results of a prospective noncontrolled study. British Journal of Dermatology (2005) 153(4): 802-807.
Lee et al., Spotlight on fumarates, Int. MS J. (2008), 15: 12-18.
Lehmann et al., Fumaric acid esters are potent immunosuppressants: inhibition of acute and chronic rejection in rat kidney transplantation models by methyl hydrogen fumarate. Arch Dermatol Res (2002), 294, 399-404.
Lehmann et al., Dimethylfumarate induces immunosuppression via glutathione depletion and subsequent induction of heme oxygenase 1. J Investigative Dermatology (2007), 127, 835-845.
Linker et al., Identification and development of new therapeutics for multiple sclerosis, Treds. Pharm. Sci. (2008), DOI 10.1016/j.tips.2008.07.012, 8 pages.
Linker et al., Fumaric acid esters exert neuroprotective effects in neuroinflammation via activation of the Nrf2 antioxidant pathway, Brain (2011), 134: 678-692.
Litjens e al., Monomethylfumarate affects polarization of monocyte-derived dendritic cells resulting in down-regulated Th1 lymphocyte responses, Eur. J. Immunol. (2004), 34: 565-575.
Litjens et al., Pharmacokinetics of oral fumarates in healthy subjects, Br. J. Clin. Pharmacol. (2004), 58(4): 429-432.
Litjens et al., Effects of monomethylfumarate on dendritic cell differentiation, Br. J. Dermatol. (2006), 154: 211-217.
Loewe et al., Dimethylfumarate inhibits TNF-induced nuclear entry of NF-κB/p65 in human endothelial cells. J Immunology (2002), 168, 4781-4787.
Loewe et al., Dimethylfumarate impairs melanoma growth in metastasis, Cancer Res. (2006), 66(24): 11888-11896.
Lopez-Diego et al., Novel therapeutic strategies for multiple sclerosis—a multifaceted adversary, Nat. Review. Drug Disc. (2008), 7:909-925.
Lukashev et al., Activation of Nrf2 and modulation of disease by BG00012 (dimethyl fumarate) suggest a dual cytoprotective and anti-inflammatory mechanism of action, 62nd Ann Mtg. Amer. Acad. Neurol. (2010), poster, 4 pages.
Mandhane, et al., Adenosine A2 receptors modulate haloperidol-induced catalepsy in rats. Eur. J. Pharmacol (1997), 328, 135-141.
Martin, Molecular basis of the neurodegenerative disorders. N Engl J Med (1999), 340(25), 1970-1980.
Martorana et al., Roflumilast fully prevents emphysema in mice chronically exposed to cigarette smoke. Am J Respir Crit Care Med (2005), 172, 848-853.
Menter et al., Guidelines of care for the management of psoriasis and psoriatic arthritis, J. Am. Acad. Dermatol. (2009), doi:10.1016/j.jaad.2009.03.027, 35 pages.
Milo, et al., "Combination therapy in multiple sclerosis", Journal of Neuroimmunology, vol. 231, No. 1, 2011, pp. 23-31.
Mosmann et al., TH1 and TH2 cells: different patterns of lymphokine secretion lead to different functional properties, Ann. Rev. Immunol. (1989), 7: 145-73.
Mrowietz, et al., "Dimethylfumarate for psoriasis: more than a dietary curiosity", Trends in Molecular Medicine, vol. 11, No. 1, Jan. 2005, pp. 43-48.
Mrowietz, et al., "Treatment of Psoriasis with Fumaric Acid Esters: Results of a prospective Multicenter Study", British Journal of Dermatology, 1998, 138: 456-460.
Mrowietz et al., Treatment of severe psoriasis with fumaric acid esters: scientific background and guidelines for therapeutic use. Br J Dermatology (1999), 141, 424-429.
Mrowietz et al., Treatment of psoriasis with fumaric acid esters (Fumaderm®), JDDG (2007), DOI: 10.1111/j.1610-0387.2007.06346.x, 2 pages.
Murakami et al., Suppression of a dextran sodium sulfate-induced colitis in mice by zerumbone, a subtropical ginger sesquiterpene, and nimesulide: separately and in combination. Biochemical Pharmacol (2003), 66, 1253-1261.
Naldi et al., Psoriasis (chronic plaque), Clin. Evid. (2009), 1(1706): 50 pages.
Nelson, et al., Effect of Dietary Inducer Dimethylfumarate on Glutathione in Cultured Human Retinal Pigment Epithelial Cells. Investigative Ophthalmology and Visual Science (1999), 40(9): 1927-1935.
Neymotin et al., Neuroprotective effect of Nrf2/AFE activators, CDDO ethylamide and CDDO trifluoroethylamide, in a mouse model of amyotrophic lateral sclerosis, Free Rad. Bio. Med (2011), 51: 88-96.
Nibbering et al., Intracellular signalling by binding sites for the antipsoriatic agent monomethylfumarate on human granulocytes, Br. J. Dermatol. (1997), 137: 65-75.
Nielsen, et al., "Glycolamide Esters as Biolabile Prodrugs of Carboxylic Acid Agents: Synthesis, Stability, Bioconversion, and Physicochemical Properties", Journal of Pharmaceutical Sciences, vol. 77, No. 4, Apr. 1988, pp. 285-298.

(56) References Cited

OTHER PUBLICATIONS

Offermans, The nicotinic acid receptor GPR109A (HM74A or PUMA-G) as a new therapeutic agent, Trends Pharm. Sci. (2006), 27(7): 384-390.

O'Toole, et al., Treatment of Carcinoid Syndrome: A Prospective Crossover Evaluation of Lanreotide versus Octreotide in Terms of Efficacy, Patient Acceptability, and Tolerance, American Cancer Society, Feb. 15, 2000, 88(4), 770-776.

Peeters et al., Fumaric acid therapy for psoriatic arthritis. A randomized, double-blind, placebo-controlled study, Br. J. Rheumatol. (1992), 31(7): 502-504.

Rantanen, The cause of the Chinese sofa/chair dermatitis epidemic is likely to be contact allergy to dimethylfumarate, a novel potent contact sensitizer, Br. J. Dermatol. (2008), 159: 218-221.

Reddingius, Bioanalysis and pharmacokinetics of fumarates in humans, Ph.D. dissertation ETH No. 12199, Swiss Fed. Inst. Tech. Zurich (1997), 82 pages.

Reich et al., Efficacy and safety of fumaric acid esters in the long-term treatment of psoriasis—a retrospective study (FUTURE), JDDG (2009), DOI: 10.1111/j.1610-0387.2009.07120.x, 8 pages.

Richman et al., Nicotinic acid receptor agonists differentially activate downstream effectors, J. Bio. Chem. (2007), 282(25): 18028-18036.

Roll et al., Use of fumaric acid esters in psoriasis, Indian J. Dermatol. Ven. Lep. (2007), 73: 133-137.

Rostami-Yazdi, et al., "Detection of Metabolites of Fumaric Acid Esters in Human Urine: Implications for their mode of action", Journal of Investigative Dermatology, 2008, pp. 1-3.

Rostami-Yazdi et al., Pharmacokinetics of antipsoriatic fumaric acid esters in psoriasis patients, Arch. Dermatol. Res. (2010), 302: 531-538.

Rowland et al., Amyotrophic lateral sclerosis. N Engl J Med (2001), 344(22), 1688-1700.

Rubant et al., Dimethylfumarate reduces leukocyte rolling in vivo through modulation of adhesion molecule expression, J. Invest. Dermatol. (2007), 128: 326-331.

Schafer et al., "Failure is an option: learning from unsuccessful proof-of-concept trials", Drug Discovery Today, vol. 13, Nos. 21/22; Nov. 2008; pp. 913-916.

Schilling, et al., "Fumaric acid esters are effective in chronic experimental autoimmune encephalomyelitis and suppress macrophage infiltration", Clinical and Experimental Immunology, 2006, 145: pp. 101-107.

Schmidt, et al., "Reactivity of dimethyl fumarate and methylhydrogen fumarate towards glutathione and N-acetyl-1-cysteine-Preparation of S-substituted thiosuccinic acid esters", Bioorganic & Medicinal Chemistry, Pergamon, GB, vol. 15, No. 1 Nov. 15, 2006 (Nov. 15, 2006), pp. 333-342.

Schimrigk, et al., "Oral fumaric acid esters for the treatment of active multiple sclerosis: an open-label, baseline-controlled pilot study", European Journal of Neurology, 2006, 13: pp. 604-610.

Seder et al., Acquisition of lymphokine-producing phenotype by CD4+ T-cells, Ann. Rev. Immunol. (1994), 12: 635-73.

Sharma et al., Distal effect on mass spectral fragmentations of glycolamide esters of 6-methoxy-2-naphthylacetic acid (6-MNA) and the crystal structure of N,N'-dimethyl-glycolamide ester of 6-MNA, Ind. J. Chem. (2004) 43B: 1758-1764.

Sheikh, et al., "Safety Tolerability and Pharmacokinetics of BG-12 Administered with and without Aspirin, Key Findings from a Randomized, Double-blind, placebo-controlled trial in healthy volunteers", Poster P04.136 presented at the 64th Annual Meeting of the American Academy of Neurology, Apr. 21-28, 2012, New Orleans, LA.

Soelberg Sorensen et al., Oral fumarate for relapsing-remitting multiple sclerosis, Lancet (2008), 372: 1447-1448.

Spatz, et al., Methyl Hydrogen Fumarate, Journal of Organic Chemistry, 1958, 23 (10), 1559-1560.

Spencer et al., Induction of glutathione transferases and NAD(P)H: quinone reductase by fumaric acid derivatives in rodent cells and tissues, Cancer Res. (1990), 50: 7871-7875.

Stoof et al., the antipsoriatic drug dimethylfumarate strongly suppresses chemokine production in human keratinocytes and peripheral blood mononuclear cells, Br. J. Dermatol. (2001), 144: 1114-1120.

Tabruyn et al., NF-κB: a new player in angiostatic therapy. Angiogenesis (2008), 11, 101-106.

Talath et al., Stability studies of some glycolamide ester prodrugs of niflumic acid in aqueous buffers and human plasma by HPLC with UV detection, Arz. Forsch Drug Res. (2006), 56(9): 631-639.

Talath et al., Synthesis, stability studies, anti-inflammatory activity and ulcerogenicity of morpholinoalkyl ester prodrugs of niflumic acid, Arz. Forsch Drug Res. (2006), 56(11): 744-752.

Tang et al., The psoriasis drug monomethylfumarate is a potent nicotinic acid receptor agonist, Biochem. Biophys. Res. Comm. (2008), doi:10.1016/j.bbrc.2008.08.041, 4 pages.

Thing et al., "Prolonged naproxen joint residence time after intra-articular injection of lipophilic solutions comprising a naproxen glycolamide ester prodrug in the rat", International Journal of Pharmaceutics 451; Apr. 2013; pp. 34-40.

Thomson et al., FK 506: a novel immunosuppressant for treatment of autoimmune disease: rationale and preliminary clinical experience at the University of Pittsburgh, Springer Semin. Immunopathol. (1993), 14(4): 323-344.

Tracey et al., Tumor necrosis factor antagonist mechanisms of action: a comprehensive review. Pharmacology & Therapeutics (2008), 117, 244-279.

Treumer et al., Dimethylfumarate is a potent inducer of apoptosis in human T cells. J Invest Dermatol (2003), 121, 1383-1388.

Van Schoor et al., Effect of inhaled fluticasone on bronchial responsiveness to neurokinin A in asthma. Eur Respir J (2002), 19, 997-1002.

Vandermeeren et al., Dimethylfumarate is an inhibitor of cytokine-induced E-selectin, VCAM-1, and ICAM-1 expression in human endothelial cells. Biochem Biophys Res Commun (1997), 234, 19-23.

Villegas et al., A new flavonoid derivative, dosmalfate, attenuates the development of dextran sulphate sodium-induced colitis in mice. Int'l Immunopharmacol (2003), 3, 1731-1741.

Virley, Developing therapeutics for the treatment of multiple sclerosis. NeuroRx (2005), 2, 638-649.

Wadhwa et al., Glycolamide esters of 6-methoxy-2-naphthylacetic acid as potential prodrugs—Synthetic and spectral studies, Ind. J. Chem. (1995), 34B: 408-415.

Wain et al., Treatment of severe, recalcitrant, chronic plaque psoriasis with fumaric acid esters: a prospective study, Br. J. Dermatol. (2009), DOI 10.1111/j.1365-2133.2009.09267.x, 8 pages.

Wakkee et al., Drug evaluation: BG-12, an immunomodulary dimethylfumarate, Curr. Opin. Invest. Drug. (2007), 8(11): 955-962.

Wang, et al., Evidence-Based Treatment of Chronic Leg Ulcers in a Patient with Necrobiosis Lipoidica Deabeticorum. Chinese Journal of Evidence-Based Medicine (2007), 7(11): 830-835 (Chinese with English abstract).

Weber et al., Synthesis, In Vitro Skin Permeation Studies, and PLS-Analysis of New Naproxen Derivatives, Pharm. Res. (2001) 18(5): 600-607.

Weber et al., Treatment of disseminated granuloma annulare with low-dose fumaric acid, Acta Derm. Venereol. (2009), 89: 295-298.

Werdenberg et al., Presystemic metabolism and intestinal absorption of antipsoriatic fumaric acid esters, Biopharm. Drug. Dispos. (2003), 24: 259-273.

Wingerchuk et al., Multiple sclerosis: current pathophysiological concepts. Lab Invest (2001), 81(3), 263-281.

Winkler, et al., Oxidative damage and age-related macular degeneration. Molecular vision, (1999), 5:32, 11 pages.

Woodworth et al., Oral BG-12 in combination with interferon beta or glatiramer acetate: pharmacokinetics, safety and tolerability, 26th Congress Eur. Cmtee. Treat. Res. Mult. Scler. (2010), poster: 1 page.

Woodworth et al., "Pharmacokinetics of Oral BG-12 Alone Compared with BG-12 and Interferon B-1a or Glatiramer Acetate Administered Together, Studied in Healthy Volunteers", Poster P04.207 presented at the 62nd Annual Meeting of the American Academy of Neurology, Apr. 10-17, 2010, Toronto, Ontario, Canada, 2 pages.

(56) References Cited

OTHER PUBLICATIONS

Wu et al., "Regulatory perspectives of Type II prodrug development and time-dependent toxicity management: Nonclinical Pharm/Tox analysis and the role of comparative toxicology", Science Direct, Toxicology 236; Apr. 2007; pp. 1-6.
Wustrow et al., Comparison of the efficacy and tolerability of a novel methyl hydrogenfumarate prodrug with dimethylfumarate in rodent EAE and GI irritation models, XenoPort, Inc., Oct. 13-16, 2010, 1 page.
Xenoport, Inc., XenoPort announces presentation of preclinical data for novel fumarate analog XP23829 at ECTRIMS, Press Release dated Oct. 13, 2010, 3 pages.
Yang et al., Neuroprotective effects of the triterpenoid, CDDO methyl amide, a potent inducer of Nrf2-mediated transcription, PLOS One (2009), 4(6) doi:10.1371/journal.pone.0005757: 13 pages.
Yazdi et al., Fumaric acid esters. Clinics Dermatology (2008), 26, 522-526.
Zhu et al., Inhibition of dendritic cell differentiation by fumaric acid esters, J. Invest. Dermatol. (2001), 116: 203-208.
Altschul et al., "Gapped BLAST and PSI-BLAST: a new generation of protein database search programs," Nucleic Acids Research, 1997, vol. 25, No. 17, pp. 3389-3402.
Associated Press; FDA mulls drug to slow late-stage Alzheimer's [online]; [retrieved on Sep. 24, 2003]; retrieved from the internet, <http://www.cnn.com/2003/HEALTH/conditions/09/24/alzheimers.drug.ap/index.html>, Sep. 24, 2003; 2 pages.
Bar-Or et al., "Clinical efficacy of BG-12 (dimethyl fumarate) in patients with relapsing-remitting multiple sclerosis: subgroup analyses of the DEFINE study," J. Neurol, 2013, vol. 260, pp. 2297-2305.
Benoit et al., Etude Clinique de L'ester B-Morpholinoethylique de L'Acide Niflumique en Stomatologie Infantile, Rev. Odontostomatol Midi Fr. (1975), 4: 249-261.
Bertone, "Prevalence of Gastric Ulcers in Elite, Heavy Use Western Performance Horses," AAEP Proceedings (2000). 46: 256-259.
Boehncke, "Animal Models of T Cell-Mediated Skin Diseases, Chapter 12: The Psoriasis SCID Mouse Model: A Tool for Drug Discovery?" Ernst Schering Res Found Workshop 50, Zollner et al., eds. New York: Springer (2005) pp. 213-234.
Brown et al., "Goodman & Gilman's The Pharmacological Basis of Therapeutics, Tenth Edition: Chapter 7, Muscarinic Receptor Agonists and Antagonists," A. Gilman, J. Hardman and L. Limbird, eds., Mc-Graw Hill Press, 2001, pp. 155-173.
Bruhn et al., "Concordance between enzyme activity and genotype of glutathione S-transferase theta (GSTT1)," Biochemical Pharmacology, 1998, vol. 56, pp. 1189-1193.
Büyükcoskun, Central Effects of Glucagon-like Peptide-1 on Cold Restraint Stress-induced Gastric Mucosal Lesions, Turk J. Gastroenterol (2007), 18(3): 150-156.
Büyükcoskun, Role of Intracerebroventricular Vasopressin in the Development of Stress-Induced Gastric Lesions in Rats, Physiol. Res. (1999), 48: 451-455.
Caira, "Crystalline Polymorphism of Organic Compounds," Topics in Current Chemistry, Springer, Berlin, DE (1998), vol. 198, pp. 163-208.
Camandola et al., "NF-kB as a therapeutic target in neurodegenerative diseases," Expert Opinion Therapeutic Targets (2007), 11(2), pp. 123-132.
Chaudhary et al., "Enhancement of solubilization and bioavailability of poorly soluble drugs by physical and chemical modifications: A recent review," Journal of Advanced Pharmacy Education & Research (2012), 2(1), pp. 32-67.
Chen et al., "Nanonization strategies for poorly water-soluble drugs," Drug Discovery Today, 2010, pp. 1-7.
Damasio; "Alzheimer's Disease and Related Dementias;" Cecil Textbook of Medicine; 1996; 20th Edition, vol. 2; pp. 1992-1996.
Etter et al., "The Use of Cocrystallization as a Method of studying Hydrogen Bond Preferences of 2-Aminopyrimidine," Journal of the Chemical Society (1990), No. 8, pp. 589-591.

Etter et al., "Graph Set Analysis of Hydrobgen-Bond Patterns in Organic Crystals," Acta Crystallogr., Sect. B, Struct. Sci. (1990), B46, pp. 256-262.
Etter et al., "Hydrogen Bond Directed Cocrystallization and Molecular Recognition Properties of Diarylureas," Journal of the Chemical Society (1990), No. 112, pp. 8415-8426.
Fits et al., Imiquimod-Induced Psoriasis-Like Skin Inflammation in Mice Is Mediated via the IL-23/IL-17 Axis, J. Immunol. (2009), 182: 5836-5845.
Food and Drug Administration—Department of Health and Human Services; "International Conference on Harmonisation; Guidelines for the Photostability Testing of New Drug Substances and Products; Availability; Notice," Federal Register, vol. 62, No. 95; May 16, 1997, pp. 27115-27122.
Gorbitz et al., "On the inclusion of solvent molecules in the crystal structures of organic compounds," Acta Cryst. (2000), B56, pp. 526-534.
Griffin, et al., The Chemistry of Photodimers of Maleic and Fumaric Acid Derivatives. I. Dimethyl Fumarate Dimer; J. Am. Chem. Soc. (1961), 83: pp. 2725-2728.
Jamil, et al., "Studies of Photostability of Reserpine in Parenteral Solutions," Die Pharmazie (1983), 38: pp. 467-469.
Killestein, et al., "Oral treatment for multiple sclerosis," Lancet Neurology, Lancet Publishing Group, London, GB, vol. 10, No. 11, Nov. 2011, pp. 1026-1034.
Kumar et al., "Molecular Complexes of Some Mono- and Dicarboxylic Acids with trans-1,4-Dithiane-1,4-dioxide," American Chemical Society, Crystal Growth & Design (2002), 2(4), pp. 313-318.
Layzer; "Section Five—Degenerative Diseases of the Nervous System"; Cecil Textbook of Medicine; 1996; 20th Edition, vol. 2; pp. 2050-2057.
Lei et al., "Novel Technology of Dimethyl Fumarate Synthesis," Ziyuan Kaifa Yu Shichang (2011), 27(9), pp. 787-789.
Los et al., Nuevos Estered De Acidos Anilinonicotinicos Y N-Fenilantranilicos Sustituidos, Il Farmaco—Ed. Sc. (1980), 36(5): 372-85.
Meissner et al., "Dimethyl fumarate—only an anti-psoriatic medication?", Journal Der Deutschen Demrmatologischen Gesellschaft (2012), vol. 10, pp. 793-801.
Merisko-Liversidge et al., "Nanosizing: a formulation approach for poorly-water-soluble compounds," European Journal of Pharmaceutical Sciences, 18 (2003), pp. 113-120.
Miller et al., Experimental Autoimmune Encephalomyelitis in the Mouse, Current Protocols in Immunology (2007), Supp. 78: 15.1.1-15.1.18.
Muller et al., "High-performance liquid chromatography/fluorescence detection of 5-methylglutathione formed by glutathione-S-transferase T1 in vitro," Arch Toxicol, 2001, vol. 74, pp. 760-767.
Panagiotou et al., "Form Nanoparticles via Controlled Crystallization," Chemical Engineering Progress; Oct. 2008, 104, 10, pp. 33-39.
Pathak et al., "Supercritical fluid technology for enhanced drug delivery," Expert Opin. Drug Deliv. (2005) 2(4):747-761.
Pemble et al., "Human glutathione S-transferase Theta (GSTT1): cDNA cloning and the characterization of a genetic polymorphism," Biochem. J., 1994, vol. 300, pp. 271-276.
Sawant et al., "Necessity of Establishing Chemical Integrity of Polymorphs of Drug Substance Using a Combination of NMR, HPLC, Elemental Analysis, and Solid-State Characterization Techniques: Case Studies," Organic Process Research & Development (2013), vol. 17, No. 3, pp. 519-532.
Shan et al., "The role of cocrystals in pharmaceutical science," Drug Discovery Today (2008), 13(9/10), pp. 440-446.
Spencer, "Tecfidera: an approach for repurposing," Pharmaceutical Patent Analyst, 2014, vol. 3(2), pp. 183-198.
Sprenger et al., "Characterization of the glutathione S-transferase GSTT1 deletion: discrimination of all genotypes by polymerase chain reaction indicates a trimodular genotype-phenotype correlation," Pharmacogenetics, 2000, vol. 10, pp. 557-565.
Steckel et al., "The extrusion and speronization of chitosan," Pharmaceutical Technology Europe http://www.pharmtech.com/extrusion-and-spheronization-chitosan, published Jul. 2, 2007, pp. 1-12.

(56) References Cited

OTHER PUBLICATIONS

The Engineering Tool Box, "Acids—pH Values," http://www.engineeringtoolbox.com/acids-ph-d_401.html, published Feb. 24, 2006, pp. 1-2.
Van Schoor et al., the effect of the NK2 tachykinin receptor antagonist SR 48968 (saredutant) on neurokinin A-induced bronchoconstriction in asthmatics, Eur Respir J (1998) 12: 17-23.
Vishweshwar et al., "Pharmaceutical Co-Crystals," Journal of Pharmaceutical Sciences (2006), 95(3), pp. 499-516.
Whiteley et al., Models of Inflammation: Measuring Gastrointestinal Ulceration in the Rat, Curr. Protocol. Pharm. (1998): 10.2.1-10.2.4.
Yamada et al., "Synthesis and Polymerization of Unsaturated Dibasic Acid Derivatives," Yuki Gosei Kagaku Kyokaishi (1965), 23(2), 19 pages.
Zhang et al., "Synthesis of Dimethyl Fumarate with Orthogonal Test," Jingxi Hua on Zhongjianti (2006), 36(6), pp. 71-72.
Zhao et al., "Synthesis and antimicrobial active of monomethyl fumarate," Shipin Gongye Keji (2008), 29(6), pp. 259-262.
Zheng et al., "Improved Preparation of Monomethyl Fumarate," Huaxue Shijie (2004), 45(4), pp. 207-208, 217.
U.S. Appl. No. 13/973,780, filed Aug. 22, 2013, Cundy et al.
O'Donnell et al., "Remington the Science and Practice of Pharmacy" 21st Edition, 2005, Chapter 52, pp. 1025-1036.
Bhattacharya et al., Polymorphism in Pharmaceutical Solids: Thermoanalytical and Crystallographic Methods 334 (Brittain H. ed., 2d ed. Informa Healthcare USA, Inc. 2009) (1999), 20 pages.
Ivanisevic et al., "Uses of X-Ray Powder Diffraction in the Pharmaceutical Industry," Pharmaceutical Formulation & Quality, 32 (2011), pp. 30-33.
Gogas et al., "Comparison of the efficacy and tolerability of a novel methyl hydrogen fumarate prodrug with dimethyl fumarate in rodent EAE and GI irritation models," Multiple Sclerosis, 2010, vol. 16, No. 10 Supplement, pp. S230-S231.
Dow, "Methocel Cellulose Technical Handbook", <http://www.dow.com/dowwolff/en/pdf/192-01062.pdf>, 2002, 32 pages.
General pharmaceutics (5th edition), 1997, 5 pages, published in Japan.
U.S. Appl. No. 14/990,582, filed Jan. 7, 2016, Karaborni et al.
Tammara et al., "Morpholinoalkyl Ester Prodrugs of Diclofenac: Synthesis, In Vitro and In Vivo Evaluation," Journal of Pharmaceutical Sciences, 1994 vol. 83, No. 5, pp. 644-648.
General pharmaceutics (5th edition) with partial translation of pp. 208-209, 1997, 5 pages, published in Japan.
Compound (CAS RN 473669-27-1) entered STN chemical database on Nov. 15, 2002 by Ambinter, 4 pp.
Booth et al., "Regulation of dimethyl-fumarate toxicity by proteasome inhibitors," Cancer Biology & Therapy, Dec. 2014, vol. 15(12), pp. 1646-1657.
Silhavy et al., "Fumaric Acid Esters Can Block Pro-Inflammatory Actions of Human CRP and Ameliorate Metabolic Disturbances in Transgenic Spontaneously Hypertensive Rats," PLOS ONE, Jul. 2014, vol. 9, Issue 7, e101906, pp. 1-9.
Shah, D Thassu. Hypromellose. Oct. 8, 2008. p. 326.
"An Immediate Release, Pearlescent, Film Coating System from Colorcon". OPADRY FX. pp. 1-7.
"The Influence of Film Coatings on Performance of Hypromellose Matrices".OPADRY II, OPADRY AMB. pp. 1-3.

\* cited by examiner

METHODS OF ADMINISTERING MONOMETHYL FUMARATE AND PRODRUGS THEREOF HAVING REDUCED SIDE EFFECTS

CROSS REFERENCE TO RELATED APPLICATIONS

This application claims the benefit under 35 U.S.C. § 119(e) of U.S. Provisional Application Ser. Nos. 61/800,132, filed Mar. 15, 2013; 61/692,168, filed Aug. 22, 2012; 61/713,897, filed Oct. 15, 2012; 61/733,234, filed Dec. 4, 2012; 61/769,513, filed Feb. 26, 2013; 61/841,513, filed Jul. 1, 2013; 61/692,174, filed Aug. 22, 2012; 61/713,961, filed Oct. 15, 2012; and 61/837,796, filed Jun. 21, 2013; the contents of each of which are incorporated herein by reference in their entirety.

TECHNICAL FIELD

Disclosed herein are methods of reducing patient flushing while administering monomethyl fumarate and/or a prodrug thereof during the treatment of diseases such as multiple sclerosis and psoriasis.

BACKGROUND

Fumaric acid esters (FAEs) are approved in Germany for the treatment of psoriasis, are being evaluated in the United States for the treatment of psoriasis and multiple sclerosis, and have been proposed for use in treating a wide range of immunological, autoimmune, and inflammatory diseases and conditions.

FAEs and other fumaric acid derivatives have been proposed for use in treating a wide-variety of diseases and conditions involving immunological, autoimmune, and/or inflammatory processes including psoriasis (Joshi and Strebel, WO 1999/49858; U.S. Pat. No. 6,277,882; Mrowietz and Asadullah, Trends Mol Med 2005, 111(1), 43-48; and Yazdi and Mrowietz, Clinics Dermatology 2008, 26, 522-526); asthma and chronic obstructive pulmonary diseases (Joshi et al., WO 2005/023241 and US 2007/0027076); cardiac insufficiency including left ventricular insufficiency, myocardial infarction and angina pectoris (Joshi et al., WO 2005/023241; Joshi et al., US 2007/0027076); mitochondrial and neurodegenerative diseases such as Parkinson's disease, Alzheimer's disease, Huntington's disease, retinopathia pigmentosa and mitochondrial encephalomyopathy (Joshi and Strebel, WO 2002/055063, US 2006/0205659, U.S. Pat. No. 6,509,376, U.S. Pat. No. 6,858,750, and U.S. Pat. No. 7,157,423); transplantation (Joshi and Strebel, WO 2002/055063, US 2006/0205659, U.S. Pat. No. 6,359,003, U.S. Pat. No. 6,509,376, and U.S. Pat. No. 7,157,423; and Lehmann et al., Arch Dermatol Res 2002, 294, 399-404); autoimmune diseases (Joshi and Strebel, WO 2002/055063, U.S. Pat. No. 6,509,376, U.S. Pat. No. 7,157,423, and US 2006/0205659) including multiple sclerosis (MS) (Joshi and Strebel, WO 1998/52549 and U.S. Pat. No. 6,436,992; Went and Lieberburg, US 2008/0089896; Schimrigk et al., Eur J Neurology 2006, 13, 604-610; and Schilling et al., Clin Experimental Immunology 2006, 145, 101-107); ischemia and reperfusion injury (Joshi et al., US 2007/0027076); AGE-induced genome damage (Heidland, WO 2005/027899); inflammatory bowel diseases such as Crohn's disease and ulcerative colitis; arthritis; and others (Nilsson et al., WO 2006/037342 and Nilsson and Muller, WO 2007/042034).

Fumaderm®, an enteric coated tablet containing a mixture of salts of monoethyl fumarate and dimethyl fumarate was approved in Germany in 1994 for the treatment of psoriasis. Dimethyl fumarate (DMF) is rapidly metabolized in vivo to monomethyl fumarate (MMF), and hence DMF is considered to be a prodrug of MMF.

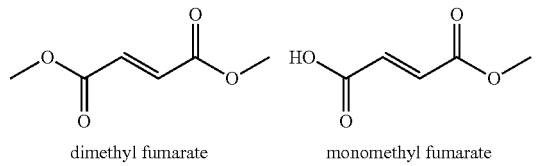

dimethyl fumarate    monomethyl fumarate

Fumaderm® is dosed three times per day with 1-2 grams/day administered for the treatment of psoriasis. Fumaderm® exhibits a high degree of interpatient variability with respect to drug absorption and food strongly reduces bioavailability. Absorption is thought to occur in the small intestine with peak levels achieved 5-6 hours after oral administration. Significant side effects occur in 70-90% of patients (Brewer and Rogers, Clin Expt'l Dermatology 2007, 32, 246-49; and Hoelhagel et al., Br J Dermatology 2003, 149, 363-369). Side effects of current FAE therapy include gastrointestinal upset including nausea, vomiting, and diarrhea; and transient flushing of the skin. In particular, significant flushing incidences have been reported in patients with psoriasis after administration of BG00012 (DMF) (Artuc et al., Br J Dermatology Preprint, 2006, 154, 21). Artuc et al. found flushing incidences in 18 of 24 patients dosed. They also observed increases in $PGD_2$, $PGF_2$, and serotonin plasma levels. The skin flushing side effect of FAEs is thought to be the result of interactions with the hydroxy-carboxylic acid receptor, $HCA_2$, on keratinocytes, as well as on Langerhans cells in the skin (Blad et al., Biological and Pharmacological Roles of HCA Receptors, Advances in Pharmacology, 2011, 62, 219-250).

Fumaric acid derivatives (Joshi and Strebel, WO 2002/055063, US 2006/0205659, and U.S. Pat. No. 7,157,423 (amide compounds and protein-fumarate conjugates); Joshi et al., WO 2002/055066 and Joshi and Strebel, U.S. Pat. No. 6,355,676 (mono and dialkyl esters); Joshi and Strebel, WO 2003/087174 (carbocyclic and oxacarbocyclic compounds); Joshi et al., WO 2006/122652 (thiosuccinates); Joshi et al., US 2008/0233185 (dialkyl and diaryl esters); Nielsen and Bundgaard, J Pharm Sci 1988, 77(4), 285-298 (glycolamide ester prodrugs); and Nilsson et al., US 2008/0004344 (salts)) have been developed in an effort to overcome the deficiencies of current FAE therapy. Controlled release pharmaceutical compositions comprising fumaric acid esters are disclosed by Nilsson and Müller, WO 2007/042034; by Nilsson and Rupp, US 2012/0034274 and US 2012/0034303. These last two publications describe FAE formulations exhibiting reduced flushing in patients.

SUMMARY

Disclosed herein are methods of systemically administering a therapeutically effective amount of a compound selected from (i) monomethyl fumarate (MMF), (ii) a prodrug of monomethyl fumarate, and (iii) a combination thereof, to treat a disease in each patient of a population of patients in need of such treatment. The methods comprise administering the compound(s) to each patient to achieve across the population of patients a maximum average concentration, as defined herein, of monomethyl fumarate in the blood plasma of the patients of less than 500 ng/ml. In certain aspects, the maximum average concentration of monomethyl fumarate in the blood plasma of the patients is maintained at less than 400 ng/ml.

The methods further comprise administering the compound(s) to each patient to achieve, across the population of patients, an average Cmax, as defined herein, of monomethyl fumarate in the blood plasma of the patients of less than 1100 ng/ml. In certain aspects, the average Cmax of monomethyl fumarate in the blood plasma of the patients is maintained at less than 600 ng/ml. In other aspects, the average Cmax of monomethyl fumarate in the blood plasma of the patients is maintained at less than 400 ng/ml.

The methods are effective in reducing the incidence/frequency of flushing across the population of patients.

Also disclosed herein are methods of systemically administering a therapeutically effective amount of a compound selected from (i) monomethyl fumarate (MMF), (ii) a prodrug of monomethyl fumarate, and (iii) a combination thereof, to treat a disease in each patient in a population of patients in need of such treatment. The methods comprise administering the compound(s) to each patient to achieve across the population of patients: an average maximum rate of rise in monomethyl fumarate concentration in the blood plasma of the patients of less than 0.25 wt % ng-eq of MMF dosed/ml/hr. In certain aspects, the average maximum rate of rise in monomethyl fumarate concentration is less than 0.20 wt % ng-eq of MMF dosed/ml/hr. In other aspects, the average maximum rate of rise in monomethyl fumarate concentration is less than 0.15 wt % ng-eq of MMF dosed/ml/hr. In other aspects, the average maximum rate of rise in monomethyl fumarate concentration is less than 500 ng/mL/hr. In other aspects, the average maximum rate of rise in monomethyl fumarate concentration is less than 400 ng/mL/hr. In other aspects, the average maximum rate of rise in monomethyl fumarate concentration is less than 250 ng/mL/hr. In other aspects, the average maximum rate of rise in monomethyl fumarate concentration is less than 200 ng/mL/hr. In other aspects, the average maximum rate of rise in monomethyl fumarate concentration is less than 180 ng/mL/hr. In other aspects, the average maximum rate of rise in monomethyl fumarate concentration is less than 140 ng/mL/hr.

In some embodiments, the methods comprise administering the compound(s) to each patient in a population of patients to achieve across the population an average maximum rate of rise in monomethyl fumarate concentration in the blood plasma of the patients of less than 0.25 wt % ng-eq of MMF dosed/ml/hr, and an average monomethyl fumarate concentration in the blood plasma of the patients, measured at a time of said maximum rate of rise, of less than 250 ng/ml. In another embodiment, the average maximum rate of rise in monomethyl fumarate concentration in the blood plasma of the patients is less than 0.15 wt % ng-eq of MMF dosed/ml/hr, and an average monomethyl fumarate concentration in the blood plasma of the patients, measured at a time of said maximum rate of rise, is less than 200 ng/ml. In yet another embodiment, the average maximum rate of rise in monomethyl fumarate concentration in the blood plasma of the patients is less than 0.10 wt % ng-eq of MMF dosed/ml/hr, and an average monomethyl fumarate concentration in the blood plasma of the patients, measured at a time of said maximum rate of rise, is less than 140 ng/ml.

Also disclosed herein are methods of systemically administering a therapeutically effective amount of a compound selected from (i) monomethyl fumarate (MMF), (ii) a prodrug of monomethyl fumarate, and (iii) a combination thereof, to treat a disease in a patient in need of such treatment, comprising one of: (a) orally administering to the patient, at a dosing frequency of not more than twice per day, an enteric-coated oral or a non-enteric-coated sustained release dosage form containing a therapeutically effective dose of the compound(s), wherein the dosage form, when subjected to an in vitro dissolution test employing as a dissolution medium 750 mL of 0.1 N hydrochloric acid, at pH 1.2, for a period of 2 hours, followed by addition of 250 mL of 200 mM tribasic sodium phosphate buffer resulting in an adjustment of the pH of the dissolution medium to 6.8, the dissolution medium being maintained at 37° C. and stirred at 100 rpm, releases: (i) less than 10 wt % of the dose over an initial 2 hours of the in vitro dissolution test; (ii) at least 90 wt % of the dose over not less than an initial 8 hours of the in vitro dissolution test; (iii) no more than 30 wt % of the dose in any one hour during the in vitro dissolution test; and (iv) no more than 40 wt % of the dose in any consecutive two hours during the in vitro dissolution test; or (b) orally administering to the patient, at a frequency of not more than twice per day, a non-enteric-coated oral sustained release dosage form containing a therapeutically effective dose of the compound(s), wherein the dosage form, when subjected to an in vitro dissolution test employing as a dissolution medium 750 mL of 0.1 N hydrochloric acid, at pH 1.2, for a period of 2 hours, followed by addition of 250 mL of 200 mM tribasic sodium phosphate buffer resulting in an adjustment of the pH of the dissolution medium to 6.8, releases (i) at least 90 wt % of the dose over not less than an initial 8 hours of the in vitro dissolution test; (ii) no more than 30 wt % of the dose in any one hour during the in vitro dissolution test; and (iii) no more than 40 wt % of the dose in any consecutive two hours during the in vitro dissolution test.

The therapeutic treatments disclosed herein can be used to treat any number of diseases for which FAEs are known or thought to be therapeutically effective. In certain embodiments, the therapeutic treatments disclosed herein can be used to treat adrenal leukodystrophy, AGE-induced genome damage, Alexanders Disease, Alper's Disease, Alzheimer's disease, amyotrophic lateral sclerosis, angina pectoris, arthritis, asthma, balo concentric sclerosis, Canavan disease, cardiac insufficiency including left ventricular insufficiency, central nervous system vasculitis, Charcott-Marie-Tooth Disease, childhood ataxia with central nervous system hypomyelination, chronic idiopathic peripheral neuropathy, chronic obstructive pulmonary disease, Crohn's disease, diabetic retinopathy, graft versus host disease, hepatitis C viral infection, herpes simplex viral infection, human immunodeficiency viral infection, Huntington's disease, irritable bowel disorder, ischemia, Krabbe Disease, lichen planus, macular degeneration, mitochondrial encephalomyopathy, monomelic amyotrophy, multiple sclerosis, myocardial infarction, neurodegeneration with brain iron accumulation, neuromyelitis optica, neurosarcoidosis, NF-κB mediated diseases, optic neuritis, pareneoplastic syndromes, Parkinson's disease, Pelizaeus-Merzbacher disease, primary lateral sclerosis, progressive supranuclear palsy, psoriasis, reperfusion injury, retinopathia pigmentosa, Schilders Disease, subacute necrotizing myelopathy, susac syndrome, transplantation rejection, transverse myelitis, a tumor, ulcerative colitis, Zellweger's syndrome, granulomas including annulaire, pemphigus, bollus pemphigoid, behcet's, contact dermatitis, acute dermatitis, chronic dermatitis, alopecia greata (totalis and universalis), sarcoidosis, cutaneous sarcoidosis, pyoderma gangrenosum, cutaneous lupus, Crohn's disease or cutaneous Crohn's disease. In some embodiments, the therapeutic treatments disclosed herein can be used for the treatment of multiple sclerosis and psoriasis.

In a first aspect, the compound being administered comprises monomethyl fumarate.

In a second aspect, the compound being administered comprises a prodrug of monomethyl fumarate.

In a third aspect, the prodrug of monomethyl fumarate comprises a compound of Formula (I):

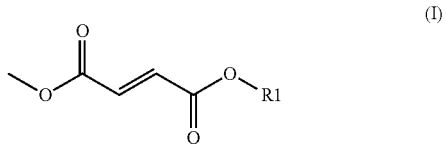

(I)

or a pharmaceutically acceptable salt thereof, wherein $R^1$ is chosen from a $C_1$ to $C_6$ alkyl.

In a fourth aspect, the prodrug of monomethyl fumarate comprises a compound of Formula (II):

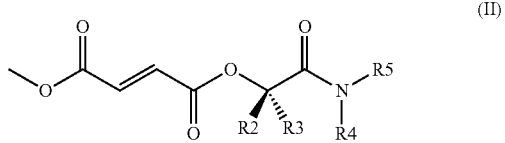

(II)

or a pharmaceutically acceptable salt thereof, wherein:

$R^2$ and $R^3$ are independently chosen from hydrogen, $C_{1-6}$ alkyl, and substituted $C_{1-6}$ alkyl;

$R^4$ and $R^5$ are independently chosen from hydrogen, $C_{1-6}$ alkyl, substituted $C_{1-6}$ alkyl, $C_{1-6}$ alkoxy, substituted $C_{1-6}$ alkoxy, $C_{1-6}$ alkoxycarbonyl, substituted $C_{1-6}$ alkoxycarbonyl, $C_{1-6}$ heteroalkyl, substituted $C_{1-6}$ heteroalkyl, $C_{4-12}$ cycloalkylalkyl, substituted $C_{4-12}$ cycloalkylalkyl, $C_{7-12}$ arylalkyl, and substituted $C_{7-12}$ arylalkyl; or $R^4$ and $R^5$ together with the nitrogen to which they are bonded form a ring chosen from a $C_{5-10}$ heteroaryl, substituted $C_{5-10}$ heteroaryl, $C_{5-10}$ heterocycloalkyl, and substituted $C_{5-10}$ heterocycloalkyl; and wherein each substituent group is independently chosen from halogen, —OH, —CN, —CF$_3$, =O, —NO$_2$, benzyl, —C(O)NR$^{11}$$_2$, —R$^{11}$, —OR$^{11}$, —C(O)R$^{11}$, —COOR$^{11}$, and —NR$^{11}$$_2$ wherein each R$^{11}$ is independently chosen from hydrogen and $C_{1-4}$ alkyl.

In a fifth aspect, the prodrug of monomethyl fumarate comprises a compound of Formula (III):

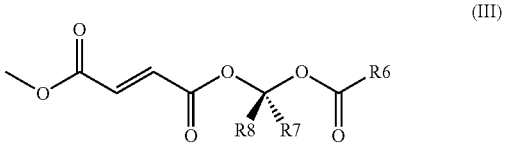

(III)

or a pharmaceutically acceptable salt thereof, wherein:

$R^6$ is chosen from $C_{1-6}$ alkyl, substituted $C_{1-6}$ alkyl, $C_{1-6}$ heteroalkyl, substituted $C_{1-6}$ heteroalkyl, $C_{3-8}$ cycloalkyl, substituted $C_{3-8}$ cycloalkyl, $C_{6-8}$ aryl, substituted $C_{6-8}$ aryl, and —OR$^{10}$ wherein R$^{10}$ is chosen from $C_{1-6}$ alkyl, substituted $C_{1-6}$ alkyl, $C_{3-10}$ cycloalkyl, substituted $C_{3-10}$ cycloalkyl, $C_{6-10}$ aryl, and substituted $C_{6-10}$ aryl;

$R^7$ and $R^8$ are independently chosen from hydrogen, $C_{1-6}$ alkyl, and substituted $C_{1-6}$ alkyl; and wherein each substituent group is independently chosen from halogen, —OH, —CN, —CF$_3$, =O, —NO$_2$, benzyl, —C(O)NR$^{11}$$_2$, —R$^{11}$, —OR$^{11}$, —C(O)R$^{11}$, —COOR$^{11}$, —N(R$^{11}$)C(O)C(R$^{11}$)$_2$NR$^{11}$$_2$, and —NR$^{11}$$_2$ wherein each R$^{11}$ is independently chosen from hydrogen and $C_{1-4}$ alkyl.

In a sixth aspect, the prodrug of monomethyl fumarate comprises a compound of Formula (IV):

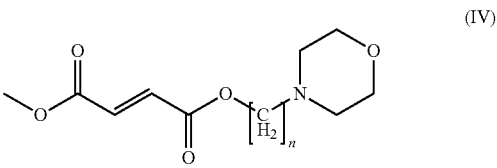

(IV)

or a pharmaceutically acceptable salt thereof, wherein n is an integer from 2 to 6.

FIGURES

Figure 1:
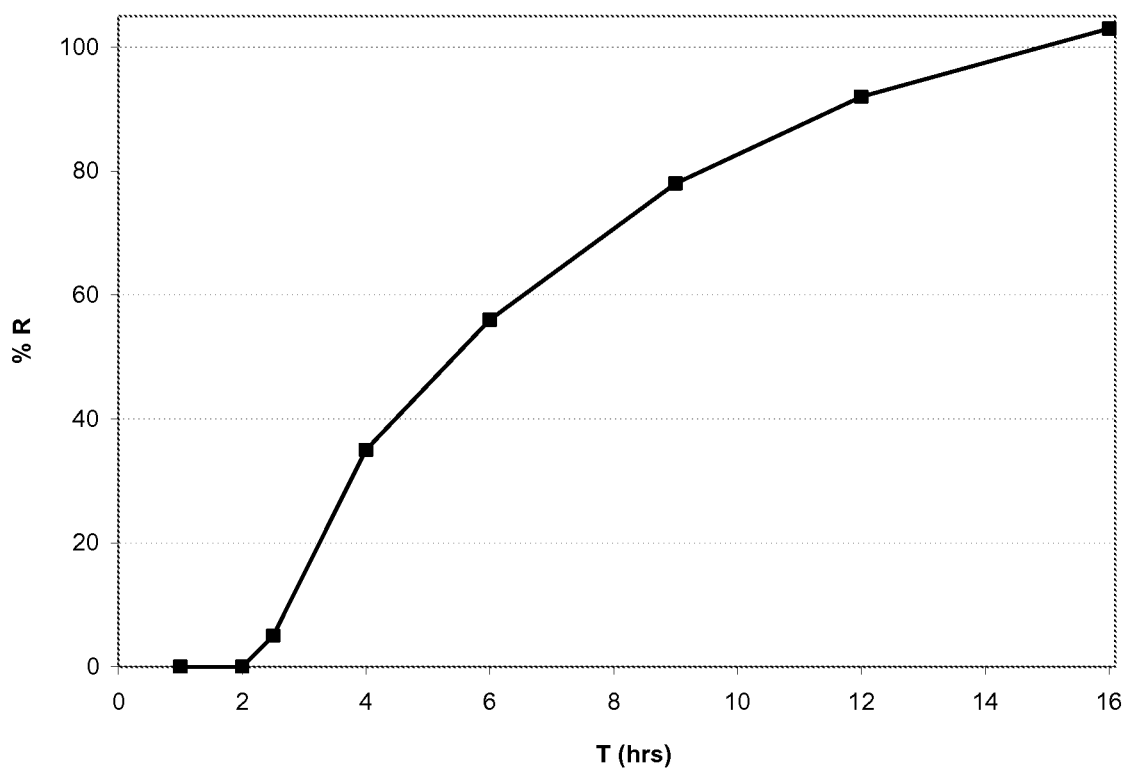
FIG. 1 shows the in vitro release profile of an enteric-coated sustained released tablet according to Example 1.

The curves in the above figures, where applicable, were fitted using a Hill $E_{max}$ model.

DEFINITIONS

A dash ("-") that is not between two letters or symbols is used to indicate a point of attachment for a moiety or substituent. For example, —CONH$_2$ is bonded through the carbon atom.

"Alkyl" refers to a saturated or unsaturated, branched, or straight-chain, monovalent hydrocarbon radical derived by the removal of one hydrogen atom from a single carbon atom of a parent alkane, alkene, or alkyne. Examples of alkyl groups include, but are not limited to, methyl; ethyls such as ethanyl, ethenyl, and ethynyl; propyls such as propan-1-yl, propan-2-yl, prop-1-en-1-yl, prop-1-en-2-yl, prop-2-en-1-yl (allyl), prop-1-yn-1-yl, prop-2-yn-1-yl, etc.; butyls such as butan-1-yl, butan-2-yl, 2-methyl-propan-1-yl, 2-methyl-propan-2-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds, and groups having combinations of single, double, and triple carbon-carbon bonds. Where a specific level of saturation is intended, the terms alkanyl, alkenyl, and alkynyl are used. In certain embodiments, an alkyl group can have from 1 to 20 carbon atoms ($C_{1-20}$) in certain embodiments, from 1 to 10 carbon atoms ($C_{1-10}$), in certain embodiments from 1 to 8 carbon atoms ($C_{1-8}$), in certain embodiments, from 1 to 6 carbon atoms ($C_{1-6}$), in certain embodiments, from 1 to 4 carbon atoms ($C_{1-4}$), and in certain embodiments, from 1 to 3 carbon atoms ($C_{1-3}$).

"Aryl" refers to a monovalent aromatic hydrocarbon radical derived by the removal of one hydrogen atom from a single carbon atom of a parent aromatic ring system. Aryl encompasses benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. Aryl encompasses multiple ring systems having at least one carbocyclic aromatic ring fused to at least one carbocyclic aromatic ring, cycloalkyl ring, or heterocycloalkyl ring. For example, aryl includes a phenyl ring fused to a 5- to 7-membered heterocycloalkyl ring containing one or more heteroatoms chosen from N, O, and S. For such fused, bicyclic ring systems wherein only one of the rings is a carbocyclic aromatic ring, the radical carbon atom may be at the carbocyclic aromatic ring or at the heterocycloalkyl ring. Examples of aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In certain embodiments, an aryl group can have from 6 to 20 carbon atoms ($C_{6-20}$), from 6 to 12 carbon atoms ($C_{6-12}$), from 6 to 10 carbon atoms ($C_{6-10}$), and in certain embodiments from 6 to 8 carbon atoms ($C_{6-8}$).

"Arylalkyl" refers to an acyclic alkyl radical in which one of the hydrogen atoms bonded to a carbon atom, typically a terminal or sp$^3$ carbon atom, is replaced with an aryl group. Examples of arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl, or arylalkynyl is used. In certain embodiments, an arylalkyl group is $C_{7-30}$ arylalkyl, e.g., the alkanyl, alkenyl or alkynyl moiety of the arylalkyl group is $C_{1-10}$ and the aryl moiety is $C_{6-20}$, in certain embodiments, an arylalkyl group is $C_{6-18}$ arylalkyl, e.g., the alkanyl, alkenyl or alkynyl moiety of the arylalkyl group is $C_{1-8}$ and the aryl moiety is $C_{6-10}$. In certain embodiments, an arylalkyl group is $C_{7-12}$ arylalkyl.

"Compounds" of Formulae (I)-(IV) disclosed herein include any specific compounds within these formulae. Compounds may be identified either by their chemical structure and/or chemical name. Compounds are named using Chemistry 4-D Draw Pro, version 7.01c (ChemInnovation Software, Inc., San Diego, Calif.). When the chemical structure and chemical name conflict, the chemical structure is determinative of the identity of the compound. The compounds described herein may comprise one or more chiral centers and/or double bonds and therefore may exist as stereoisomers such as double-bond isomers (i.e., geometric isomers), enantiomers, or diastereomers. Accordingly, any chemical structures within the scope of the specification depicted, in whole or in part, with a relative configuration are deemed to encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures may be resolved into their component enantiomers or stereoisomers using separation techniques or chiral synthesis techniques well known to the skilled artisan. Compounds selected from monomethyl fumarate, or a prodrug of monomethyl fumarate such as dimethyl fumarate or a compound of Formulae (I)-(IV), include, but are not limited to, optical isomers thereof, racemates thereof, and other mixtures thereof. In such embodiments, a single enantiomer or diastereomer, i.e., optically active form can be obtained by asymmetric synthesis or by resolution of the racemates. Resolution of the racemates may be accomplished, for example, by conventional methods such as crystallization in the presence of a resolving agent, or chromatography using, for example, chiral stationary phases. Notwithstanding the foregoing, in compounds selected from monomethyl fumarate, or a prodrug of monomethyl fumarate such as dimethyl fumarate or a compound of Formulae (I)-(IV), the configuration of the illustrated double bond is only in the E configuration (i.e. trans configuration).

Compounds selected from monomethyl fumarate, or a prodrug of monomethyl fumarate such as dimethyl fumarate or a compound of Formulae (I)-(IV), may also exist in several tautomeric forms including the enol form, the keto form, and mixtures thereof. Accordingly, the chemical structures depicted herein encompass all possible tautomeric forms of the illustrated compounds. Compounds selected from monomethyl fumarate, or a prodrug of monomethyl fumarate such as dimethyl fumarate or a compound of Formulae (I)-(IV), also include isotopically labeled compounds where one or more atoms have an atomic mass different from the atomic mass conventionally found in nature. Examples of isotopes that may be incorporated into the compounds disclosed herein include, but are not limited to, $^2$H, $^3$H, $^{11}$C, $^{13}$C, $^{14}$C, $^{15}$N, $^{18}$O, $^{17}$O, etc. Compounds may exist in unsolvated forms as well as solvated forms, including hydrated forms and as N-oxides. In general, compounds as referred to herein may be free acid, hydrated, solvated, or N-oxides. Certain compounds may exist in multiple crystalline, co-crystalline, or amorphous forms. Compounds selected from monomethyl fumarate, or a prodrug of monomethyl fumarate such as dimethyl fumarate or a compound of Formulae (I)-(IV), include pharmaceutically acceptable salts thereof, or pharmaceutically acceptable solvates of the free acid form of any of the foregoing, as well as crystalline forms of any of the foregoing.

Compounds selected from monomethyl fumarate, or a prodrug of monomethyl fumarate such as dimethyl fumarate or a compound of any of Formulae (I)-(IV), also include solvates. A solvate refers to a molecular complex of a compound with one or more solvent molecules in a stoichiometric or non-stoichiometric amount. Such solvent molecules are those commonly used in the pharmaceutical art, which are known to be innocuous to a patient, e.g., water, ethanol, and the like. A molecular complex of a compound or moiety of a compound and a solvent can be stabilized by non-covalent intra-molecular forces such as, for example, electrostatic forces, van der Waals forces, or hydrogen bonds. The term "hydrate" refers to a solvate in which the one or more solvent molecules is water.

Further, when partial structures of the compounds are illustrated, an asterisk (*) indicates the point of attachment of the partial structure to the rest of the molecule.

"Cycloalkyl" refers to a saturated or partially unsaturated cyclic alkyl radical. Where a specific level of saturation is intended, the nomenclature cycloalkanyl or cycloalkenyl is used. Examples of cycloalkyl groups include, but are not limited to, groups derived from cyclopropane, cyclobutane, cyclopentane, cyclohexane, and the like. In certain embodiments, a cycloalkyl group is $C_{3-15}$ cycloalkyl, $C_{3-12}$ cycloalkyl, and in certain embodiments, $C_{3-8}$ cycloalkyl.

"Cycloalkylalkyl" refers to an acyclic alkyl radical in which one of the hydrogen atoms bonded to a carbon atom, typically a terminal or $sp^3$ carbon atom, is replaced with a cycloalkyl group. Where specific alkyl moieties are intended, the nomenclature cycloalkylalkanyl, cycloalkylalkenyl, or cycloalkylalkynyl is used. In certain embodiments, a cycloalkylalkyl group is $C_{4-30}$ cycloalkylalkyl, e.g., the alkanyl, alkenyl, or alkynyl moiety of the cycloalkylalkyl group is $C_{1-10}$ and the cycloalkyl moiety is $C_{3-20}$, and in certain embodiments, a cycloalkylalkyl group is $C_{3-20}$ cycloalkylalkyl, e.g., the alkanyl, alkenyl, or alkynyl moiety of the cycloalkylalkyl group is $C_{1-8}$ and the cycloalkyl moiety is $C_{3-12}$. In certain embodiments, a cycloalkylalkyl group is $C_{4-12}$ cycloalkylalkyl.

"Dimethyl fumarate" refers to the dimethyl ester of fumaric acid. The compound has the formula $H_3COOCCH=CHCOOCH_3$, and has a molecular weight of 144.13 daltons. This compound is also known by the names Dimethyl (E)-butenedioate (IUPAC), trans-1,2-Ethylenedicarboxylic acid dimethyl ester and (E)-2-Butenedioic acid dimethyl ester. The compound is also referred to herein by the acronym DMF.

"Disease" refers to a disease, disorder, condition, or symptom of any of the foregoing.

"Drug" as defined under 21 U.S.C. § 321(g)(1) means "(A) articles recognized in the official United States Pharmacopoeia, official Homeopathic Pharmacopoeia of the United States, or official National Formulary, or any supplement to any of them; and (B) articles intended for use in the diagnosis, cure, mitigation, treatment, or prevention of disease in man or other animals; and (C) articles (other than food) intended to affect the structure or any function of the body of man or other animals.

"Flushing" refers to a transient erythema or redness of the skin, together with a sensation of warmth or burning, typically over the face and/or neck and less frequently on the upper trunk and abdomen. A flush is usually temporary and is caused by medications or other substances that cause widening of the capillaries, such as niacin. A more detailed description of flushing can be found in Champion R. H., et al, eds. Rook/Wilkinson/Ebling Textbook of Dermatology, 6th ed., vol. 3., Oxford, UK: Blackwell Scientific, 1998; "Flushing and Flushing Syndromes, Rosacea and Perioral Dermatitis", pp. 2099-2104.

"Halogen" refers to a fluoro, chloro, bromo, or iodo group. In certain embodiments, halogen refers to a chloro group.

"Heteroalkyl" by itself or as part of another substituent refers to an alkyl group in which one or more of the carbon atoms (and certain associated hydrogen atoms) are independently replaced with the same or different heteroatomic groups. Examples of heteroatomic groups include, but are not limited to, —O—, —S—, —O—O—, —S—S—, —O—S—, —NR$^{13}$, =N—N=, —N=N—, —N=N—NR$^{13}$—, —PR$^{13}$—, —P(O)$_2$—, —POR$^{13}$—, —O—P(O)$_2$—, —SO—, —SO$_2$—, —Sn(R$^{13}$)$_2$—, and the like, where each R$^{13}$ is independently chosen from hydrogen, $C_{1-6}$ alkyl, substituted $C_{1-6}$ alkyl, $C_{6-12}$ aryl, substituted $C_{6-12}$ aryl, $C_{7-18}$ arylalkyl, substituted $C_{7-18}$ arylalkyl, $C_{3-7}$ cycloalkyl, substituted $C_{3-7}$ cycloalkyl, $C_{3-7}$ heterocycloalkyl, substituted $C_{3-7}$ heterocycloalkyl, $C_{1-6}$ heteroalkyl, substituted $C_{1-6}$ heteroalkyl, $C_{6-12}$ heteroaryl, substituted $C_{6-12}$ heteroaryl, $C_{7-18}$ heteroarylalkyl, or substituted $C_{7-18}$ heteroarylalkyl. Reference to, for example, a $C_{1-6}$ heteroalkyl, means a $C_{1-6}$ alkyl group in which at least one of the carbon atoms (and certain associated hydrogen atoms) is replaced with a heteroatom. For example $C_{1-6}$ heteroalkyl includes groups having five carbon atoms and one heteroatom, groups having four carbon atoms and two heteroatoms, etc. In certain embodiments, each R$^{13}$ is independently chosen from hydrogen and $C_{1-3}$ alkyl. In certain embodiments, a heteroatomic group is chosen from —O—, —S—, —NH—, —N(CH$_3$)—, and —SO$_2$—; and in certain embodiments, the heteroatomic group is —O—.

"Heteroaryl" refers to a monovalent heteroaromatic radical derived by the removal of one hydrogen atom from a single atom of a parent heteroaromatic ring system. Heteroaryl encompasses multiple ring systems having at least one heteroaromatic ring fused to at least one other ring, which can be aromatic or non-aromatic. For example, heteroaryl encompasses bicyclic rings in which one ring is heteroaromatic and the second ring is a heterocycloalkyl ring. For such fused, bicyclic heteroaryl ring systems wherein only one of the rings contains one or more heteroatoms, the radical carbon may be at the aromatic ring or at the heterocycloalkyl ring. In certain embodiments, when the total number of N, S, and O atoms in the heteroaryl group exceeds one, the heteroatoms are not adjacent to one another. In certain embodiments, the total number of heteroatoms in the heteroaryl group is not more than two.

Examples of heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, thiazolidine, oxazolidine, and the like. In certain embodiments, a heteroaryl group is from 4- to 20-membered heteroaryl ($C_{4-20}$), and in certain embodiments from 4- to 12-membered heteroaryl ($C_{4-10}$). In certain embodiments, heteroaryl groups are those derived from thiophene, pyrrole, benzothiophene, benzofuran, indole, pyridine, quinoline, imidazole, oxazole, or pyrazine. For example, in certain embodiments, $C_5$ heteroaryl can be furyl, thienyl, pyrrolyl, imidazolyl, pyrazolyl, isothiazolyl, isoxazolyl.

"Heterocycloalkyl" refers to a saturated or unsaturated cyclic alkyl radical in which one or more carbon atoms (and certain associated hydrogen atoms) are independently replaced with the same or different heteroatom; or to a parent aromatic ring system in which one or more carbon atoms (and certain associated hydrogen atoms) are independently replaced with the same or different heteroatom such that the ring system no longer contains at least one aromatic ring. Examples of heteroatoms to replace the carbon atom(s) include, but are not limited to, N, P, O, S, Si, etc. Examples of heterocycloalkyl groups include, but are not limited to, groups derived from epoxides, azirines, thiiranes, imidazolidine, morpholine, piperazine, piperidine, pyrazolidine, pyrrolidine, quinuclidine, and the like. In certain embodiments, a heterocycloalkyl group is $C_{5-10}$ heterocycloalkyl, $C_{5-8}$ heterocycloalkyl, and in certain embodiments, $C_{5-6}$ heterocycloalkyl.

"Leaving group" has the meaning conventionally associated with it in synthetic organic chemistry, i.e., an atom or a group capable of being displaced by a nucleophile and includes halogen such as chloro, bromo, fluoro, and iodo, acyloxy (alkoxycarbonyl) such as acetoxy and benzoyloxy, aryloxycarbonyl, mesyloxy, tosyloxy, trifluoromethanesulfonyloxy, aryloxy such as 2,4-dinitrophenoxy, methoxy, N,O-dimethylhydroxyamino, p-nitrophenolate, imidazolyl, and the like.

"Monomethyl fumarate" refers to the monomethyl ester of fumaric acid. The compound has the formula HOOCCH=CHCOOCH$_3$, and has a molecular weight of 130.10 daltons. The compound is also commonly referred to as 2(E)-Butenedioic acid 1-methyl ester, (2E)-4-Methoxy-4-oxobut-2-enoic acid; Fumaric acid hydrogen 1-methyl ester; (2E)-2-Butenedioic acid 1-methyl ester; (E)-2-Butenedioic acid monomethyl ester; Monomethyl trans-ethylene-1,2-dicarboxylate; and methyl hydrogen fumarate. The compound is also referred to herein and elsewhere by the acronyms MMF and/or MHF.

"Parent aromatic ring system" refers to an unsaturated cyclic or polycyclic ring system having a conjugated π (pi) electron system. Included within the definition of "parent aromatic ring system" are fused ring systems in which one or more of the rings are aromatic and one or more of the rings are saturated or unsaturated, such as, for example, fluorene, indane, indene, phenalene, etc. Examples of parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like.

"Parent heteroaromatic ring system" refers to an aromatic ring system in which one or more carbon atoms (and any associated hydrogen atoms) are independently replaced with the same or different heteroatom in such a way as to maintain the continuous π-electron system characteristic of aromatic systems and a number of out-of-plane π-electrons corresponding to the Hückel rule (4n+2). Examples of heteroatoms to replace the carbon atoms include, but are not limited to, N, P, O, S, and Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Examples of parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, thiazolidine, oxazolidine, and the like.

"Patient" refers to a mammal, for example, a human.

"Pharmaceutically acceptable" refers to approved or approvable by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound, which possesses the desired pharmacological activity of the parent compound. Such salts include acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; and salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine, and the like. In certain embodiments, a pharmaceutically acceptable salt is the hydrochloride salt. In certain embodiments, a pharmaceutically acceptable salt is the sodium salt.

"Pharmaceutically acceptable vehicle" refers to a pharmaceutically acceptable diluent, a pharmaceutically acceptable adjuvant, a pharmaceutically acceptable excipient, a pharmaceutically acceptable carrier, or a combination of any of the foregoing with which a compound provided by the present disclosure may be administered to a patient and which does not destroy the pharmacological activity thereof and which is non-toxic when administered in doses sufficient to provide a therapeutically effective amount of the compound.

"Pharmaceutical composition" refers to a compound selected from monomethyl fumarate, or a prodrug of monomethyl fumarate such as dimethyl fumarate or a compound of Formulae (I)-(IV), and at least one pharmaceutically acceptable vehicle, with which the compound is administered to a patient.

"Substituted" refers to a group in which one or more hydrogen atoms are independently replaced with the same or different substituent group(s). In certain embodiments, each substituent group is independently chosen from halogen, —OH, —CN, —CF$_3$, =O, —NO$_2$, benzyl, —C(O)NH$_2$, —R$^{11}$, —OR$^{11}$, —C(O)R$^{11}$, —COOR$^{11}$, and —NR$^{11}{}_2$ wherein each R$^{11}$ is independently chosen from hydrogen and C$_{1-4}$ alkyl. In certain embodiments, each substituent group is independently chosen from halogen, —OH, —CN, —CF$_3$, —NO$_2$, benzyl, —R$^{11}$, —OR$^{11}$, and —NR$^{11}{}_2$ wherein each R$^{11}$ is independently chosen from hydrogen and C$_{1-4}$ alkyl. In certain embodiments, each substituent group is independently chosen from halogen, —OH, —CN, —CF$_3$, =O, —NO$_2$, benzyl, —C(O)NR$^{11}{}_2$, —R$^{11}$, —OR$^{11}$, —C(O)R$^{11}$, —COOR$^{11}$, and —NR$^{11}{}_2$ wherein each R$^{11}$ is independently chosen from hydrogen and C$_{1-4}$ alkyl. In certain embodiments, each substituent group is independently chosen from —OH, C$_{1-4}$ alkyl, and —NH$_2$.

"Systemic administration" and "systemically administering" shall each mean a route of administration of a compound (as defined herein) into the circulatory system of a patient in a therapeutically effective amount (as defined herein). In some non-limiting embodiments, administration can take place via enteral administration (absorption of the medication through the gastrointestinal tract) or parenteral administration (generally injection, infusion, or implantation). These terms are in contrast with topical and other types of local administration where a therapeutically effective amount is not in the circulatory system. In some embodiments, systemic administration is oral administration. In some embodiments, systemic administration is parenteral administration by injection.

"Treating" or "treatment" of any disease refers to reversing, alleviating, arresting, or ameliorating a disease or at least one of the clinical symptoms of a disease, reducing the risk of acquiring at least one of the clinical symptoms of a disease, inhibiting the progress of a disease or at least one of the clinical symptoms of the disease or reducing the risk of developing at least one of the clinical symptoms of a disease. "Treating" or "treatment" also refers to inhibiting the disease, either physically, (e.g., stabilization of a discernible symptom), physiologically, (e.g., stabilization of a physical parameter), or both, and to inhibiting at least one physical parameter that may or may not be discernible to the patient. In certain embodiments, "treating" or "treatment" refers to protecting against or delaying the onset of at least one or more symptoms of a disease in a patient.

"Therapeutically effective amount" refers to the amount of a compound that, when administered to a subject for treating a disease, or at least one of the clinical symptoms of a disease, is sufficient to affect such treatment of the disease or symptom thereof. The "therapeutically effective amount" may vary depending, for example, on the compound, the disease and/or symptoms of the disease, severity of the disease and/or symptoms of the disease or disorder, the age, weight, and/or health of the patient to be treated, and the judgment of the prescribing physician. An appropriate amount in any given instance may be ascertained by those skilled in the art or capable of determination by routine experimentation.

"Therapeutically effective dose" refers to a dose that provides effective treatment of a disease or disorder in a patient. A therapeutically effective dose may vary from compound to compound, and from patient to patient, and may depend upon factors such as the condition of the patient and the route of delivery. A therapeutically effective dose may be determined in accordance with routine pharmacological procedures known to those skilled in the art.

"Average Cmax" refers to the average of two or more individual Cmax values determined across a group of multiple subjects. For example, if multiple subjects are dosed as described herein they can each have a different individual Cmax value. The calculated mean of these different Cmax values is the "Average Cmax" for the group.

"Maximum Average Concentration" refers to the observed Cmax of an average plot of MMF concentration versus time for a group of subjects, constructed as a single curve using the calculated average MMF concentration across all subjects at each time point. For example, if a group comprising multiple subjects is dosed as described herein each subject can each have different MMF concentrations at any given time point. The observed Cmax value obtained from the single curve constructed by plotting the average concentration values at each time point is the "Maximum Average Concentration". The "Maximum Average Concentration" value may not be the same as the "Average Cmax" value for the same group of individuals.

"Average maximum rate of rise" refers to the average of all of the individual maximum rates of rise determined across all subjects.

DETAILED DESCRIPTION

Reference is now made in detail to certain embodiments of the methods for reducing flushing in patients during administration of a compound selected from: (i) monomethyl fumarate, (ii) a prodrug of monomethyl fumarate, and/or (iii) a combination thereof. The disclosed embodiments are not intended to be limiting of the claims. To the contrary, the claims are intended to cover all alternatives, modifications, and equivalents.

Methods

In Vitro Measurement of MMF or MMF Prodrug Release from a Dosage Form

A 2-stage dissolution test in which the dosage form to be tested is first placed in a low pH solution for 2 hours, followed by placement in a near neutral pH solution for the remainder of the test period. This dissolution test is used to better approximate the pH conditions experienced by a dosage form after swallowing by a patient, i.e., low pH of the stomach followed by near neutral pH of the intestines. The dosage forms are first placed into a dissolution vessel (USP, Type I, basket) containing 750 mL of 0.1 N hydrochloric acid (pH 1.2). After 2 hours, 250 mL of 200 mM tribasic sodium phosphate is added to the vessel resulting in a pH adjustment from 1.2 to 6.8. The dissolution medium is kept at 37° C. and is agitated at 100 rpm. Samples are taken at each sampling time point and analyzed by reverse phase HPLC using a C18 column for the compound being tested. The HPLC parameters are set as follows: a 7 minute gradient method according to Table 4 (Example 2) where Mobile Phase A is water/0.1% $H_3PO_4$ and Mobile Phase B is water/acetonitrile/$H_3PO_4$ (10/90/0.1 by volume) with UV detection at 210 nm.

Individual patients exhibit varying susceptabilities to flushing caused by exposure to MMF. Thus, at identical MMF exposures, certain patients exhibit no flushing while other patients exhibit flushing. For this reason, in the present context, a reduction of flushing is intended to denote a decrease in the incidence/frequency among a given treated patient population of flushing observed after administration of the compound(s) according to the disclosures herein. The incidence/frequency of flushing observed after administration of the same compound(s) but at pharmacokinetic parameters (i.e., Cmax and slopes of the MMF blood plasma concentration versus time curves) exceeding those set forth herein is used as the basis for comparison. The incidence/frequency of flushing in a patient population can be measured, e.g., as described by O'toole et al. Cancer 2000, 88(4), 770-776. Typically, the incidence/frequency of flushing is measured and expressed as the percentage of patients within a test group who experience flushing.

In the context of treating multiple sclerosis by systemically administering MMF and/or an MMF prodrug, the only reported incidences of flushing reported to date have been in connection with the clinical testing of Biogen Idec's BG-12 product, which is a delayed release (i.e., enteric coated microtablets) oral dosage form of the MMF prodrug dimethyl fumarate; see, e.g., Sheikh et al., Safety Tolerability and Pharmacokinetics of BG-12 Administered with and without Aspirin, Key Findings from a Randomized, Double-blind, Placebo-controlled Trial in Healthy Volunteers, Poster PO4.136 presented at the 64$^{th}$ Annual Meeting of the American Academy of Neurology, Apr. 21-28, 2012, New Orleans, La.; Dawson et al., Bioequivalence of BG-12 (Dimethyl Fumarate) Administered as a Single 240 mg Capsule and Two 120 mg Capsules: Findings from a Randomized, Two-period Crossover Study, Poster P913 presented at the 28th Congress of the European Committee for Treatment and Research in Multiple Sclerosis, Oct. 10-13, 2012, Lyon, France; and Woodworth et al., Pharmacokinetics of Oral BG-12 Alone Compared with BG-12 and Interferon β-1a or Glatiramer Acetate Administered Together, Studied in Health Volunteers, Poster PO4.207 presented at the 62$^{nd}$ Annual Meeting of the American Academy of Neurology, Apr. 10-17, 2010, Toronto, Ontario, Canada. In these publications, Sheikh reported flushing incidences of 83% and 100% for patients taking BG-12 only, BID and TID, respectively; Dawson reported flushing incidences of 84% and 86% for two different BG-12 dosage forms; and Woodward reported flushing incidences of 50% and 76% in treatment groups receiving BG-12 alone. Thus, the reported incidences of flushing in patients taking BG-12 averages to 80% across multiple patient populations.

In one aspect, in the context of systemic treatment of multiple sclerosis by systemic administration of MMF and/or an MMF prodrug, a reduction in flushing according to the methods disclosed herein is construed as a flushing incidence of less than 50% of a treated patient population. In another aspect, the incidence of flushing is less than 40% of a treated patient population. In another aspect the incidence of flushing is less than 30% of a treated patient population. The reduction of flushing incidence/frequency, as described above, can be monitored in a clinical trial setting.

In the context of treating psoriasis by systemically administering MMF and/or an MMF prodrug, the only reported incidences of flushing published to date have been in connection with the clinical testing of Fumapharm's Fumaderm product, which is a delayed release (i.e., enteric coated tablet) oral dosage form of the MMF prodrug dimethyl fumarate together with several different salts of monoethyl fumarate. Monoethyl fumarate and salts thereof are not MMF prodrugs. Mrowietz et al. (Treatment of Psoriasis with Fumaric Acid Esters: Results of a prospective Multicenter Study, *British Journal of Dermatology*, 1998, 138(3), 456-460) report flushing incidence of 31%. Other reported flushing incidence in psoriasis patients taking Fumaderm of about 30% and one-third of patients are common.

In one aspect, in the context of systemic treatment of psoriasis by systemic administration of MMF and/or an MMF prodrug, a reduction in flushing according to the methods disclosed herein is construed as a flushing incidence of less than 20% of a treated patient population. In another aspect, the incidence of flushing is less than 15% of a treated patient population. In another aspect the incidence of flushing is less than 10% of a treated patient population. The reduction of flushing incidence/frequency, as described above, can be monitored in a clinical trial setting.

In accordance with a first aspect of the presently disclosed treatment methods, the MMF and/or MMF prodrug is systemically administered in therapeutic amounts using a dosage form and a dosing frequency that achieves across a population of patients receiving said treatment a maximum average concentration, as defined herein, of monomethyl fumarate in the blood plasma of the patients of less than 500 ng/ml. In one embodiment, the maximum average concentration of monomethyl fumarate in the blood plasma of the patients is less than 400 ng/ml. In another embodiment, the maximum average concentration of monomethyl fumarate in the blood plasma of the patients is less than 350 ng/ml. In yet another embodiment, the maximum average concentration of monomethyl fumarate in the blood plasma of the patients is less than 300 ng/ml. In yet another embodiment, the maximum average concentration of monomethyl fumarate in the blood plasma of the patients is less than 250 ng/ml. In yet another embodiment, the maximum average concentration of monomethyl fumarate in the blood plasma of the patients is less than 200 ng/ml. In yet another embodiment, the maximum average concentration of monomethyl fumarate in the blood plasma of the patients is less than 150 ng/ml. In yet another embodiment, the maximum average concentration of monomethyl fumarate in the blood plasma of the patients is less than 100 ng/ml.

In another aspect, the average Cmax, as defined herein, of monomethyl fumarate in the blood plasma of the patients is less than 1100 ng/ml. In certain aspects, the average Cmax of monomethyl fumarate in the blood plasma of the patients is maintained at less than 600 ng/ml. In yet another aspect, the average Cmax of monomethyl fumarate in the blood plasma of the patients is maintained at less than 500 ng/ml. In yet another aspect, the average Cmax of monomethyl fumarate in the blood plasma of the patients is maintained at less than 400 ng/ml. In yet another aspect, the average Cmax of monomethyl fumarate in the blood plasma of the patients is maintained at less than 300 ng/ml. In yet another aspect, the average Cmax of monomethyl fumarate in the blood plasma of the patients is maintained at less than 200 ng/ml. In yet another aspect, the average Cmax of monomethyl fumarate in the blood plasma of the patients is maintained at less than 100 ng/ml.

Figure 13:
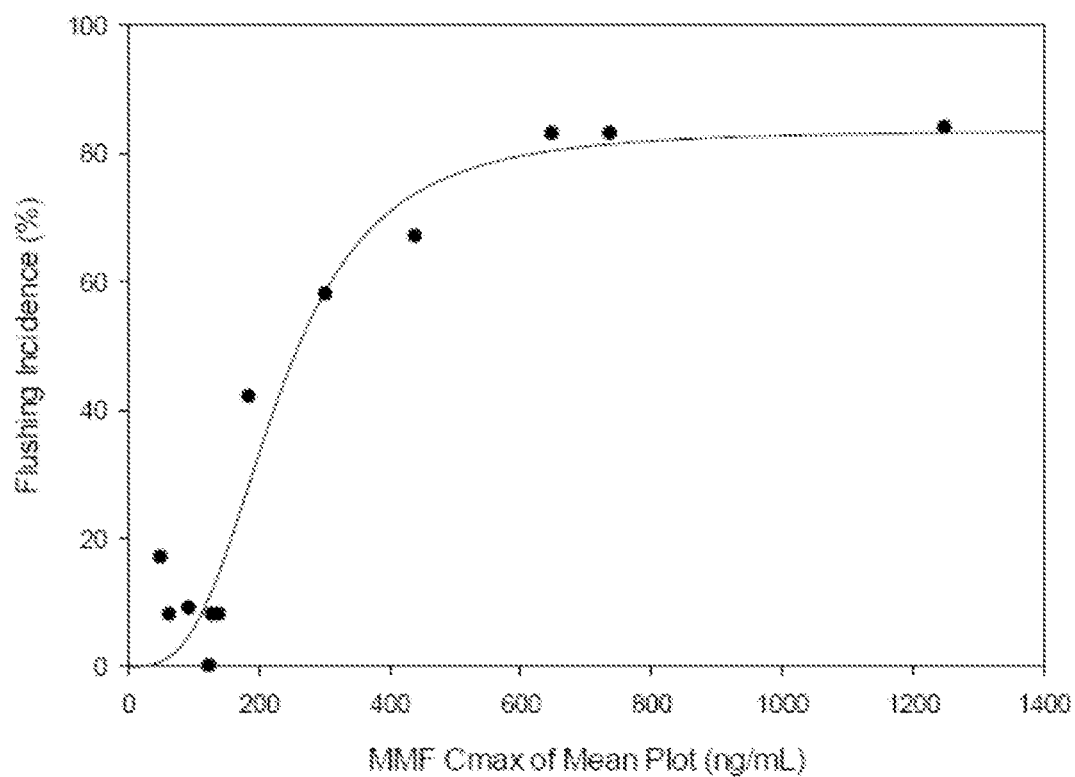
FIG. 13 shows the % flushing incidences as a function of mean MMF Cmax (maximum average concentration) (ng/mL) over patient populations for DMF and Compound 1 (a prodrug of MMF).
Figure 14:
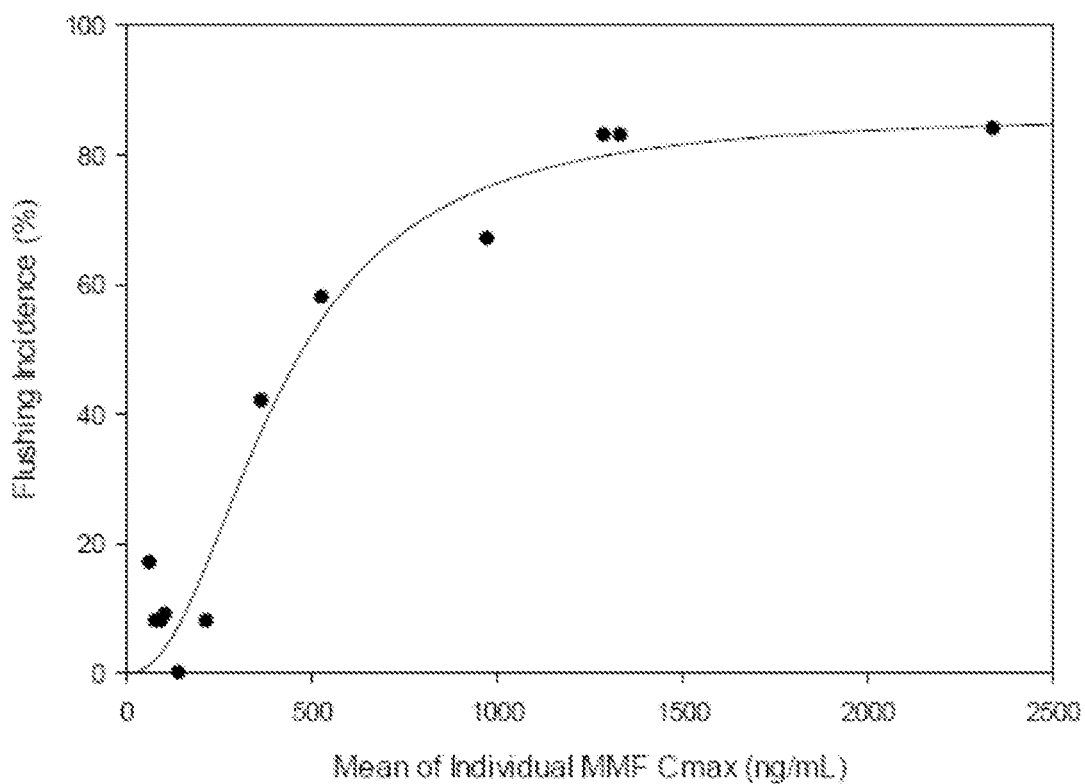
FIG. 14 shows the % flushing incidences as a function of mean of individual MMF Cmax (average Cmax) (ng/mL) for DMF and Compound 1 (a prodrug of MMF).

The following table and FIGS. 13-14 show flushing incidence as a function of MMF Cmax (maximum average concentration and average Cmax) over patient populations for DMF and an MMF prodrug of Formula (II). The curves in the figures were fitted using a Hill $E_{max}$ model.

TABLE 1

Flushing Incidence as a Function of MMF Cmax

| Source | Compound, Formulation*, Dose (mg) and fed or fasted | mg-eq of MMF dosed | Dosing Frequency/ Dose Interval (hrs) | MMF Cmax of Mean Plot** (ng/mL) | Mean of Individual MMF Cmax*** (ng/mL) | Flushing Incidence (%) |
|---|---|---|---|---|---|---|
| Dawson+ | DMF, BG-12, 240, fasted | 218 | BID/12 | 1250 | 2340 | 84 |
| Sheikh+ | DMF, BG-12, 240, fed | 218 | BID/12 | 738 | 1335 | 83 |
| Study 1 | Compound (1)++ Formulation 1, 400, fasted | 212 | BID/12 | 649 | 1290 | 83 |
| Study 2 | Compound (1), Formulation 1, 200, fasted | 106 | Single Dose | 439 | 975 | 67 |
| Study 2 | Compound (1), Formulation 1, 200, fasted | 106 | Single Dose | 302 | 529 | 58 |
| Study 2 | Compound (1), Formulation 1, 200, fed | 106 | Single Dose | 185 | 366 | 42 |
| Study 2 | Compound (1), Formulation 2, 200, fed | 106 | Single Dose | 139 | 217 | 8 |
| Study 2 | Compound (1), Formulation 3, 200, fasted | 106 | Single Dose | 129 | 95 | 8 |
| Study 2 | Compound (1), Formulation 2, 200, fasted | 106 | Single Dose | 124 | 143 | 0 |
| Study 2 | Compound (1), Formulation 4, 200, fed | 106 | Single Dose | 93 | 106 | 9 |
| Study 2 | Compound (1), Formulation 3, 200, fed | 106 | Single Dose | 63 | 80 | 8 |
| Study 2 | Compound (1), Formulation 4, 200, fast | 106 | Single Dose | 50 | 64 | 17 |

*Formulation 2 is the dosage form described in Example 10; Formulation 3 is the dosage form described in Example 3; Formulation 4 is the dosage form described in Example 5;
**maximum average Concentration;
***average Cmax;
+Poster (see above);
++Compound (1) referred to in the above table is an MMF prodrug of Formula (II); (N,N-Diethylcarbamoyl)methyl methyl (2E)but-2-ene-1,4-dioate having the following chemical structure:

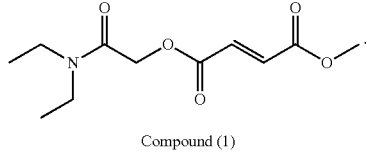 [SMILES: CCN(CC)C(=O)COC(=O)/C=C/C(=O)OC]

Compound (1)

The fifth column of the above table lists the values of MMF Cmax of the mean plot (maximum average concentration) in decreasing order. As shown in Table 1, as the mean MMF Cmax (maximum average concentration) drops from 649 to 439 ng/ml, the flushing incidence drops below the rates reported previously in the literature for the BG-12 DMF product. The sixth column of the above table lists the corresponding mean of individual MMF Cmax (Average Cmax) values. As shown in Table 1, as the mean MMF Cmax (Average Cmax) drops below 1100 ng/ml, the flushing incidence drops below the rates reported previously in the literature for the BG-12 DMF product.

In accordance with a second aspect of the presently disclosed treatment methods, the MMF and/or MMF prodrug is systemically administered in therapeutic amounts using a dosage form and a dosing frequency that achieves across a population of patients receiving said treatment an average maximum rate of rise in MMF concentration in the blood plasma of the patients of less than 0.25 wt % ng-eq of MMF dosed/ml/hr. In one embodiment, the average maximum rate of rise in MMF concentration in the blood plasma of the patients is less than 0.20 wt % ng-eq of MMF dosed/ml/hr. In another embodiment, the average maximum rate of rise in MMF concentration in the blood plasma of the patients is less than 0.15 wt % ng-eq of MMF dosed/ml/hr. In yet another embodiment, the average maximum rate of rise in MMF concentration in the blood plasma of the patients is less than 0.10 wt % ng-eq of MMF dosed/ml/hr.

In one embodiment, the methods comprise controlling administration of the compound(s) to the patient to achieve across a population of patients receiving said controlled administration of compound(s), an average maximum rate of rise in monomethyl fumarate concentration in the blood plasma of the patients of less than 0.25 wt % ng-eq of MMF dosed/ml/hr, and an average monomethyl fumarate concentration in the blood plasma of the patients, measured at a time of said maximum rate of rise, of less than 200 ng/ml. In another embodiment, the average maximum rate of rise in monomethyl fumarate concentration in the blood plasma of the patients is less than 0.15 wt % ng-eq of MMF dosed/ml/hr, and an average monomethyl fumarate concentration in the blood plasma of the patients, measured at a time of said maximum rate of rise, is less than 180 ng/ml. In yet another embodiment, the average maximum rate of rise in monomethyl fumarate concentration in the blood plasma of the patients is less than 0.10 wt % ng-eq of MMF dosed/ml/hr, and an average monomethyl fumarate concentration in the blood plasma of the patients, measured at a time of said maximum rate of rise, is less than 140 ng/ml.

Figure 15:
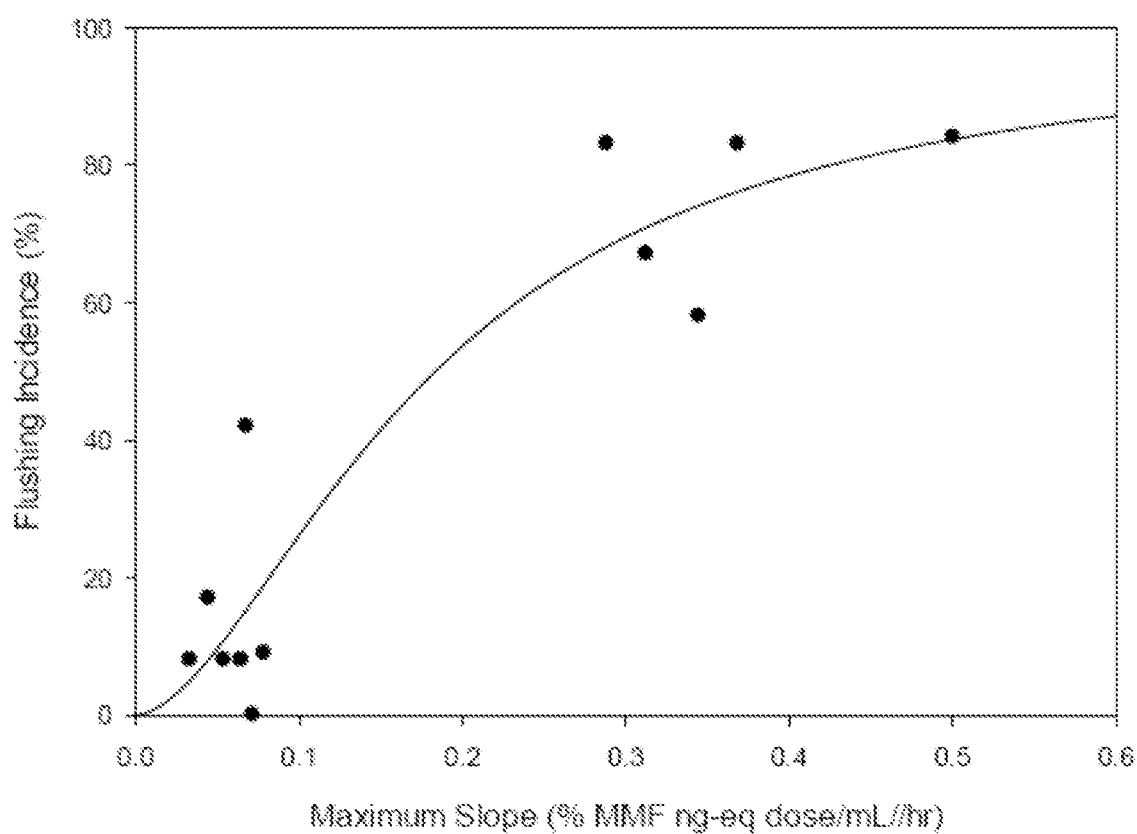
FIG. 15 shows the % flushing incidences as a function of maximum MMF slope (% MMF ng-eq dose/mL/hr) for DMF and Compound 1 (a prodrug of MMF).
Figure 16:
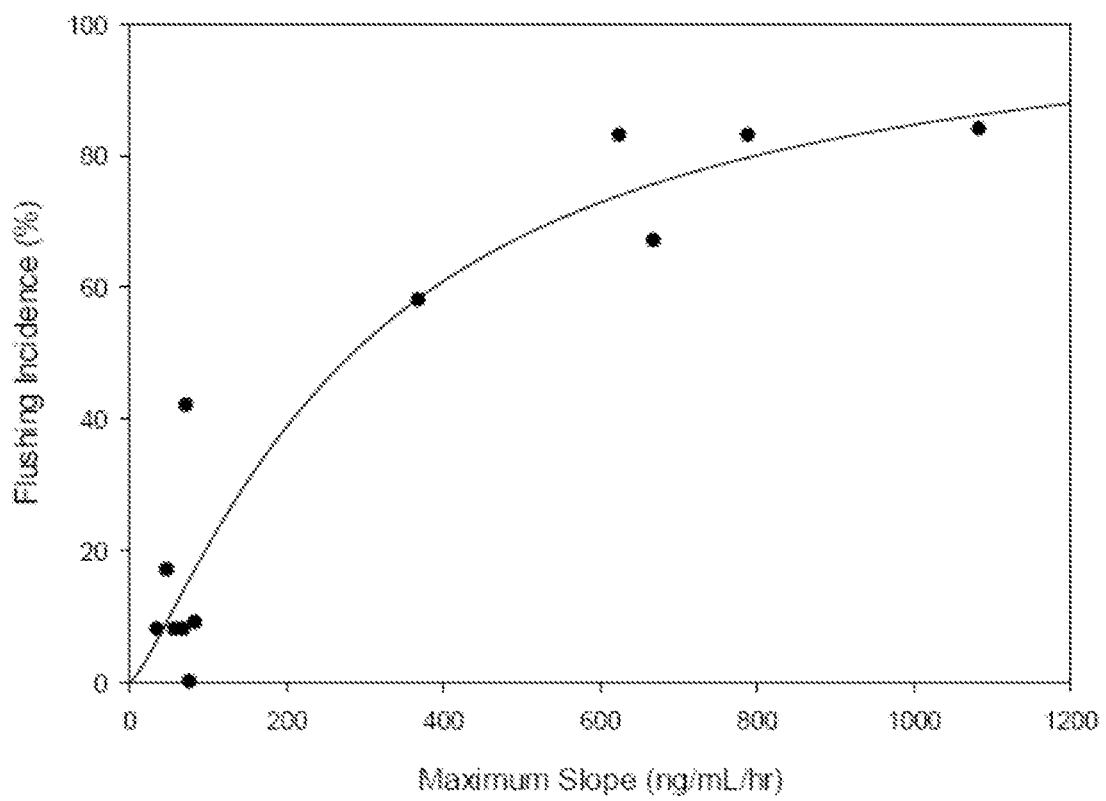
FIG. 16 shows the % flushing incidences as a function of maximum MMF slope (ng/mL/hr) for DMF and Compound 1 (a prodrug of MMF).

The maximum slope values (% dose and ng) for different dosage treatments are given in Table 2. The FIGS. 15-16 show plots of maximum MMF slope vs flushing incidence. The curves in the figures were fitted using a Hill $E_{max}$ model.

TABLE 2

| Source | Compound, Formulation*, Dose (mg), food | Max Slope % dose/mL/h | Max slope (ng/mL/hr) | Flushing Incidence (%) |
|---|---|---|---|---|
| Dawson | DMF, BG-12, 240 mg, fed | 0.5005 | 1084.3 | 84 |
| Sheikh | DMF, BG-12, 240 mg, fed | 0.2885 | 625.0 | 83 |
| Study 1 | Compound (1), Compound (1), Formulation 1 400 mg fast | 0.3689 | 789.1 | 83 |
| Study 1 | Compound (1), Formulation 1 200 mg fast | 0.3128 | 669.2 | 67 |
| Study 2 | Compound (1), Formulation 1 200 mg fast | 0.3448 | 368.9 | 58 |

TABLE 2-continued

| Source | Compound, Formulation*, Dose (mg), food | Max Slope % dose/mL/h | Max slope (ng/mL/hr) | Flushing Incidence (%) |
|---|---|---|---|---|
| Study 2 | Compound (1), Formulation 1 200 mg fed | 0.0680 | 72.7 | 42 |
| Study 2 | Compound (1), Formulation 2 200 mg fed | 0.0647 | 69.3 | 8 |
| Study 2 | Compound (1), Formulation 2 200 mg fast | 0.0718 | 76.8 | 0 |
| Study 2 | Compound (1), Formulation 3 200 mg fast | 0.0542 | 57.9 | 8 |
| Study 2 | Compound (1), Formulation 3 200 mg fed | 0.0334 | 35.7 | 8 |
| Study 2 | Compound (1), Formulation 4 200 mg fast | 0.0448 | 47.9 | 17 |
| Study 2 | Compound (1), Formulation 4 200 mg fed | 0.0787 | 84.2 | 9 |

*Formulation 2 is the dosage form described in Example 10; Formulation 3 is the dosage form described in Example 3; Formulation 4 is the dosage form described in Example 5.

In order to achieve the pharmacokinetic values of (i) a maximum average concentration of monomethyl fumarate in the blood plasma of the patients of less than 500 ng/ml, and/or (ii) an average maximum rate of rise in MMF concentration in the blood plasma of the patients of less than 0.25 wt % ng-eq of MMF dosed/ml/hr, it is necessary to control the introduction of MMF and/or MMF prodrug into the patients' bloodstream. For systemic oral delivery, this generally means an oral sustained release dosage form. While sustained and delayed-sustained release dosage forms of MMF prodrugs of Formula I, and most typically sustained release dosage forms of DMF, have been disclosed in the literature for reducing flushing, we have discovered that such dosage forms in fact offer little improvement in reducing patient flushing, either because they achieve too high of a maximum average concentration of monomethyl fumarate in the blood plasma of the patients, and/or too high of an average maximum rate of rise in MMF concentration in the blood plasma of the patients. Specifically, Nilsson et al. in US Patent Publication Nos. 2012/0034274 and 2012/0034303 disclose oral sustained release and oral delayed sustained release dosage forms of DMF, the latter dosage forms being enteric coated. Although the Nilsson dosage forms purport to reduce the incidence of flushing in patients, they present their flushing incidence as a percentage of the patients who flush upon administration of Fumaderm which contains DMF as a primary active ingredient (see Tables II in both Nilsson publications) and at least some of the reported reductions in the incidence of flushing (23% and 35% reductions compared to Fumaderm) may well be within the range of experimental error or variability within small patient populations. Of the many dosage forms disclosed in these two publications, the slowest DMF-releasing dosage forms are in Example 2 of US 2012/0034274 and Examples 16 and 23 of US 2012/0034303. The Example 2 dosage form is shown to release: (i) about 90% of the DMF dose over a period of 3 hours, (ii) about 43% of the DMF dose in the third hour of in vitro release, and (iii) about 65% of the DMF loading over the second and third hours of in vitro release. The Example 16 dosage form, which is enteric coated and therefore exhibits little to no release during the first 2 hours of the in vitro test at low pH conditions, is shown to release (i) about 90% of the DMF dose over a period of 3.5 hours marked from the start of the near-neutral pH portion of the test, and (ii) about 50-55% of its DMF loading over the second and third hours of in vitro release. The Example 23 dosage form is shown to release (i) about 90% of the DMF dose over a period of 4 hours, and (ii) about 65% of its DMF loading over the third and fourth hours of in vitro release. Thus, all of the Nilsson dosage forms release the majority (90%) of their DMF dose in periods of 4 hours or less, measured from the start of DMF release.

In contrast to the Nilsson et al. dosage forms, the dosage forms disclosed herein release MMF and/or MMF prodrug at a slower rate and over longer time periods than the Nilsson dosage forms. The oral dosage forms disclosed herein can be characterized as either enteric-coated, and therefore not designed to release much of the compound in the low pH environment of a patient's stomach, or non-enteric coated, in which release of compound in the stomach is not necessarily prohibited.

Thus, for oral enteric-coated dosage forms disclosed herein, the dosage forms contain a therapeutically effective dose of the MMF and/or MMF prodrug and are designed to be administered to each patient in a population of patients at a dosing frequency of not more than twice per day. The dosage forms, when subjected to the in vitro dissolution test employing pH 1.2 for the first 2 hours, and pH 6.8 thereafter, releases the dose of MMF and/or MMF prodrug as follows: (i) less than 10 wt % of the dose over the first 2 hours of the in vitro dissolution test; (ii) at least 90 wt % of the dose over not less than the first 8 hours of the in vitro dissolution test; (iii) no more than 30 wt % of the dose in any one hour during the in vitro dissolution test; and (iv) no more than 40 wt % of the dose in any consecutive two hours during the in vitro dissolution test.

For oral non-enteric-coated dosage forms disclosed herein, the dosage forms contain a therapeutically effective dose of the MMF and/or MMF prodrug and are designed to be administered to each patient in a population of patients at a dosing frequency of not more than twice per day. The dosage forms, when subjected to the in vitro dissolution test employing pH 1.2 for the first 2 hours, and pH 6.8 thereafter, releases the dose of MMF and/or MMF prodrug as follows: (i) at least 90 wt % of the dose over not less than the first 8 hours of the in vitro dissolution test; (ii) no more than 30 wt % of the dose in any one hour during the in vitro dissolution test; and (iii) no more than 40 wt % of the dose in any consecutive two hours during the in vitro dissolution test.

Suitable sustained release oral dosage forms that achieve the above described in vitro release profiles are disclosed in Examples 1 and 3 (enteric-coated sustained release tablets), 5 (enteric-coated pellets in a Vcaps plus capsule) and 8-15 (non-enteric-coated, compression coated tablets) herein.

Compounds

Certain embodiments of the methods disclosed herein utilize a compound of Formula (I):

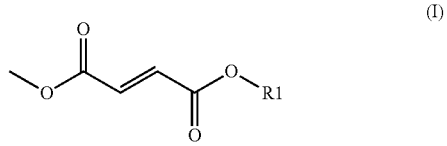

(I)

or a pharmaceutically acceptable salt thereof, wherein $R^1$ is chosen from a $C_1$ to $C_6$ alkyl.

In certain embodiments, $R^1$ is $C_2$ to $C_6$ alkyl.

In certain embodiments, $R^1$ is methyl.

In certain embodiments, $R^1$ is ethyl, n-propyl, isopropyl, n-butyl, isobutyl, tert-butyl, n-pentyl, pentyl-2-yl, 2-methylbutyl, isopentyl, 3-methylbutan-2-yl, neopentyl, tert-pentyl, n-hexyl, hexan-2-yl, 2-methylpentyl, 3-methylpentyl, 4-methylpentyl, 3-methylpentan-2-yl, 4-methylpentan-2-yl, 2,3-dimethylbutyl, or 3,3-dimethylbutyl.

Examples of compounds of Formula (I) include dimethylfumarate, diethylfumarate, dipropylfumarate, dibutylfumarate, dipentylfumarate, methyl-ethylfumarate, methyl-propylfumarate, methyl-butylfumarate, methyl-pentylfumarate, monoethylfumarate, monopropylfumarate, monobutylfumarate and monopentylfumarate, and/or pharmaceutically acceptable salts of any of the foregoing. In certain embodiments, the compounds of Formula (I) include dimethyl fumarate, methyl ethyl fumarate, methyl n-propyl fumarate and methyl i-propyl fumarate, including pharmaceutically acceptable salts thereof. Pharmaceutically acceptable salts thereof comprise metal salts, such as a salt selected from alkali metal salts and alkaline earth metal salts including sodium, potassium, calcium, magnesium, strontium or zinc salts, amino acid salts etc.

Certain embodiments of the methods disclosed herein utilize a compound of Formula (II):

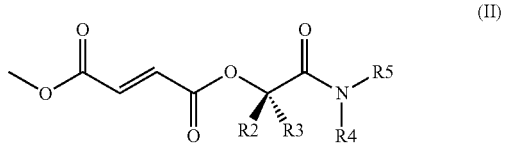

(II)

or a pharmaceutically acceptable salt thereof, wherein:

$R^2$ and $R^3$ are independently chosen from hydrogen, $C_{1-6}$ alkyl, and substituted $C_{1-6}$ alkyl;

$R^4$ and $R^5$ are independently chosen from hydrogen, $C_{1-6}$ alkyl, substituted $C_{1-6}$ alkyl, $C_{1-6}$ alkoxy, substituted $C_{1-6}$ alkoxy, $C_{1-6}$ alkoxycarbonyl, substituted $C_{1-6}$ alkoxycarbonyl, $C_{1-6}$ heteroalkyl, substituted $C_{1-6}$ heteroalkyl, $C_{4-12}$ cycloalkylalkyl, substituted $C_{4-12}$ cycloalkylalkyl, $C_{7-12}$ arylalkyl, and substituted $C_{7-12}$ arylalkyl; or $R^4$ and $R^5$ together with the nitrogen to which they are bonded form a ring chosen from a $C_{5-10}$ heteroaryl, substituted $C_{5-10}$ heteroaryl, $C_{5-10}$ heterocycloalkyl, and substituted $C_{5-10}$ heterocycloalkyl; and wherein each substituent group is independently chosen from halogen, —OH, —CN, —CF$_3$, =O, —NO$_2$, benzyl, —C(O)NR$^{11}{}_2$, —R$^{11}$, —OR$^{11}$, —C(O)R$^{11}$, —COOR$^{11}$, and —NR$^{11}{}_2$ wherein each R$^{11}$ is independently chosen from hydrogen and $C_{1-4}$ alkyl.

In certain embodiments of a compound of Formula (II), each substituent group is independently chosen from halogen, —OH, —CN, —CF$_3$, —R$^{11}$, —OR$^{11}$, and —NR$^{11}{}_2$ wherein each R$^{11}$ is independently chosen from hydrogen and $C_{1-4}$ alkyl. In certain embodiments, each substituent group is independently chosen from —OH, and —COOH.

In certain embodiments of a compound of Formula (II), each substituent group is independently chosen from =O, $C_{1-4}$ alkyl, and —COOR$^{11}$ wherein R$^{11}$ is chosen from hydrogen and $C_{1-4}$ alkyl.

In certain embodiments of a compound of Formula (II), each of $R^2$ and $R^3$ is hydrogen.

In certain embodiments of a compound of Formula (II), one of $R^2$ and $R^3$ is hydrogen and the other of $R^2$ and $R^3$ is $C_{1-4}$ alkyl.

In certain embodiments of a compound of Formula (II), one of $R^2$ and $R^3$ is hydrogen and the other of $R^2$ and $R^3$ is chosen from methyl, ethyl, n-propyl, isopropyl, n-butyl, isobutyl, sec-butyl, and tert-butyl.

In certain embodiments of a compound of Formula (II), one of $R^2$ and $R^3$ is hydrogen and the other of $R^2$ and $R^3$ is methyl.

In certain embodiments of a compound of Formula (II), $R^4$ and $R^5$ are independently chosen from hydrogen and $C_{1-6}$ alkyl.

In certain embodiments of a compound of Formula (II), $R^4$ and $R^5$ are independently chosen from hydrogen and $C_{1-4}$ alkyl.

In certain embodiments of a compound of Formula (II), $R^4$ and $R^5$ are independently chosen from hydrogen, methyl, and ethyl.

In certain embodiments of a compound of Formula (II), each of $R^4$ and $R^5$ is hydrogen; in certain embodiments, each of $R^4$ and $R^5$ is methyl; and in certain embodiments, each of $R^4$ and $R^5$ is ethyl.

In certain embodiments of a compound of Formula (II), $R^4$ is hydrogen; and $R^5$ is chosen from $C_{1-4}$ alkyl, substituted $C_{1-4}$ alkyl wherein the substituent group is chosen from =O, —OR$^{11}$, —COOR$^{11}$, and —NR$^{11}{}_2$, wherein each R$^{11}$ is independently chosen form hydrogen and $C_{1-4}$ alkyl.

In certain embodiments of a compound of Formula (II), $R^4$ is hydrogen; and $R^5$ is chosen from $C_{1-4}$ alkyl, benzyl, 2-methoxyethyl, carboxymethyl, carboxypropyl, 1,3,4-thiadiazolyl, methoxy, 2-methoxycarbonyl, 2-oxo(1,3-oxazolidinyl), 2-(methylethoxy)ethyl, 2-ethoxyethyl, (tert-butyloxycarbonyl)methyl, (ethoxycarbonyl)methyl, carboxymethyl, (methylethyl)oxycarbonylmethyl, and ethoxycarbonylmethyl.

In certain embodiments of a compound of Formula (II), $R^4$ and $R^5$ together with the nitrogen to which they are bonded form a ring chosen from a $C_{5-6}$ heterocycloalkyl, substituted $C_{5-6}$ heterocycloalkyl, $C_{5-6}$ heteroaryl, and substituted $C_{5-6}$ heteroaryl ring. In certain embodiments of a compound of Formula (II), $R^4$ and $R^5$ together with the nitrogen to which they are bonded form a ring chosen from a $C_5$ heterocycloalkyl, substituted $C_5$ heterocycloalkyl, $C_5$ heteroaryl, and substituted $C_5$ heteroaryl ring. In certain embodiments of a compound of Formula (II), $R^4$ and $R^5$ together with the nitrogen to which they are bonded form a ring chosen from a $C_6$ heterocycloalkyl, substituted $C_6$ heterocycloalkyl, $C_6$ heteroaryl, and substituted $C_6$ heteroaryl ring. In certain embodiments of a compound of Formula (II), $R^4$ and $R^5$ together with the nitrogen to which they are bonded form a ring chosen from piperazine, 1,3-oxazolidinyl, pyrrolidine, and morpholine ring.

In certain embodiments of a compound of Formula (II), one of $R^2$ and $R^3$ is hydrogen and the other of $R^2$ and $R^3$ is $C_{1-6}$ alkyl; $R^4$ is hydrogen; and $R^5$ is chosen from hydrogen, $C_{1-6}$ alkyl, and benzyl.

In certain embodiments of a compound of Formula (II), one of $R^2$ and $R^3$ is hydrogen and the other of $R^2$ and $R^3$ is $C_{1-6}$ alkyl; $R^4$ is methyl; and $R^5$ is chosen from hydrogen, $C_{1-6}$ alkyl, and benzyl.

In certain embodiments of a compound of Formula (II), one of $R^2$ and $R^3$ is hydrogen and the other of $R^2$ and $R^3$ is chosen from hydrogen and $C_{1-6}$ alkyl; and each of $R^4$ and $R^5$ is $C_{1-6}$ alkyl.

In certain embodiments of a compound of Formula (II), one of $R^2$ and $R^3$ is hydrogen and the other of $R^2$ and $R^3$ is chosen from hydrogen and $C_{1-6}$ alkyl; and each of $R^4$ and $R^5$ is $C_{1-6}$ alkyl. In certain embodiments of a compound of Formula (II), each of $R^2$ and $R^3$ is hydrogen; and each of $R^4$ and $R^5$ is $C_{1-6}$ alkyl.

In certain embodiments of a compound of Formula (II), one of $R^2$ and $R^3$ is hydrogen and the other of $R^2$ and $R^3$ is chosen from hydrogen and $C_{1-4}$ alkyl; $R^4$ is hydrogen; and $R^5$ is chosen from $C_{1-4}$ alkyl and substituted $C_{1-4}$ alkyl, wherein the substituent group is chosen from =O, —OR$^{11}$, —COOR$^{11}$, and —NR$^{11}_2$, wherein each $R^{11}$ is independently chosen form hydrogen and $C_{1-4}$ alkyl. In certain embodiments of a compound of Formula (II), one of $R^2$ and $R^3$ is hydrogen and the other of $R^2$ and $R^3$ is methyl; $R^4$ is hydrogen; and $R^5$ is chosen from $C_{1-4}$ alkyl and substituted $C_{1-4}$ alkyl, wherein the substituent group is chosen from =O, —OR$^{11}$, —COOR$^{11}$, and —NR$^{11}_2$, wherein each $R^{11}$ is independently chosen form hydrogen and $C_{1-4}$ alkyl. In certain embodiments of a compound of Formula (II), each of $R^2$ and $R^3$ is hydrogen; $R^4$ is hydrogen; and $R^5$ is chosen from $C_{1-4}$ alkyl and substituted $C_{1-4}$ alkyl, wherein the substituent group is chosen from =O, —OR$^{11}$, —COOR$^{11}$, and —NR$^{11}_2$, wherein each $R^{11}$ is independently chosen form hydrogen and $C_{1-4}$ alkyl.

In certain embodiments of a compound of Formula (II), $R^4$ and $R^5$ together with the nitrogen to which they are bonded form a $C_{5-10}$ heterocycloalkyl ring.

In certain embodiments of a compound of Formula (II), one of $R^2$ and $R^3$ is hydrogen and the other of $R^2$ and $R^3$ is chosen from hydrogen and $C_{1-6}$ alkyl; and $R^4$ and $R^5$ together with the nitrogen to which they are bonded form a ring chosen from a $C_{5-6}$ heterocycloalkyl, substituted $C_{5-6}$ heterocycloalkyl, $C_{5-6}$ heteroaryl, and substituted $C_{5-6}$ heteroaryl ring. In certain embodiments of a compound of Formula (II), one of $R^2$ and $R^3$ is hydrogen and the other of $R^2$ and $R^3$ is methyl; and $R^4$ and $R^5$ together with the nitrogen to which they are bonded form a ring chosen from a $C_{5-6}$ heterocycloalkyl, substituted $C_{5-6}$ heterocycloalkyl, $C_{5-6}$ heteroaryl, and substituted $C_{5-6}$ heteroaryl ring. In certain embodiments of a compound of Formula (II), each of $R^2$ and $R^3$ is hydrogen; and $R^4$ and $R^5$ together with the nitrogen to which they are bonded form a ring chosen from a $C_{5-6}$ heterocycloalkyl, substituted $C_{5-6}$ heterocycloalkyl, $C_{5-6}$ heteroaryl, and substituted $C_{5-6}$ heteroaryl ring.

In certain embodiments of a compound of Formula (II), one of $R^2$ and $R^3$ is hydrogen and the other of $R^2$ and $R^3$ is chosen from hydrogen and $C_{1-6}$ alkyl; and $R^4$ and $R^5$ together with the nitrogen to which they are bonded form a ring chosen from morpholine, piperazine, and N-substituted piperazine.

In certain embodiments of a compound of Formula (II), one of $R^2$ and $R^3$ is hydrogen and the other of $R^2$ and $R^3$ is chosen from hydrogen and $C_{1-6}$ alkyl; and $R^4$ and $R^5$ together with the nitrogen to which they are bonded form a ring chosen from morpholine, piperazine, and N-substituted piperazine.

In certain embodiments of a compound of Formula (II), $R^2$ is hydrogen, and in certain embodiments, $R^3$ is hydrogen.

In certain embodiments of a compound of Formula (II), $R^4$ and $R^5$ are independently chosen from hydrogen, $C_{1-6}$ alkyl, substituted $C_{1-6}$ alkyl, $C_{6-10}$ aryl, substituted $C_{6-10}$ aryl, $C_{4-12}$ cycloalkylalkyl, substituted $C_{4-12}$ cycloalkylalkyl, $C_{7-12}$ arylalkyl, substituted $C_{7-12}$ arylalkyl, $C_{1-6}$ heteroalkyl, substituted $C_{1-6}$ heteroalkyl, $C_{6-10}$ heteroaryl, substituted $C_{6-10}$ heteroaryl, $C_{4-12}$ heterocycloalkylalkyl, substituted $C_{4-12}$ heterocycloalkylalkyl, $C_{7-12}$ heteroarylalkyl, substituted $C_{7-12}$ heteroarylalkyl; or $R^4$ and $R^5$ together with the nitrogen to which they are bonded form a ring chosen from a $C_{5-10}$ heteroaryl, substituted $C_{5-10}$ heteroaryl, $C_{5-10}$ heterocycloalkyl, and substituted $C_{5-10}$ heterocycloalkyl.

In certain embodiments, the Formula (II) compound is chosen from:

(N,N-diethylcarbamoyl)methyl methyl (2E)but-2-ene-1,4-dioate;
methyl[N-benzylcarbamoyl]methyl (2E)but-2-ene-1,4-dioate;
methyl 2-morpholin-4-yl-2-oxoethyl (2E)but-2-ene-1,4-dioate;
(N-butylcarbamoyl)methyl methyl (2E)but-2-ene-1,4-dioate;
[N-(2-methoxyethyl)carbamoyl]methyl methyl (2E)but-2-ene-1,4-dioate;
2-{2-[(2E)-3-(methoxycarbonyl)prop-2-enoyloxy]acetylamino}acetic acid;
4-{2-[(2E)-3-(methoxycarbonyl)prop-2-enoyloxy]acetylamino}butanoic acid;
methyl (N-(1,3,4-thiadiazol-2-yl)carbamoyl)methyl (2E)but-2-ene-1,4-dioate;
(N,N-dimethylcarbamoyl)methyl methyl (2E)but-2-ene-1,4-dioate;
(N-methoxy-N-methylcarbamoyl)methyl methyl (2E)but-2-ene-1,4-dioate;
bis-(2-methoxyethylamino)carbamoyl]methyl methyl (2E)but-2-ene-1,4-dioate;
[N-(methoxycarbonyl)carbamoyl]methyl methyl (2E)but-2ene-1,4-dioate;
4-{2-[(2E)-3-(methoxycarbonyl)prop-2-enoyloxy]acetylamino}butanoic acid, sodium salt;
methyl 2-oxo-2-piperazinylethyl (2E)but-2-ene-1,4-dioate;
methyl 2-oxo-2-(2-oxo(1,3-oxazolidin-3-yl)ethyl (2E)but-2-ene-1,4-dioate;
{N-[2-(dimethylamino)ethyl]carbamoyl}methyl methyl (2E)but-2-ene-1,4 dioate;
methyl 2-(4-methylpiperazinyl)-2-oxoethyl (2E)but-2-ene-1,4-dioate;
methyl {N-[(propylamino)carbonyl]carbamoyl}methyl (2E)but-2-ene-1,4-dioate;
2-(4-acetylpiperazinyl)-2-oxoethyl methyl (2E)but-2-ene-1,4-dioate;
{N,N-bis[2-(methylethoxy)ethyl]carbamoyl}methyl methyl (2E)but-2-ene-1,4-dioate;
methyl 2-(4-benzylpiperazinyl)-2-oxoethyl (2E)but-2-ene-1.4-dioate;
[N,N-bis(2-ethoxyethyl)carbamoyl]methyl methyl (2E)but-2-ene-1,4-dioate;
2-{(2S)-2-[(tert-butyl)oxycarbonyl]pyrrolidinyl}-2-oxoethyl methyl (2E)but-2ene-1,4-dioate;
1-{2-{(2E)-3-(methoxycarbonyl)prop-2-enoyloxy]acetyl}(2S)pyrrolidine-2-carboxylic acid;
(N-{[tert-butyl)oxycarbonyl]methyl}-N-methylcarbamoyl)methyl methyl (2E)but-2-ene-1,4-dioate;
{N-(ethoxycarbonyl)methyl]-N-methylcarbamoyl}methyl methyl (2E)but-2-ene-1,4-dioate;
methyl 1-methyl-2-morpholin-4-yl-2-oxoethyl (2E)but-2-ene-1,4-dioate;
(1S)—[N,N-bis(2-methoxyethyl)carbamoyl]ethyl methyl (2E)but-2-ene-1,4-dioate;
(1S)—(N,N-dimethylcarbamoyl)ethyl methyl (2E)but-2-ene-1,4-dioate;
2-{2-[(2E)-3-(methoxycarbonyl)prop-2-enoyloxy]-N-methylacetylamino}acetic acid;
(N-{[(tert-butyl)oxycarbonyl]methyl}carbamoyl)methyl methyl (2E)but-2-ene-1,4-dioate;

methyl (N-methyl-N-{[(methylethyl)oxycarbonyl]methyl}carbamoyl)methyl (2E)but-2-ene-1,4-dioate;

{N-[(ethoxycarbonyl)methyl]-N-benzylcarbamoyl}methyl methyl (2E)but-2-ene-1,4-dioate;

1-{N-[(ethoxycarbonyl)methyl]-N-benzylcarbamoyl}ethyl methyl (2E)but-2-ene-1,4-dioate;

1-{N-[(ethoxycarbonyl)methyl]-N-methylcarbamoyl}ethyl methyl (2E)but-2-ene-1,4-dioate;

(1S)-1-methyl-2-morpholin-4-yl-2-oxoethyl methyl (2E)but-2-ene-1,4-dioate;

(1S)-1-[N,N-bis(2-methoxyethyl)carbamoyl]ethyl methyl (2E)but-2-ene-1,4-dioate;

(1R)-1-(N,N-diethylcarbamoyl)ethyl methyl (2E)but-2-ene-1,4-dioate; and pharmaceutically acceptable salts of any of the foregoing.

In certain embodiments of a compound of Formula (II), the compound is chosen from:

(N,N-diethylcarbamoyl)methyl methyl (2E)but-2-ene-1,4-dioate;

methyl[N-benzylcarbamoyl]methyl (2E)but-2-ene-1,4-dioate;

methyl 2-morpholin-4-yl-2-oxoethyl (2E)but-2-ene-1,4-dioate;

(N-butylcarbamoyl)methyl methyl (2E)but-2-ene-1,4-dioate;

[N-(2-methoxyethyl)carbamoyl]methyl methyl (2E)but-2-ene-1,4-dioate;

2-{2-[(2E)-3-(methoxycarbonyl)prop-2-enoyloxy]acetylamino}acetic acid;

{2-[(2E)-3-(methoxycarbonyl)prop-2-enoyloxy]acetylamino}butanoic acid;

Methyl (N-(1,3,4-thiadiazol-2yl)carbamoyl)methyl (2E)but-2ene-1,4-dioate;

(N,N-dimethylcarbamoyl)methyl methyl (2E)but-2-ene-1,4-dioate;

(N-methoxy-N-methylcarbamoyl)methyl methyl (2E)but-2-ene-1,4-dioate;

bis-(2-methoxyethylamino)carbamoyl]methyl methyl (2E)but-2-ene-1,4-dioate;

[N-(methoxycarbonyl)carbamoyl]methyl methyl (2E)but-2ene-1,4-dioate;

methyl 2-oxo-2-piperazinylethyl (2E)but-2-ene-1,4-dioate;

methyl 2-oxo-2-(2-oxo(1,3-oxazolidin-3yl)ethyl (2E)but-2ene-1,4-dioate;

{N-[2-(dimethylamino)ethyl]carbamoyl}methyl methyl (2E)but-2ene-1,4 dioate;

(N-[(methoxycarbonyl)ethyl]carbamoyl)methyl methyl (2E)but-2-ene-1,4-dioate;

2-{2-[(2E)-3-(methoxycarbonyl)prop-2-enoyloxy]acetylamino}propanoic acid; and pharmaceutically acceptable salts of any of the foregoing.

In certain embodiments of a compound of Formula (II), the compound is selected from (N,N-diethylcarbamoyl)methyl methyl (2E)but-2-ene-1,4-dioate:

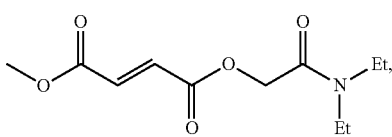 [SMILES: CCN(CC)C(=O)COC(=O)/C=C/C(=O)OC]

or a pharmaceutically acceptable salt thereof; and (methyl 2-morpholin-4-yl-2-oxoethyl (2E)but-2-ene-1,4-dioate:

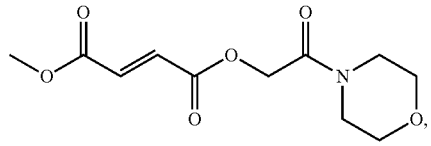 [SMILES: COC(=O)/C=C/C(=O)OCC(=O)N1CCOCC1]

or a pharmaceutically acceptable salt thereof.

Certain embodiments of the methods disclosed herein utilize a compound of Formula (III):

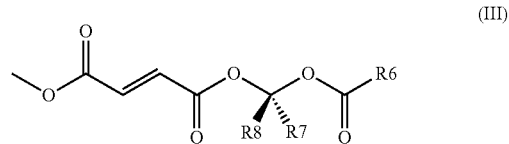

(III)

or a pharmaceutically acceptable salt thereof, wherein:
$R^6$ is chosen from $C_{1-6}$ alkyl, substituted $C_{1-6}$ alkyl, $C_{1-6}$ heteroalkyl, substituted $C_{1-6}$ heteroalkyl, $C_{3-8}$ cycloalkyl, substituted $C_{3-8}$ cycloalkyl, $C_{6-8}$ aryl, substituted $C_{6-8}$ aryl, and —$OR^{10}$ wherein $R^{10}$ is chosen from $C_{1-6}$ alkyl, substituted $C_{1-6}$ alkyl, $C_{3-10}$ cycloalkyl, substituted $C_{3-10}$ cycloalkyl, $C_{6-10}$ aryl, and substituted $C_{6-10}$ aryl; and $R^7$ and $R^8$ are independently chosen from hydrogen, $C_{1-6}$ alkyl, and substituted $C_{1-6}$ alkyl;

wherein each substituent group is independently chosen from halogen, —OH, —CN, —$CF_3$, =O, —$NO_2$, benzyl, —C(O)$NR^{11}_2$, —$R^{11}$, —$OR^{11}$, —C(O)$R^{11}$, —$COOR^{11}$, $N(R^{11})C(O)C(R^{11})_2NR^{11}_2$, and —$NR^{11}_2$ wherein each $R^{11}$ is independently chosen from hydrogen and $C_{1-4}$ alkyl.

In certain embodiments of a compound of Formula (III), each substituent group is independently chosen from halogen, —OH, —CN, —$CF_3$, —$R^{11}$, —$OR^{11}$, and —$NR^{11}_2$ wherein each $R^{11}$ is independently chosen from hydrogen and $C_{1-4}$ alkyl.

In certain embodiments of a compound of Formula (III), each substituent group is independently chosen from =O, $C_{1-4}$ alkyl, and —$COOR^{11}$ wherein $R^{11}$ is chosen from hydrogen and $C_{1-4}$ alkyl.

In certain embodiments of a compound of Formula (III), one of $R^7$ and $R^8$ is hydrogen and the other of $R^7$ and $R^8$ is $C_{1-6}$ alkyl. In certain embodiments of a compound of Formula (II), one of $R^7$ and $R^8$ is hydrogen and the other of $R^7$ and $R^8$ is $C_{1-4}$ alkyl.

In certain embodiments of a compound of Formula (III), one of $R^7$ and $R^8$ is hydrogen and the other of $R^7$ and $R^8$ is chosen from methyl, ethyl, n-propyl, and isopropyl. In certain embodiments of a compound of Formula (III), each of $R^7$ and $R^8$ is hydrogen.

In certain embodiments of a compound of Formula (III), $R^6$ is $C_{1-6}$ alkyl; one of $R^7$ and $R^8$ is hydrogen and the other of $R^7$ and $R^8$ is $C_{1-6}$ alkyl.

In certain embodiments of a compound of Formula (III), $R^6$ is —$OR^{10}$.

In certain embodiments of a compound of Formula (III), $R^{10}$ is chosen from $C_{1-4}$ alkyl, cyclohexyl, and phenyl.

In certain embodiments of a compound of Formula (III), $R^6$ is chosen from methyl, ethyl, n-propyl, and isopropyl; one of $R^7$ and $R^8$ is hydrogen and the other of $R^7$ and $R^8$ is chosen from methyl, ethyl, n-propyl, and isopropyl.

In certain embodiments of a compound of Formula (III), $R^6$ is substituted $C_{1-2}$ alkyl, wherein each of the one or more substituent groups are chosen from —COOH, —NHC(O)CH$_2$NH$_2$, and —NH$_2$.

In certain embodiments of a compound of Formula (III), $R^6$ is chosen from ethoxy, methylethoxy, isopropyl, phenyl, cyclohexyl, cyclohexyloxy, —CH(NH$_2$)CH$_2$COOH, —CH$_2$CH(NH$_2$)COOH, —CH(NHC(O)CH$_2$NH$_2$)—CH$_2$COOH, and —CH$_2$CH(NHC(O)CH$_2$NH$_2$)—COOH.

In certain embodiments of a compound of Formula (III), one of $R^7$ and $R^8$ is hydrogen and the other of $R^7$ and $R^8$ is chosen from hydrogen, methyl, ethyl, n-propyl, and isopropyl; and $R^6$ is chosen from $C_{1-3}$ alkyl and substituted $C_{1-3}$ alkyl, wherein each of the one or more substituent groups are chosen from —COOH, —NHC(O)CH$_2$NH$_2$, and —NH$_2$, —OR$^{10}$ wherein $R^{10}$ is chosen from $C_{1-3}$ alkyl and cyclohexyl, phenyl, and cyclohexyl.

In certain embodiments of a compound of Formula (III), the compound is chosen from:
[1-(ethoxycarbonyloxy)]ethyl methyl (2E)but-2-ene-1,4-dioate;
methyl[1-(methylethoxycarbonyloxy)]ethyl (2E)but-2-ene-1,4-dioate;
[1-(cyclohexyloxycarbonyloxy)]ethyl methyl (2E)but-2-ene-1,4-dioate; and
pharmaceutically acceptable salts of any of the foregoing.

In certain embodiments of a compound of Formula (III), the compound is chosen from:
methyl (2-methylpropanoyloxy)ethyl (2E)but-2-ene-1,4-dioate;
methyl[1-(phenylcarbonyloxy)]ethyl (2E)but-2-ene-1,4-dioate;
[1-(cyclohexylcarbonyloxy)]butyl methyl (2E)but-2-ene-1,4-dioate;
1-[(2E)-3-(methoxycarbonyl)prop-2-enoyloxy]ethyl methyl (2E)but-2-ene-1,4-dioate;
methyl 2-methyl-1-phenylcarbonyloxypropyl (2E)but-2-ene-1,4-dioate; and
pharmaceutically acceptable salts of any of the foregoing.

In certain embodiments of a compound of Formula (III), the compound is chosen from:
[1-(ethoxycarbonyloxy)]ethyl methyl (2E)but-2-ene-1,4-dioate;
methyl[1-(methylethoxycarbonyloxy)]ethyl (2E)but-2-ene-1,4-dioate;
methyl[1-(2-methylpropanoyloxy)]ethyl (2E)but-2-ene-1,4-dioate;
methyl[1-phenylcarbonyloxy]ethyl (2E)but-2-ene-1,4-dioate;
[1-cyclohexylcarbonyloxy]butyl methyl (2E)but-2-ene-1,4-dioate;
[(2E)-3-(methoxycarbonyl)prop-2-enoyloxy]ethyl methyl (2E)but-2-ene-1,4-dioate;
[1-(cyclohexyloxycarbonyloxy)]ethyl methyl (2E)but-2-ene-1,4-dioate;
methyl 2-methyl-1-phenylcarbonyloxypropyl (2E)but-2-ene-1,4-dioate;
3-({[(2E)-3-(methoxycarbonyl)prop-2-enoyloxy]methyl}oxycarbonyl)(3S)-3-aminopropanoic acid;
3-({[(2E)-3-(methoxycarbonyl)prop-2-enoyloxy]methyl}oxycarbonyl)(2S)-2-aminopropanoic acid;
3-({[(2E)-3-(methoxycarbonyl)prop-2-enoyloxy]methyl}oxycarbonyl)(3S)-3-(2-aminoacetylamino)propanoic acid;
3-({[(2E)-3-(methoxycarbonyl)prop-2-enoyloxy]methyl}oxycarbonyl)(2S)-(2-aminoacetylamino)propanoic acid;
and
pharmaceutically acceptable salts of any of the foregoing.

In certain embodiments of a compound of Formula (III), the compound is chosen from:
3-({[(2E)-3-(methoxycarbonyl)prop-2-enoyloxy]methyl}oxycarbonyl)(3S)-3-aminopropanoic acid, 2,2,2-trifluoroacetic acid salt;
3-({[(2E)-3-(methoxycarbonyl)prop-2-enoyloxy]methyl}oxycarbonyl)(2S)-2-aminopropanoic acid, 2,2,2-trifluoroacetic acid salt;
3-({[(2E)-3-(methoxycarbonyl)prop-2-enoyloxy]methyl}oxycarbonyl)(3S)-3-(2-aminoacetylamino)propanoic acid, 2,2,2-trifluoroacetic acid salt;
3-({[(2E)-3-(methoxycarbonyl)prop-2-enoyloxy]methyl}oxycarbonyl)(2S)-(2-aminoacetylamino)propanoic acid, 2,2,2-trifluoroacetic acid salt;
3-{{1-{[(2E)-3-(methoxycarbonyl)prop-2-enoyloxy]}ethoxycarbonyl}}(2S)-2-aminopropanoic acid, hydrochloride salt; and
pharmaceutically acceptable salts of any of the foregoing.

Certain embodiments of the methods disclosed herein utilize a compound of Formula (IV):

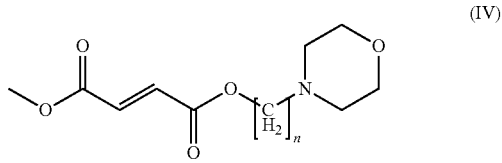

or a pharmaceutically acceptable salt thereof, wherein n is an integer from 2 to 6.

In certain embodiments of a compound of Formula (IV), n is 2, n is 3, n is 4, n is 5, and in certain embodiments, n is 6.

In certain embodiments of a compound of Formula (IV), the compound is a pharmaceutically acceptable salt.

In certain embodiments of a compound of Formula (IV), the compound is the hydrochloride salt.

Synthesis of Compounds

MMF can be synthesized according to the methods described in Dymicky, Preparation of Monomethyl Fumarate, Organic Preparations and Procedures International: The New Journal for Organic Synthesis, Vol 14, Issue 4, 1983; and Spatz et al., J. Org. Chem., 1958, 23 (10), 1559-1560.

DMF can be synthesized according to the methods described in Chinese Patent Publication CN 101318901A, the disclosures of which are incorporated herein by reference.

Compounds of Formula (I) can be synthesized according to the methods described in Speiser et al., U.S. Pat. No. 5,424,332, at column 3, line 33 through column 4, line 2, the disclosures of which are incorporated herein by reference.

Compounds of Formula (II) can be synthesized according to the methods described in Gangakhedkar et al., U.S. Pat. No. 8,148,414, at column 23, line 44 through column 26, line 55 and column 28, line 10 through column 29, line 34, the disclosures of which are incorporated herein by reference.

Compounds of Formula (III) can be synthesized according to the methods described in Gangakhedkar et al., U.S. Pat. No. 8,148,414, at column 29, line 43 through column 31, line 13, the disclosures of which are incorporated herein by reference.

Compounds of Formula (IV) can be synthesized according to the methods described in Cundy et al., U.S. patent application Ser. No. 13/761,864, filed Feb. 7, 2013, at page 34, line 21 through page 41, line 3, the disclosures of which are incorporated herein by reference.

Pharmaceutical Compositions

Pharmaceutical compositions provided by the present disclosure may comprise a therapeutically effective amount of MMF and/or a prodrug of MMF together with a suitable amount of one or more pharmaceutically acceptable vehicles so as to provide a composition for proper administration to a patient. Suitable pharmaceutical vehicles are described in the art.

In certain embodiments, MMF and/or a compound of Formulae (I)-(IV) may be incorporated into pharmaceutical compositions to be administered orally. Oral administration of such pharmaceutical compositions may result in uptake of MMF and/or a compound of Formulae (I)-(IV) throughout the intestine and entry into the systemic circulation. Such oral compositions may be prepared in a manner known in the pharmaceutical art and comprise MMF and/or a compound of Formulae (I)-(IV) and at least one pharmaceutically acceptable vehicle. Oral pharmaceutical compositions may include a therapeutically effective amount of MMF and/or a compound of Formulae (I)-(IV) and a suitable amount of a pharmaceutically acceptable vehicle, so as to provide an appropriate form for administration to a patient.

MMF and/or a compound of Formulae (I)-(IV) may be incorporated into pharmaceutical compositions to be administered by any other appropriate route of systemic administration including intramuscular, intravenous and oral.

Pharmaceutical compositions comprising MMF and/or a compound of Formulae (I)-(IV) and may be manufactured by means of conventional mixing, dissolving, granulating, dragee-making, levigating, emulsifying, encapsulating, entrapping, or lyophilizing processes. Pharmaceutical compositions may be formulated in a conventional manner using one or more physiologically acceptable carriers, diluents, excipients, or auxiliaries, which facilitate processing of MMF and/or a compound of Formulae (I)-(IV) or crystalline forms thereof and one or more pharmaceutically acceptable vehicles into formulations that can be used pharmaceutically. Proper formulation is dependent upon the route of administration chosen. Pharmaceutical compositions provided by the present disclosure take the form of sustained-release formulations suitable for administration to a patient.

Pharmaceutical compositions provided by the present disclosure may be formulated in a unit dosage form. A unit dosage form refers to a physically discrete unit suitable as a unitary dose for patients undergoing treatment, with each unit containing a predetermined quantity of MMF and/or a compound of Formulae (I)-(IV) calculated to produce an intended therapeutic effect. A unit dosage form may be for a single daily dose, for administration 2 times per day, or one of multiple daily doses, e.g., 3 or more times per day. When multiple daily doses are used, a unit dosage form may be the same or different for each dose. One or more dosage forms may comprise a dose, which may be administered to a patient at a single point in time or during a time interval.

In certain embodiments, an oral dosage form provided by the present disclosure may be a controlled release dosage form. Controlled delivery technologies can improve the absorption of a drug in a particular region or regions of the gastrointestinal tract. Controlled drug delivery systems may be designed to deliver a drug in such a way that the drug level is maintained within a therapeutically effective window and effective and safe blood levels are maintained for a period as long as the system continues to deliver the drug with a particular release profile in the gastrointestinal tract. Controlled drug delivery may produce substantially constant blood levels of a drug over a period of time as compared to fluctuations observed with immediate release dosage forms. For some drugs, maintaining a constant blood and tissue concentration throughout the course of therapy is the most desirable mode of treatment. Immediate release of drugs may cause blood levels to peak above the level required to elicit a desired response, which may waste the drug and may cause or exacerbate toxic side effects. Controlled drug delivery can result in optimum therapy, and not only can reduce the frequency of dosing, but may also reduce the severity of side effects. Examples of controlled release dosage forms include dissolution controlled systems, diffusion controlled systems, ion exchange resins, osmotically controlled systems, erodable matrix systems, pH independent formulations, gastric retention systems, and the like.

An appropriate oral dosage form for a particular pharmaceutical composition provided by the present disclosure may depend, at least in part, on the gastrointestinal absorption properties of MMF and/or a compound of Formulae (I)-(IV) the stability of MMF and/or a compound of Formulae (I)-(IV) in the gastrointestinal tract, the pharmacokinetics of MMF and/or a compound of Formulae (I)-(IV) and the intended therapeutic profile. An appropriate controlled release oral dosage form may be selected for a particular compound. For example, gastric retention oral dosage forms may be appropriate for compounds absorbed primarily from the upper gastrointestinal tract, and sustained release oral dosage forms may be appropriate for compounds absorbed primarily from the lower gastrointestinal tract. Certain compounds are absorbed primarily from the small intestine. In general, compounds traverse the length of the small intestine in about 3 to 5 hours. For compounds that are not easily absorbed by the small intestine or that do not dissolve readily, the window for active agent absorption in the small intestine may be too short to provide a desired therapeutic effect.

In certain embodiments, pharmaceutical compositions provided by the present disclosure may be practiced with dosage forms adapted to provide sustained release of MMF and/or a compound of Formulae (I)-(IV) upon oral administration. Sustained release oral dosage forms may be used to release drugs over a prolonged time period and are useful when it is desired that a drug or drug form be delivered to the lower gastrointestinal tract, including the colon. Sustained release oral dosage forms include any oral dosage form that maintains therapeutic concentrations of a drug in a biological fluid such as the plasma, blood, cerebrospinal fluid, or in a tissue or organ for a prolonged time period. Sustained release oral dosage forms include diffusion-controlled systems such as reservoir devices and matrix devices, dissolution-controlled systems, osmotic systems, and erosion-controlled systems. Sustained release oral dosage forms and methods of preparing the same are well known in the art.

In certain embodiments, pharmaceutical compositions provided by the present disclosure may include any systemic dosage form of the MMF and/or a prodrug of MMF, and wherein, when administered to a patient, the maximum average concentration of MMF in the blood plasma of the patient is less than 500 ng/ml. In one embodiment, the maximum average concentration is less than 400 ng/ml. In another embodiment, the maximum average concentration is less than 350 ng/ml. In another embodiment, the maximum average concentration is less than 300 ng/ml. In another embodiment, the maximum average concentration is less than 250 ng/ml. In another embodiment, the maximum average concentration is less than 200 ng/ml. In another embodiment, the maximum average concentration is less than 150 ng/ml. In some embodiments, the prodrug of MMF is a compound of Formulae (I)-(IV).

In certain embodiments, pharmaceutical compositions provided by the present disclosure may include any systemic dosage form of the MMF and/or a prodrug of MMF, and wherein, when administered to a patient, the average maximum rate of rise in MMF concentration in the blood plasma of the patients is less than 0.25 wt % ng-eq of MMF dosed/ml/hr. In one embodiment, the average maximum rate of rise is less than 0.20 wt % ng-eq of MMF dosed/ml/hr. In one embodiment, the average maximum rate of rise is less than 0.15 wt % ng-eq of MMF dosed/ml/hr. In one embodiment, the average maximum rate of rise is less than 0.10 wt % ng-eq of MMF dosed/ml/hr.

In certain embodiments, pharmaceutical compositions provided by the present disclosure may include any systemic dosage form of the MMF and/or a prodrug of MMF, and wherein, when administered to a patient, the average maximum rate of rise in MMF concentration in the blood plasma of the patients is less than 0.25 wt % ng-eq of MMF dosed/ml/hr; and an average MMF concentration in the blood plasma of the patients, measured at a time of said maximum rate of rise, is less than 200 ng/ml.

In certain embodiments, pharmaceutical compositions provided by the present disclosure may include any systemic dosage form of the MMF and/or a prodrug of MMF, and wherein, when administered to a patient, the average maximum rate of rise in MMF concentration in the blood plasma of the patients is less than 0.20 wt % ng-eq of MMF dosed/ml/hr; and an average MMF concentration in the blood plasma of the patients, measured at a time of said maximum rate of rise, is less than 200 ng/ml or less than 150 ng/ml.

In certain embodiments, pharmaceutical compositions provided by the present disclosure may include any systemic dosage form of the MMF and/or a prodrug of MMF, and wherein, when administered to a patient, the average maximum rate of rise in MMF concentration in the blood plasma of the patients is less than 0.15 wt % ng-eq of MMF dosed/ml/hr; and an average MMF concentration in the blood plasma of the patients, measured at a time of said maximum rate of rise, is less than 180 ng/ml.

In certain embodiments, pharmaceutical compositions provided by the present disclosure may include any systemic dosage form of the MMF and/or a prodrug of MMF, and wherein, when administered to a patient, the average maximum rate of rise in MMF concentration in the blood plasma of the patients is less than 0.10 wt % ng-eq of MMF dosed/ml/hr; and an average MMF concentration in the blood plasma of the patients, measured at a time of said maximum rate of rise, is less than 140 ng/ml.

In another embodiment, the prodrug of MMF is a compound of Formulae (I)-(IV).

In certain embodiments, pharmaceutical compositions provided by the present disclosure may include any enteric-coated sustained release oral dosage form of the MMF and/or a prodrug of MMF, and wherein, when subjected to an in vitro dissolution test employing as a dissolution medium 750 mL of 0.1 N hydrochloric acid, at pH 1.2, for a period of 2 hours, followed by addition of 250 mL of 200 mM tribasic sodium phosphate buffer resulting in an adjustment of the pH of the dissolution medium to 6.8, the dissolution medium being maintained at 37° C. and stirred at 100 rpm, the dosage form releases:

(i) less than 10 wt % of the dose over an initial 2 hours of the in vitro dissolution test; (ii) at least 90 wt % of the dose over not less than an initial 8 hours of the in vitro dissolution test;

(iii) no more than 30 wt % of the dose in any one hour during the in vitro dissolution test; and (iv) no more than 40 wt % of the dose in any consecutive two hours during the in vitro dissolution test.

In one embodiment, the prodrug of MMF is a compound of Formulae (I)-(IV). In another embodiment, the enteric-coated oral dosage form is administered to a patient at a dosing frequency of not more than twice per day.

In certain embodiments, pharmaceutical compositions provided by the present disclosure may include any non-enteric-coated sustained release oral dosage form of the MMF and/or a prodrug of MMF, and wherein, when subjected to an in vitro dissolution test employing as a dissolution medium 750 mL of 0.1 N hydrochloric acid, at pH 1.2, for a period of 2 hours, followed by addition of 250 mL of 200 mM tribasic sodium phosphate buffer resulting in an adjustment of the pH of the dissolution medium to 6.8, the dissolution medium being maintained at 37° C. and stirred at 100 rpm, the dosage form releases:

(i) at least 90 wt % of the dose over not less than an initial 8 hours of the in vitro dissolution test;

(ii) no more than 30 wt % of the dose in any one hour during the in vitro dissolution test; and (iii) no more than 40 wt % of the dose in any consecutive two hours during the in vitro dissolution test.

In one embodiment, the prodrug of MMF is a compound of Formulae (I)-(IV). In another embodiment, the non-enteric-coated oral dosage form is administered to a patient at a dosing frequency of not more than twice per day.

In certain embodiments, pharmaceutical compositions provided by the present disclosure may include any suitable dosage forms that achieve the above described in vitro release profiles. Such dosage forms may be any systemic dosage forms, including sustained release enteric-coated oral dosage form and sustained release non-enteric-coated oral dosage form. Examples of suitable dosage forms are described herein. Those skilled in the formulation art can develop any number of acceptable dosage forms given the dosage forms described in the examples as a starting point.

An appropriate dose of MMF and/or a compound of Formulae (I)-(IV) or pharmaceutical composition comprising MMF and/or a compound of Formulae (I)-(IV) may be determined according to any one of several well-established protocols. For example, animal studies such as studies using mice, rats, dogs, and/or monkeys may be used to determine an appropriate dose of a pharmaceutical compound. Results from animal studies may be extrapolated to determine doses for use in other species, such as for example, humans.

Uses

Compounds of Formulae (I)-(IV) are prodrugs of MMF. Thus, compounds of Formulae (I)-(IV) and pharmaceutical compositions thereof may be administered to a patient suffering from diseases, disorders, conditions, and symptoms of any of the foregoing for which alkyl hydrogen fumarates, such as MMF, are known to provide or are later found to provide therapeutic benefit. MMF and/or a compound of Formulae (I)-(IV) can be used to treat a disease chosen from adrenal leukodystrophy, AGE-induced genome damage, Alexanders Disease, Alper's Disease, Alzheimer's disease, amyotrophic lateral sclerosis, angina pectoris, arthritis, asthma, balo concentric sclerosis, Canavan disease, cardiac insufficiency including left ventricular insufficiency, central nervous system vasculitis, Charcott-Marie-Tooth Disease, childhood ataxia with central nervous system hypomyelination, chronic idiopathic peripheral neuropathy, chronic obstructive pulmonary disease, Crohn's disease, diabetic retinopathy, graft versus host disease, hepatitis C viral infection, herpes simplex viral infection, human immunodeficiency viral infection, Huntington's disease, irritable bowel disorder, ischemia, Krabbe Disease, lichen planus, macular degeneration, mitochondrial encephalomyopathy, monomelic amyotrophy, multiple sclerosis, myocardial infarction, neurodegeneration with brain iron accumulation, neuromyelitis optica, neurosarcoidosis, NF-κB mediated diseases, optic neuritis, pareneoplastic syndromes, Parkinson's disease, Pelizaeus-Merzbacher disease, primary lateral sclerosis, progressive supranuclear palsy, psoriasis, reperfusion injury, retinopathia pigmentosa, Schilders Disease, subacute necrotizing myelopathy, susac syndrome, transplantation rejection, transverse myelitis, a tumor, ulcerative colitis, Zellweger's syndrome, granulomas including annulaire, pemphigus, bollus pemphigoid, behcet's, contact dermatitis, acute dermatitis, chronic dermatitis, alopecia areata (totalis and universalis), sarcoidosis, cutaneous sarcoidosis, pyoderma gangrenosum, cutaneous lupus, Crohn's disease or cutaneous Crohn's disease.

Methods of treating a disease in a patient provided by the present disclosure comprise administering to a patient in need of such treatment a therapeutically effective amount of MMF and/or a compound of Formulae (I)-(IV). These compounds, and pharmaceutical compositions thereof, provide therapeutic or prophylactic plasma and/or blood concentrations of MMF following administration to a patient. MMF and/or a compound of Formulae (I)-(IV) may be administered in an amount and using a dosing schedule as appropriate for treatment of a particular disease. Daily doses of MMF and/or a compound of Formulae (I)-(IV) may range from about 0.01 mg/kg to about 50 mg/kg, from about 0.1 mg/kg to about 50 mg/kg, from about 1 mg/kg to about 50 mg/kg, and in certain embodiments, from about 5 mg/kg to about 25 mg/kg. In certain embodiments, MMF and/or a compound of Formulae (I)-(IV) may be administered at a dose over time from about 1 mg to about 5 g per day, from about 10 mg to about 4 g per day, and in certain embodiments from about 20 mg to about 2 g per day. An appropriate dose of MMF and/or a compound of Formulae (I)-(IV) may be determined based on several factors, including, for example, the body weight and/or condition of the patient being treated, the severity of the disease being treated, the incidence and/or severity of side effects, the manner of administration, and the judgment of the prescribing physician. Appropriate dose ranges may be determined by methods known to those skilled in the art.

MMF and the compounds of Formulae (I)-(IV) may be assayed in vitro and in vivo for the desired therapeutic or prophylactic activity prior to use in humans. In vivo assays, for example using appropriate animal models, may also be used to determine whether administration of MMF and/or a compound of Formulae (I)-(IV) is therapeutically effective.

In certain embodiments, a therapeutically effective dose of MMF and/or a compound of Formulae (I)-(IV) may provide therapeutic benefit without causing substantial toxicity including adverse side effects. Toxicity of MMF and/or a compound of Formulae (I)-(IV) and/or metabolites thereof may be determined using standard pharmaceutical procedures and may be ascertained by those skilled in the art. The dose ratio between toxic and therapeutic effect is the therapeutic index. A dose of MMF and/or a compound of Formulae (I)-(IV) may be within a range capable of establishing and maintaining a therapeutically effective circulating plasma and/or blood concentration of MMF and/or a compound of Formulae (I)-(IV) that exhibits little or no toxicity.

MMF and compounds of Formulae (I)-(IV) may be used to treat a disease chosen from adrenal leukodystrophy, AGE-induced genome damage, Alexanders Disease, Alper's Disease, Alzheimer's disease, amyotrophic lateral sclerosis, angina pectoris, arthritis, asthma, balo concentric sclerosis, Canavan disease, cardiac insufficiency including left ventricular insufficiency, central nervous system vasculitis, Charcott-Marie-Tooth Disease, childhood ataxia with central nervous system hypomyelination, chronic idiopathic peripheral neuropathy, chronic obstructive pulmonary disease, Crohn's disease, diabetic retinopathy, graft versus host disease, hepatitis C viral infection, herpes simplex viral infection, human immunodeficiency viral infection, Huntington's disease, irritable bowel disorder, ischemia, Krabbe Disease, lichen planus, macular degeneration, mitochondrial encephalomyopathy, monomelic amyotrophy, multiple sclerosis, myocardial infarction, neurodegeneration with brain iron accumulation, neuromyelitis optica, neurosarcoidosis, NF-κB mediated diseases, optic neuritis, pareneoplastic syndromes, Parkinson's disease, Pelizaeus-Merzbacher disease, primary lateral sclerosis, progressive supranuclear palsy, psoriasis, reperfusion injury, retinopathia pigmentosa, Schilders Disease, subacute necrotizing myelopathy, susac syndrome, transplantation rejection, transverse myelitis, a tumor, ulcerative colitis, Zellweger's syndrome, granulomas including annulaire, pemphigus, bollus pemphigoid, behcet's, contact dermatitis, acute dermatitis, chronic dermatitis, alopecia greata (totalis and universalis), sarcoidosis, cutaneous sarcoidosis, pyoderma gangrenosum, cutaneous lupus, Crohn's disease or cutaneous Crohn's disease. The underlying etiology of any of the foregoing diseases being treated may have a multiplicity of origins. Further, in certain embodiments, a therapeutically effective amount of MMF and/or the compound of Formulae (I)-(IV) may be administered to a patient, such as a human, as a preventative measure against the foregoing diseases and disorders. Thus, a therapeutically effective amount of MMF and/or a compound of Formulae (I)-(IV) may be administered as a preventative measure to a patient having a predisposition for and/or history of adrenal leukodystrophy, AGE-induced genome damage, Alexanders Disease, Alper's Disease, Alzheimer's disease, amyotrophic lateral sclerosis, angina pectoris, arthritis, asthma, balo concentric sclerosis, Canavan disease, cardiac insufficiency including left ventricular insufficiency, central nervous system vasculitis, Charcott-Marie-Tooth Disease, childhood ataxia with central nervous system hypomyelination, chronic idiopathic peripheral neuropathy, chronic obstructive pulmonary disease, Crohn's disease, diabetic retinopathy, graft versus host disease, hepatitis C viral infection, herpes simplex viral infection, human immunodeficiency viral infection, Huntington's disease, irritable bowel disorder, ischemia, Krabbe Disease, lichen planus, macular degeneration, mitochondrial encephalomyopathy, monomelic amyotrophy, multiple sclerosis, myocardial infarction, neurodegeneration with brain iron accumulation, neuromyelitis optica, neurosarcoidosis, NF-κB mediated diseases, optic neuritis, pareneoplastic syndromes, Parkinson's disease, Pelizaeus-Merzbacher disease, primary lateral sclerosis, progressive supranuclear palsy, psoriasis, reperfusion injury, retinopathia pigmentosa, Schilders Disease, subacute necrotizing myelopathy, susac syndrome, transplantation rejection, transverse myelitis, a tumor, ulcerative colitis, Zellweger's syndrome, granulomas including annulaire, pemphigus, bollus pemphigoid, behcet's, contact dermatitis, acute dermatitis, chronic dermatitis, alopecia greata (totalis and universalis), sarcoidosis, cutaneous sarcoidosis, pyoderma gangrenosum, cutaneous lupus, Crohn's disease and/or cutaneous Crohn's disease.

Administration

MMF and/or a prodrug of MMF and pharmaceutical compositions thereof may be administered orally or by any other appropriate route suitable for systemic, as opposed to local, administration. For example, systemic administration can be by infusion or bolus injection, by absorption through epithelial or mucocutaneous linings (e.g., oral mucosa, rectal, and intestinal mucosa, etc.). Other suitable routes of systemic administration include, but are not limited to, intradermal, intramuscular, intraperitoneal, intravenous, subcutaneous, intranasal, epidural, oral, sublingual and inhalation.

The amount of MMF and/or a prodrug of MMF that will be effective in the treatment of a disease in a patient will depend, in part, on the nature of the condition and can be determined by standard clinical techniques known in the art. In addition, in vitro or in vivo assays may be employed to help identify optimal dosage ranges. A therapeutically effective amount of MMF and/or a prodrug of MMF to be administered may also depend on, among other factors, the subject being treated, the weight of the subject, the severity of the disease, the manner of administration, and the judgment of the prescribing physician. In the case of an MMF prodrug, for which MMF is the pharmacologically active metabolite, the amount of prodrug to be administered is generally determined by calculating the weight of any pharmacologically inactive promoiety that is cleaved during metabolism of the prodrug and then administering a MMF equivalent amount of the prodrug.

For systemic administration, a therapeutically effective dose may be estimated initially from in vitro assays. For example, a dose may be formulated in animal models to achieve a beneficial circulating composition concentration range. Initial doses may also be estimated from in vivo data, e.g., animal models, using techniques that are known in the art. Such information may be used to more accurately determine useful doses in humans. One having ordinary skill in the art may optimize administration to humans based on animal data.

A dose may be administered in a single dosage form or in multiple dosage forms. When multiple dosage forms are used the amount of compound contained within each dosage form may be the same or different. The amount of MMF and/or a prodrug of MMF contained in a dose may depend on the route of administration and whether the disease in a patient is effectively treated by acute, chronic, or a combination of acute and chronic administration.

In certain embodiments an administered dose is less than a toxic dose. Toxicity of the compositions described herein may be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. In certain embodiments, MMF and/or a prodrug of MMF may exhibit a high therapeutic index. The data obtained from these cell culture assays and animal studies may be used in formulating a dosage range that is not toxic for use in humans. A dose of MMF and/or a prodrug of MMF provided by the present disclosure may be within a range of circulating concentrations in for example the blood, plasma, or central nervous system, that include the effective dose and that exhibits little or no toxicity. A dose may vary within this range depending upon the dosage form employed and the route of administration utilized. In certain embodiments, an escalating dose may be administered.

Combination Therapy

Methods provided by the present disclosure further comprise administering one or more pharmaceutically active compounds in addition to MMF and/or a prodrug of MMF. Such compounds may be provided to treat the same disease or a different disease than the disease being treated with the MMF and/or MMF prodrug.

In certain embodiments, MMF and/or an MMF prodrug may be used in combination with at least one other therapeutic agent. In certain embodiments, MMF and/or a MMF prodrug may be administered to a patient together with another compound for treating diseases and conditions including: adrenal leukodystrophy, Alexanders Disease, Alper's Disease, balo concentric sclerosis, Canavan disease, central nervous system vasculitis, Charcott-Marie-Tooth Disease, childhood ataxia with central nervous system hypomyelination, diabetic retinopathy, graft versus host disease, hepatitis C viral infection, herpes simplex viral infection, human immunodeficiency viral infection, Krabbe Disease, lichen planus, macular degeneration, monomelic amyotrophy, neurodegeneration with brain iron accumulation, neuromyelitis optica, neurosarcoidosis, optic neuritis, pareneoplastic syndromes, Pelizaeus-Merzbacher disease, primary lateral sclerosis, progressive supranuclear palsy, Schilders Disease, subacute necrotizing myelopathy, susac syndrome, transverse myelitis, a tumor and Zellweger's syndrome.

MMF and/or an MMF prodrug and the at least one other therapeutic agent may act additively or, and in certain embodiments, synergistically. The at least one additional therapeutic agent may be included in the same dosage form as MMF and/or the MMF prodrug or may be provided in a separate dosage form. Methods provided by the present disclosure can further include, in addition to administering MMF and/or an MMF prodrug, administering one or more therapeutic agents effective for treating the same or different disease than the disease being treated by MMF and/or the MMF prodrug. Methods provided by the present disclosure include administration of MMF and/or an MMF prodrug and one or more other therapeutic agents provided that the combined administration does not inhibit the therapeutic efficacy of the MMF and/or the MMF prodrug and/or does not typically produce significant and/or substantial adverse combination effects.

In certain embodiments, dosage forms comprising MMF and/or a prodrug of MMF may be administered concurrently with the administration of another therapeutic agent, which may be part of the same dosage form as, or in a different dosage form than that comprising MMF and/or a prodrug of MMF. MMF and/or a prodrug of MMF may be administered prior or subsequent to administration of another therapeutic agent. In certain embodiments of combination therapy, the combination therapy may comprise alternating between administering MMF and/or a prodrug of MMF and a composition comprising another therapeutic agent, e.g., to minimize adverse drug effects associated with a particular drug. When MMF and/or a prodrug of MMF is administered concurrently with another therapeutic agent that potentially may produce an adverse drug effect including, but not limited to, toxicity, the other therapeutic agent may advantageously be administered at a dose that falls below the threshold at which the adverse drug reaction is elicited.

In certain embodiments, dosage forms comprising MMF and/or a prodrug of MMF may be administered with one or more substances to enhance, modulate and/or control release, bioavailability, therapeutic efficacy, therapeutic potency, stability, and the like of MMF and/or a prodrug of MMF. For example, to enhance the therapeutic efficacy of a MMF and/or a prodrug of MMF, the MMF and/or a prodrug of MMF may be co-administered with or a dosage form comprising MMF and/or a prodrug of MMF may comprise one or more active agents to increase the absorption or diffusion of MMF and/or a prodrug of MMF from the gastrointestinal tract to the systemic circulation, or to inhibit degradation of the MMF and/or a prodrug of MMF in the blood of a patient. In certain embodiments, MMF and/or a prodrug of MMF may be co-administered with an active agent having pharmacological effects that enhance the therapeutic efficacy of a MMF and/or a prodrug of MMF.

EXAMPLES

The following examples illustrate various aspects of the disclosure. It will be apparent to those skilled in the art that many modifications, both to materials and methods, may be practiced without departing from the scope of the disclosure.

Example 1

Preparation of Sustained Release Dosage Form

Enteric Coated, 15% HPMC in Core, with Barrier Layer

Delayed sustained release tablets containing an MMF prodrug were made having the ingredients shown in Table 3:

TABLE 3

Composition of Enteric Coated Sustained Release Tablet (15% HPMC in Core)

| Component | Manufacturer | Role | Quantity (mg/tablet) | Quantity (% w/w) |
|---|---|---|---|---|
| (N,N-Diethylcarbamoyl)methyl methyl (2E)but-2-ene-1,4-dioate [Compound (1)] | XenoPort (Santa Clara, CA) | Drug substance | 200.00 | 66.74 |
| Hydroxypropyl Cellulose | Ashland (Hopewell, VA) | Binder | 6.19 | 2.06 |
| Lactose Monohydrate | Foremost (Rothschild, WI) | Filler | 44.95 | 15.00 |
| Hypromellose 2208 | Dow Chemical (Midland, MI) | Sustained release agent | 44.95 | 15.00 |
| Silicon Dioxide | Cabot (Tuscola, IL) | Glidant | 0.60 | 0.20 |
| Magnesium Stearate | Mallinckrodt (St. Louis, MO) | Lubricant | 3.00 | 1.00 |
| | | Total Core | 299.69 | 100.00 |
| Opadry 03O19184 | Colorcon (West Point, PA) | Barrier coat | 7.13 | 2.38 |
| | | Total Barrier Coating | 7.13 | 2.38 |
| Methacrylic Acid Co-polymer Dispersion | Evonik Industries (Essen, Germany) | Enteric polymer | 24.20 | 8.08 |
| Triethyl Citrate | Vertellus (Greensboro, NC) | Plasticizer | 1.25 | 0.42 |
| PlasACRYL ™ T20 | Emerson Resources (Norristown, PA) | Anti-tacking agent | 2.41 | 0.80 |
| | | Total Enteric Coating | 27.87 | 9.30 |
| | | Total Tablet | 334.69 | 111.68 |

The tablets were made according to the following steps. The core tablets were prepared using a wet granulation process. The granulation was performed in two batches at 456 g per batch. Compound (1) and hydroxypropyl cellulose were passed through a conical mill with a 610 micron round holed screen. Compound (1) and hydroxypropyl cellulose were then combined in a Key KG-5 granulator bowl and mixed with water addition for approximately 7 minutes. The wet granules were dried in a Glatt GPCG-1 fluid bed dryer at 40° C. The two portions of dried granules were sized by passing through a conical mill with an approximately 1300 micron grater type screen. The milled granules were blended with the hypromellose 2208, silicon dioxide, and lactose monohydrate for 10 minutes in an 8 quart (7.61) V-blender. This blend was passed through an 850 micron mesh screen. The magnesium stearate was passed through a 600 micron mesh screen and blended with the additional core materials in the V-blender for 5 minutes. Core tablets (299.69 mg) were compressed using a GlobePharma Minipress II rotary tablet press with 8.6 mm round concave tooling. The core tablets had a final mean hardness of approximately 12 kp. For the coating, an aqueous suspension was prepared by mixing with an impeller 63.8 g Opadry 03O19184 with 770.7 g of purified water. The water contained in the suspension is removed during the film coating process and therefore not included in the final formulation in Table 3. The tablets were coated with the aqueous suspension in an O'Hara Technologies Labcoat M coater with a 12" (30.5 cm) diameter perforated pan until the desired weight gain of barrier coat was achieved. The coating process occurred at an inlet temperature of approximately 52° C. and an outlet temperature of 36° C. After coating, the tablets were dried for 2 hours at 40° C. An aqueous suspension was prepared by mixing with an impeller 405.1 g methacrylic acid copolymer dispersion, 6.3 g triethyl citrate, 60.6 g PlasACRYL™ T20 with 228.1 g water. The water contained in the methacrylic acid copolymer dispersion and the PlasACRYL™ T20 is removed during the film coating process and therefore not included in the final formulation in Table 3. The tablets were coated with the aqueous suspension in the O'Hara Technologies Labcoat M coater until the desired weight gain of enteric film was achieved. The coating process occurred at an inlet temperature of approximately 40° C. and an outlet temperature of 30° C. After coating, the tablets were dried for 2 hours at 40° C.

Example 2

In Vitro Dissolution Profile of Example 1 Dosage Form

A two-stage dissolution method was used to determine the in vitro dissolution profile of dosage forms prepared according to Example 1. The 2-stage dissolution test was used to better approximate the pH conditions experienced by a dosage form after swallowing by a patient, i.e., low pH of the stomach followed by near neutral pH of the intestines. The dosage forms were first placed into a dissolution vessel (USP, Type I, basket) containing 750 mL of 0.1 N hydrochloric acid (pH 1.2). After 2 hours, 250 mL of 200 mM tribasic sodium phosphate was added to the vessel resulting in a pH adjustment from 1.2 to 6.8. The dissolution medium was kept at 37° C. and was agitated at 100 rpm.

For the Example 1 dosage forms, samples of the dissolution medium were withdrawn after 1 and 2 hours in the low pH stage, and at 0.5, 2, 4, 7, 10, and 14 hours following buffer addition. The released amount of the MMF prodrug in the samples was determined by reverse phase HPLC using a C18 column and a 7 minute gradient method according to Table 4 where Mobile Phase A is water/0.1% $H_3PO_4$ and Mobile Phase B is water/acetonitrile/$H_3PO_4$ (10/90/0.1 by volume) with UV detection at 210 nm.

TABLE 4

| HPLC Gradient Conditions | | |
|---|---|---|
| Time (minute) | % Mobile Phase A | % Mobile Phase B |
| 0 | 85 | 15 |
| 5 | 35 | 65 |
| 5.5 | 85 | 15 |
| 7 | 85 | 15 |

As shown in FIG. 1, for dosage forms prepared according to Example 1, drug release is delayed for approximately 2 hours, followed by sustained release reaching >90% at 12 hours.

Example 3

Preparation of Delayed Sustained Release Dosage Form

Enteric Coated, 15% HPMC in Core, without Barrier Layer

Delayed sustained release tablets containing compound (1) were made having the ingredients shown in Table 5:

TABLE 5

Composition of Enteric Coated Sustained Release Tablet
(15% HPMC in Core, without Barrier Layer)

| Component | Manufacturer | Role | Quantity (mg/tablet) | Quantity (% w/w) |
|---|---|---|---|---|
| (N,N-Diethylcarbamoyl)methyl methyl (2E)but-2-ene-1,4-dioate [Compound 1] | XenoPort (Santa Clara, CA) | Drug substance | 200.00 | 66.74 |
| Hydroxypropyl Cellulose | Ashland (Hopewell, VA) | Binder | 6.18 | 2.06 |
| Lactose Monohydrate | Foremost (Rothschild, WI) | Filler | 44.95 | 15.00 |
| Hypromellose 2208 | Dow Chemical (Midland, MI) | Sustained release agent | 44.95 | 15.00 |

TABLE 5-continued

Composition of Enteric Coated Sustained Release Tablet
(15% HPMC in Core, without Barrier Layer)

| Component | Manufacturer | Role | Quantity (mg/tablet) | Quantity (% w/w) |
|---|---|---|---|---|
| Silicon Dioxide | Cabot (Tuscola, IL) | Glidant | 0.60 | 0.20 |
| Magnesium Stearate | Mallinckrodt (St. Louis, MO) | Lubricant | 3.00 | 1.00 |
| | | Total Core | 299.68 | 100.00 |
| Methacrylic Acid Co-polymer Dispersion | Evonik Industries (Essen, Germany) | Enteric polymer | 23.42 | 7.82 |
| Triethyl Citrate | Vertellus (Greensboro, NC) | Plasticizer | 1.21 | 0.41 |
| PlasACRYL ™ T20 | Emerson Resources (Norristown, PA) | Anti-tacking agent | 2.33 | 0.78 |
| | | Total Coat | 27.90 | 9.00 |
| | | Total Tablet | 327.59 | 109.00 |

The tablets were made according to the following steps. The core tablets were prepared using a wet granulation process. The granulation was performed in two batches at 463.9 g per batch. Compound (1) and hydroxypropyl cellulose were passed through a conical mill with a 610 micron round holed screen. Compound (1) and hydroxypropyl cellulose were then combined in a Key KG-5 granulator bowl and mixed with water addition for approximately 10 minutes. The wet granules were dried in a Glatt GPCG-1 fluid bed dryer at 40° C. The two portions of dried granules were blended with silicon dioxide and sized by passing through a conical mill with an approximately 1300 micron grater type screen. The milled granules were blended with the hypromellose 2208 and lactose monohydrate for 10 minutes in an 8 quart (7.6l) V-blender. This blend was passed through an 850 micron mesh screen. The magnesium stearate was passed through a 600 micron mesh screen and blended with the additional core materials in the V-blender for 5 minutes. Core tablets (299.68 mg) were compressed using a GlobePharma Minipress II rotary tablet press with $^{11}/_{32}$" round concave tooling. The core tablets had a final mean hardness of approximately 11 kp. For the coating, an aqueous suspension was prepared by mixing with an impeller 578.7 g methacrylic acid copolymer dispersion, 9.0 g triethyl citrate, 86.5 g PlasACRYL™ T20 with 325.8 g water. The water contained in the methacrylic acid copolymer dispersion and the PlasACRYL™ T20 is removed during the film coating process and therefore not included in the final formulation in Table 4. The tablets were coated with the aqueous suspension in the O'Hara Technologies Labcoat M coater until the desired weight gain of enteric film was achieved. The coating process occurred at an inlet temperature of approximately 41° C. and an outlet temperature of 31° C. After coating, the tablets were dried for 2 hours at 40° C.

Example 4

Safety, Tolerability, and Pharmacokinetics of Example 3 Dosage Form

A randomized, double-blind crossover, food effect, single-dose study of the safety, tolerability, and pharmacokinetics of an oral dosage form of (N,N-Diethylcarbamoyl)methyl methyl (2E)but-2-ene-1,4-dioate in healthy adult subjects was conducted. Twenty-four healthy adult volunteers (males and females) participated in the study. Twelve of the subjects received a dosage form of Example 3, once in a fed condition and once in a fasted condition, with a two-week washout between treatments. The fasted dosing was achieved by dosing the subject following an overnight fast while the fed dosing was achieved by dosing the subject after consuming a high fat-content breakfast. The tested dosage forms contained 200 mg of (N,N-Diethylcarbamoyl)methyl methyl (2E)but-2-ene-1,4-dioate (107 mg equivalents of methyl hydrogen fumarate).

Blood samples were collected from all subjects prior to dosing, and at 0.5, 1, 1.5, 2, 3, 4, 5, 6, 7, 8, 10, 12, 16, 24, 30, 36, 48, 60, 72, 84, 96, 108 and 120 hours after dosing. Urine samples were collected from all subjects prior to dosing, and complete urine output was obtained at the 0-4, 4-8, 8-12, 12-24, 24-36, 36-48, 48-72, 72-96 and 96-120 hour intervals after dosing. Blood samples were quenched immediately with acetonitrile and frozen. Sample aliquots were prepared for analysis of (i) methyl hydrogen fumarate, (ii) (N,N-Diethylcarbamoyl)methyl methyl (2E)but-2-ene-1,4-dioate, (iii) N,N diethyl-2-hydroxy acetamide and (iv) (2S,3S,4S,5R,6R)-6-[(N,N-diethylcarbamoyl)methoxy]-3,4,5-trihydroxy-2H-3,4,5,6-tetrahydropyran-2-carboxylic acid, the latter two being other potential metabolites of (N,N-Diethylcarbamoyl)methyl methyl (2E)but-2-ene-1,4-dioate, using sensitive and specific LC/MS/MS methods.

Figure 2:
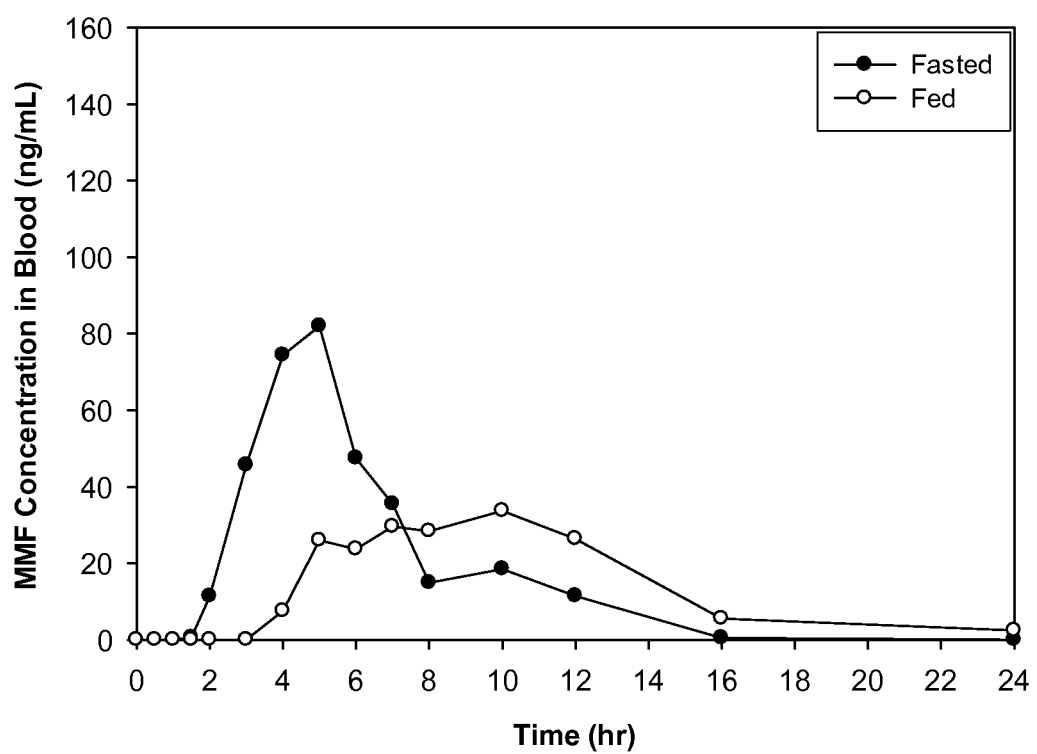
FIG. 2 shows the mean plasma concentration of MMF following the oral dosing of an enteric-coated sustained released tablet according to Example 1.

The plasma concentration of MMF following oral dosing of the formulation prepared according to Example 3 to fasted and fed healthy adult patients is shown in FIG. 2. Table 6 shows the preliminary mean (SD) pharmacokinetic data for (N,N-Diethylcarbamoyl)methyl methyl (2E)but-2-ene-1,4-dioate [Compound (1)] in fed and fasted patients.

TABLE 6

PK Data for Compound (1)

| N | Food | Average $C_{max}$ (ng/mL) | $T_{max}$ (hr) | $AUC_{inf}$ (ng · hr/mL) |
|---|---|---|---|---|
| 12*/8** | Fasted | 95* (26) | 4.17* (0.84) | 400** (166) |

TABLE 6-continued

PK Data for Compound (1)

| N | Food | Average $C_{max}$ (ng/mL) | $T_{max}$ (hr) | $AUC_{inf}$ (ng · hr/mL) |
|---|------|---------------------------|----------------|--------------------------|
| 12*/5*** | Fed | 80* (39) | 9.92* (5.50) | 377*** (132) |

*Cmax and Tmax measured in all 12 subjects,
**based on 8 out of 12 subjects with a defined terminal phase,
***based on 5 out of 12 subjects with a defined terminal phase The formulation produced mean (SD) maximum MMF concentrations (average Cmax) of 95 (26) ng/mL fasted and 80 (39) ng/mL fed. MMF AUC was 400 (160) ng*h/mL fasted and 377 (132) ng*h/mL fed. The time to peak concentration (Tmax) was 4.17 (0.84) hr fasted and 9.92 (5.50) hr fed. Promoiety was cleared from blood with a half-life around 3 hours.

(N,N-Diethylcarbamoyl)methyl methyl (2E)but-2-ene-1,4-dioate was well tolerated during the trial. All 12 subjects completed the dosing period. All adverse events were mild. One subject in the (N,N-Diethylcarbamoyl)methyl methyl (2E)but-2-ene-1,4-dioate fed group reported flushing more frequently than in the fed placebo group. No subjects in the fasted (N,N-Diethylcarbamoyl)methyl methyl (2E)but-2-ene-1,4-dioate group reported flushing, and no subjects in either the fed or fasted (N,N-Diethylcarbamoyl)methyl methyl (2E)but-2-ene-1,4-dioate groups reported feeling hot more than for placebo. A comparison of these adverse events of the formulation to placebo is shown in Table 7.

TABLE 7

Comparison of Adverse Events

| | Flushing | | Feeling Hot | |
|---|---|---|---|---|
| | Fasted | Fed | Fasted | Fed |
| Placebo | 0 | 1 | 0 | 0 |
| Example 3 Formulation | 1 | 1 | 0 | 0 |

Example 5

Preparation of VCaps Plus Capsule Dosage Form

Size 00 VCaps Plus capsules containing 477 mg of extended-release (N,N-Diethylcarbamoyl)methyl methyl (2E)but-2-ene-1,4-dioate-containing pellets were manufactured with the formulation shown in Table 8:

TABLE 8

Composition of VCaps Plus Capsule

| Component | Manufacturer | Role | Quantity (mg/tablet) | Quantity (% w/w) |
|---|---|---|---|---|
| (N,N-Diethylcarbamoyl)methyl methyl (2E)but-2-ene-1,4-dioate | Cambridge (Germantown, WI) | Drug substance | 200.00 | 60.00 |
| Microcrystalline Cellulose | FMC (Newark, DE) | Filler | 133.33 | 40.00 |
| | | Total Pellet Core | 333.33 | 100.00 |
| Ethylcellulose | Ashland (Hopewell VA) | Water-insoluble coating agent | 20.56 | 6.17 |
| Hydroxypropyl Cellulose | Ashland (Hopewell VA) | Water soluble coating agent | 5.00 | 1.50 |
| Talc | Luzenac (Houston TX) | Anti-tacking agent | 5.00 | 1.50 |
| Dibutyl sebacate | Vertellus (Greensboro, NC) | Plasticizer | 2.78 | 0.83 |
| | | Total Barrier/Sustained Release Coating | 33.33 | 10.00 |
| Methacrylic Acid Co-polymer Dispersion | Evonik (Darmstadt, Germany) | Enteric coating agent | 88.55 | 24.15 |
| Triethyl Citrate | Vertellus (Greensboro, NC) | Plasticizer | 14.30 | 3.90 |
| PlasACRYL T20 | Emerson (Norristown, PA) | Anti tacking agent | 7.15 | 1.95 |
| | | Total Enteric Coating | 110.00 | 30.00 |
| VCaps Plus Size 00 Capsule | Capsugel (Puebla, Mexico) | Capsule | 111-125 | 23.29-26.22 |

The capsules were manufactured according to the following process. An extrusion/spheronization process was selected for the manufacture of the core pellets for the capsules. The (N,N-Diethylcarbamoyl)methyl methyl (2E)but-2-ene-1,4-dioate was first screened then mixed with microcrystalline cellulose. This blend was then formed into a wet mass with the addition of aqueous acetate buffer (pH 3.5) and the mass then extruded through a 1.0 mm screen and the extrudates were spheronized (at 1200 rpm for 3 minutes) to form the core pellets. These core pellets are then classed to retain the pellets within 0.85 mm to 1.4 mm before the next processing step. The pellets were then coated with the target amount of the sustained release membrane using a hydroalcoholic mixture of ethylcellulose and hydroxypropyl cellulose. This coating was performed in a Wurster-type coater (product temperature at 30° C. and spray rate at 10 g/minute). The overall coating time was approximately 2 hours. The coated pellets were dried further in an oven to remove any residual solvent. The dried sustained release film-coated pellets were then enteric coated to the target amount by aqueous film coating in a Wurster-type coater (product temperature at 30° C. and a spray rate at 10 g/min). The overall coating time was approximately 2 hours. The capsules were then filled with the appropriate amount of pellets to achieve the desired dose strength.

Example 6

In Vitro Dissolution Profile of VCaps Plus Capsule Dosage Form

A two-stage dissolution method was used to determine the in vitro dissolution profile of dosage forms prepared according to Example 5 in order to mimic the conditions of a dosage form as it transits the gastrointestinal tract. Thus, the dosage forms were first placed into a dissolution medium having a pH of 1.2, to mimic the conditions of the stomach, and then placed into a dissolution medium of pH 6.8, to mimic the conditions of the intestines. The dissolution vessel (USP, Type I, basket) initially contained 750 mL of 0.1 N hydrochloric acid (pH 1.2). After 2 hours of dissolution, 250 mL of 200 mM tribasic sodium phosphate was added to the vessel resulting in a pH adjustment from 1.2 to 6.8. The dissolution medium was kept at 37° C. and was agitated at 100 rpm.

Samples of the dissolution medium were withdrawn at 1 and 2 hours following the start of the low pH stage, and at 0.5, 2, 4, 7, 10, and 14 hours following start of the near-neutral pH stage. The concentration of (N,N-Diethylcarbamoyl)methyl methyl (2E)but-2-ene-1,4-dioate in solution was determined using reverse phase HPLC using a C18 column and a phosphoric acid/acetonitrile/water isocratic mobile phase with photodiode detection at 210 nm.

Figure 3:
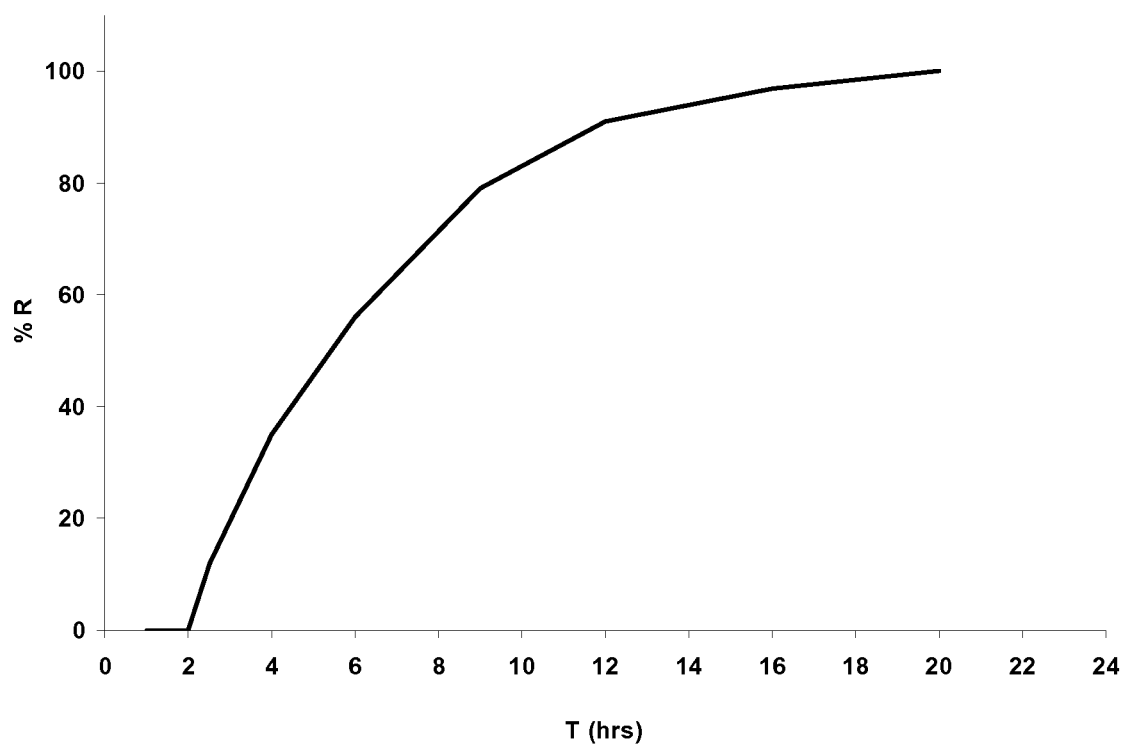
FIG. 3 shows the percent of prodrug released from the Example 5 dosage forms over time.

The percent of prodrug released from the Example 5 dosage forms over time is shown in FIG. 3. These dosage forms showed no prodrug release in the first 2 hours (acid stage) of testing. Slow prodrug release was observed after the dissolution medium pH was adjusted to 6.8. Full prodrug release was achieved after about 20 hours in pH 6.8.

Example 7

Safety, Tolerability, and Pharmacokinetics of Capsule Dosage Form

A randomized, double-blind crossover, food effect, single-dose study of the safety, tolerability, and pharmacokinetics of a sustained release oral dosage form of (N,N-Diethylcarbamoyl)methyl methyl (2E)but-2-ene-1,4-dioate in healthy adult subjects was conducted. Twelve healthy adult volunteers (males and females) participated in the study. All twelve subjects received a dosage form of Example 5, once in a fed condition and once in a fasted condition, with a two-week washout between treatments. The fasted dosing was achieved by dosing the subject following an overnight fast while the fed dosing was achieved by dosing the subject after consuming a high fat-content breakfast. The dosage form contains 200 mg of (N,N-Diethylcarbamoyl)methyl methyl (2E)but-2-ene-1,4-dioate (107 mg equivalents of methyl hydrogen fumarate).

Blood samples were collected from all subjects prior to dosing, and at 0.5, 1, 1.5, 2, 3, 4, 5, 6, 7, 8, 10, 12, 16, 24, 30, 36, 48, 60, 72, 84, 96, 108 and 120 hours after dosing. Urine samples were collected from all subjects prior to dosing, and complete urine output was obtained at the 0-4, 4-8, 8-12, 12-24, 24-36, 36-48, 48-72, 72-96 and 96-120 hour intervals after dosing. Blood samples were quenched immediately with acetonitrile and frozen. Sample aliquots were prepared for analysis of (i) methyl hydrogen fumarate, (ii) (N,N-Diethylcarbamoyl)methyl methyl (2E)but-2-ene-1,4-dioate, (iii) N,N diethyl-2-hydroxy acetamide and (iv) (2S,3S,4S,5R,6R)-6-[(N,N-diethylcarbamoyl)methoxy]-3,4,5-trihydroxy-2H-3,4,5,6-tetrahydropyran-2-carboxylic acid, the latter two being other potential metabolites of (N,N-Diethylcarbamoyl)methyl methyl (2E)but-2-ene-1,4-dioate, using sensitive and specific LC/MS/MS methods.

Figure 4:
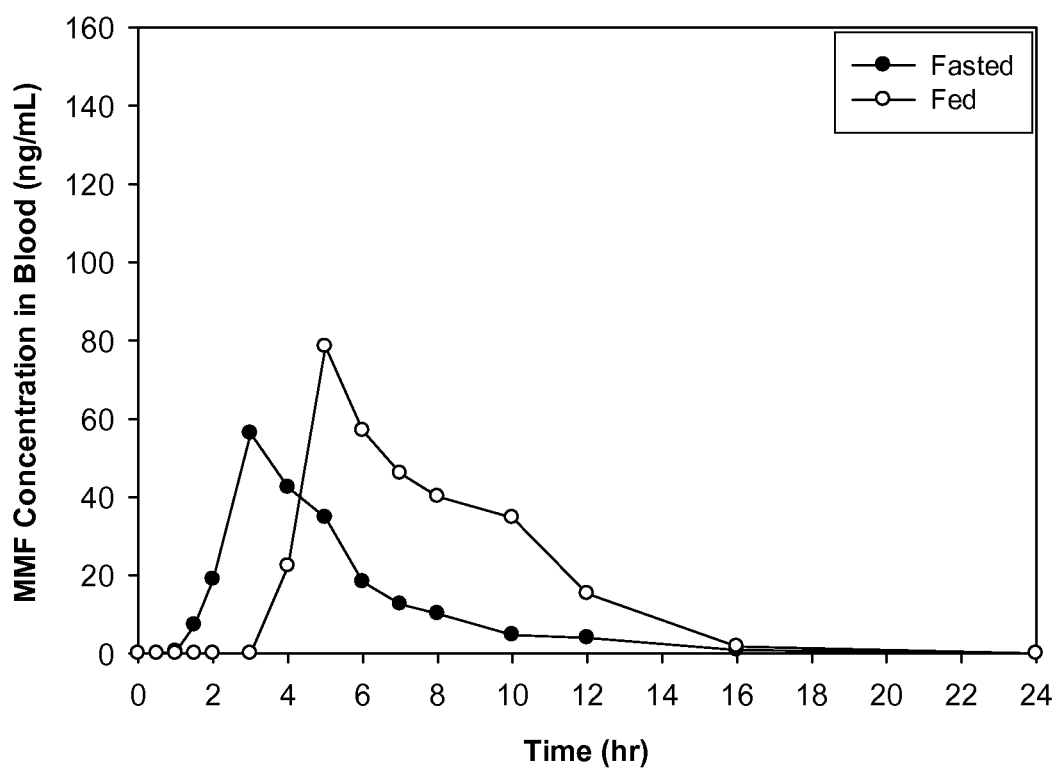
FIG. 4 shows the mean plasma concentration of MMF following oral dosing of a formulation prepared according to Example 6 to fasted and fed healthy adult patients.

The plasma concentration of MMF following oral dosing of the formulation prepared according to Example 5 to fasted and fed healthy adult patients is shown in FIG. 4. Table 9 shows the preliminary mean (SD) pharmacokinetic data for (N,N-Diethylcarbamoyl)methyl methyl (2E)but-2-ene-1,4-dioate in fed and fasted patients.

TABLE 9

| | | PK Data for Capsule Dosage Form | | |
|---|---|---|---|---|
| N | Food | Average $C_{max}$ (ng/mL) | $T_{max}$ (hr) | $AUC_{inf}$ (ng · hr/mL) |
| 12*/10** | Fasted | 64* (34) | 3.08* (0.79) | 257** (116) |
| 12 | Fed | 106 (37) | 6.42 (1.98) | 398 (123) |

*Cmax and Tmax measured in all 12 subjects,
**based on 10 out of 12 subjects with a defined terminal phase The formulation produced mean (SD) maximum MMF concentrations (average Cmax) of 64 (34) ng/mL fasted and 106 (37) ng/mL fed. MMF AUC was 257 (116) ng*h/mL fasted and 398 (123) ng*h/mL fed. The time to peak concentration (Tmax) was 3.08 (0.79) hr fasted and 6.42 (1.98) hr fed. Promoiety was cleared from blood with a half-life around 3 hours. (N,N-Diethylcarbamoyl)methyl methyl (2E)but-2-ene-1,4-dioate was well tolerated during the trial. All 12 subjects completed the dosing period. All adverse events were mild. Two subjects in the (N,N-Diethylcarbamoyl)methyl methyl (2E)but-2-ene-1,4-dioate fed group reported flushing more frequently than in the fed placebo group. No subjects in the fasted (N,N-Diethylcarbamoyl)methyl methyl (2E)but-2-ene-1,4-dioate group reported flushing, and no subjects in either the fed or fasted (N,N-Diethylcarbamoyl)methyl methyl (2E)but-2-ene-1,4-dioate groups reported feeling hot more than for placebo. A comparison of these adverse events of the formulation to placebo is shown in Table 10.

TABLE 10

| | Flushing | | Feeling Hot | |
|---|---|---|---|---|
| | Fasted | Fed | Fasted | Fed |
| Placebo | 0 | 1 | 0 | 0 |
| Example 5 Formulation | 2 | 0 | 0 | 0 |

Example 8

Preparation of Compression Coated Tablet Dosage Form (Non-Enteric Coated, 8% HPMC in Core)

Compression coated tablets containing (N,N-Diethylcarbamoyl)methyl methyl (2E)but-2-ene-1,4-dioate were made having the ingredients shown in Table 11:

TABLE 11

Composition of CCT Dosage Form (Non-Enteric Coated, 8% HPMC in Core)

| Component | Manufacturer | Role | Quantity (mg/tablet) | Quantity (% w/w) |
|---|---|---|---|---|
| (N,N-Diethylcarbamoyl)methyl methyl (2E)but-2-ene-1,4-dioate | XenoPort (Santa Clara, CA) | Drug substance | 100.00 | 29.19 |
| Hydroxypropyl Cellulose | Aqualon (Hopewell, VA) | Binder | 3.12 | 0.91 |
| Hypromellose 2208 (100000 mPa · s) | Dow Chemical (Midland, MI) | Sustained Release Polymer | 9.14 | 2.67 |
| Silicon Dioxide | Cabot (Tuscola, IL) | Glidant | 0.23 | 0.06 |
| Magnesium Stearate | Mallinckrodt (St. Louis, MO) | Lubricant | 1.71 | 0.50 |
| | | Total Core | 114.20 | 33.33 |
| Lactose Hydrate | Foremost (Rothschild, WI) | Filler | 157.60 | 46.00 |
| Hypromellose 2208 (100 mPa · s) | Dow Chemical (Midland, MI) | Sustained Release Polymer | 68.52 | 20.00 |
| Magnesium Stearate | Mallinckrodt (St. Louis, MO) | Lubricant | 2.28 | 0.67 |
| | | Total Mantle | 228.40 | 66.67 |
| | | Total Tablet | 342.60 | 100.00 |

The tablets were made according to the following steps. The core tablets were prepared using a wet granulation process. The granulation batch size was 680 g. (N,N-Diethylcarbamoyl)methyl methyl (2E)but-2-ene-1,4-dioate was passed through the Quadro Comil U5 with an 813 micron screen at 2000 rpm. Hydroxypropyl cellulose was passed through a 600 micron mesh screen. (N,N-Diethylcarbamoyl)methyl methyl (2E)but-2-ene-1,4-dioate and hydroxypropyl cellulose were granulated with purified water using a Diosna P1/6 equipped with a 4 L bowl. The wet granules were screened through an 1180 micron mesh screen and dried on trays in an oven at 30° C. for 6 hours.

The core blend batch size was 5 g. The dried granules, hydroxypropylmethylcellulose (i.e., hypromellose 2208 having 100000 mPa·s viscosity), and the silicon dioxide were then passed through a 600 micron mesh screen, combined in a glass jar and blended in a Turbula mixer for 5 minutes. Magnesium stearate was passed through a 250 micron screen and added to the blend before blending an additional 1.5 minutes. Core tablets (114.2 mg) were compressed using a Carver Press with ¼ inch (6.35 mm) round standard concave tooling at 0.4 metric ton (MT) force. The core tablets had a final hardness of approximately 7.6 kp (~74 Newtons).

The mantle blend was prepared using a direct compression process and a batch size of 10 g. The hypromellose 2208 (100 MPa·s viscosity) and lactose hydrate were passed through a 600 micron mesh screen, combined in a glass jar and blended in a Turbula mixer for 5 minutes. Magnesium stearate was passed through a 250 micron screen and added to the blend and blended an additional 1.5 minutes. The mantle blend was then applied to the core tablets using the Carver Press with ⅜ inch (9.53 mm) round standard concave tooling. Half the mantle blend (114.2 mg) was weighed out, added to the die, and tamped slightly to flatten. Then, the core tablet was placed into the die and pressed down gently into the mantle blend. The second half of the mantle blend (114.2 mg) was then added on top of the core tablet and the mantle was compressed using 1.5 MT force. The final compression coated tablets had a total weight of 342.6 mg with a (N,N-Diethylcarbamoyl)methyl methyl (2E)but-2-ene-1,4-dioate loading of 100 mg (29.19%). The tablets had a final hardness around 14.7 kp (~144 Newtons).

Example 9

Preparation of Compression Coated Tablet Dosage Form

Non-Enteric Coated, 30% HPMC in Mantle

Compression coated tablets containing (N,N-Diethylcarbamoyl)methyl methyl (2E)but-2-ene-1,4-dioate were made having the ingredients shown in Table 12:

TABLE 12

Composition of CCT Dosage Form (Non-Enteric Coated, 30% HPMC in Mantle)

| Component | Manufacturer | Role | Quantity (mg/tablet) | Quantity (% w/w) |
|---|---|---|---|---|
| (N,N-Diethylcarbamoyl)methyl methyl (2E)but-2-ene-1,4-dioate | XenoPort (Santa Clara, CA) | Drug substance | 100.00 | 31.78 |
| Hydroxypropyl Cellulose | Aqualon (Hopewell, VA) | Binder | 3.12 | 0.99 |
| Silicon Dioxide | Cabot (Tuscola, IL) | Glidant | 0.21 | 0.06 |
| Magnesium Stearate | Mallinckrodt (St. Louis, MO) | Lubricant | 1.57 | 0.50 |
| | | Total Core | 104.90 | 33.33 |
| Lactose Hydrate | Foremost (Rothschild, WI) | Filler | 144.76 | 46.00 |
| Hypromellose 2208 (100000 mPa · s) | Dow Chemical (Midland, MI) | Sustained Release Polymer | 62.94 | 20.00 |
| Magnesium Stearate | Mallinckrodt (St. Louis, MO) | Lubricant | 2.10 | 0.67 |
| | | Total Mantle | 209.80 | 66.67 |
| | | Total Tablet | 314.70 | 100.00 |

The tablets were made according to the following steps. The core tablets were prepared using a wet granulation process. The granulation batch size was 680 g. (N,N-Diethylcarbamoyl)methyl methyl (2E)but-2-ene-1,4-dioate was passed through the Quadro Comil U5 with an 813 micron screen at 2000 rpm. Hydroxypropyl cellulose was passed through a 600 micron mesh screen. (N,N-Diethylcarbamoyl)methyl methyl (2E)but-2-ene-1,4-dioate and hydroxypropyl cellulose were granulated with purified water using a Diosna P1/6 equipped with a 4 L bowl. The wet granules were screened through an 1180 micron mesh screen and dried on trays in an oven at 30° C. for 6 hours.

The core blend batch size was 5 g. The dried granules and the silicon dioxide were then passed through a 600 micron mesh screen, combined in a glass jar and blended in a Turbula mixer for 5 minutes. Magnesium stearate was passed through a 250 micron screen and added to the blend before blending an additional 1.5 minutes. Core tablets (104.9 mg) were compressed using a Carver Press with ¼ inch (6.35 mm) round standard concave tooling at 0.4 metric ton (MT) force. The core tablets had a final hardness of approximately 6.1 kp (~60 Newtons).

The mantle blend was prepared using a direct compression process and a batch size of 100 g. The hydroxypropylmethylcellulose (i.e., hypromellose 2208 having 100000 MPa·s viscosity) and lactose hydrate were passed through a 600 micron mesh screen, combined in a 1 quart (0.95 l) V-blender and blended for 10 minutes. Magnesium stearate was passed through a 250 micron screen and added to the blend and blended an additional 4 minutes. The mantle blend was then applied to the core tablets using the Carver Press with ⅜ inch (9.53 mm) round standard concave tooling. Half the mantle blend (104.9 mg) was weighed out, added to the die, and tamped slightly to flatten. Then, the core tablet was placed into the die and pressed down gently into the mantle blend. The second half of the mantle blend (104.9 mg) was then added on top of the core tablet, and the mantle was compressed using 1.5 MT force. The final compression coated tablets had a total weight of 314.7 mg with a (N,N-Diethylcarbamoyl)methyl methyl (2E)but-2-ene-1,4-dioate loading of 100 mg (31.78%). The tablets had a final hardness around 13.1 kp (~128 Newtons).

Example 10

Composition of CCT Dosage Form (Non-Enteric Coated, 8% HPMC in Core)

Compression coated tablets containing (N,N-Diethylcarbamoyl)methyl methyl (2E)but-2-ene-1,4-dioate were made having the ingredients shown in Table 13:

TABLE 13

Composition of CCT Dosage Form (Non-Enteric Coated, 8% HPMC in Core)

| Component | Manufacturer | Role | Quantity (mg/tablet) | Quantity (% w/w) |
|---|---|---|---|---|
| (N,N-Diethylcarbamoyl)methyl methyl (2E)but-2-ene-1,4-dioate | Cambridge Major (Germantown, WI) | Drug substance | 100.0 | 27.59 |
| Hydroxypropyl Cellulose | Aqualon (Hopewell, VA) | Binder | 3.1 | 0.86 |
| Hypromellose 2208 (100000 mPa·s) | Dow Chemical (Midland, MI) | Sustained Release Polymer | 9.1 | 2.51 |
| Silicon Dioxide | Evonik (Rheinfelden, Germany) | Glidant | 0.6 | 0.17 |
| Magnesium Stearate | Mallinckrodt (St. Louis, MO) | Lubricant | 1.7 | 0.47 |
| | | Total Core | 114.5 | 31.59 |
| Lactose Hydrate | Foremost (Rothschild, WI) | Filler | 164.8 | 45.47 |
| Hypromellose 2208 (100 mPa·s) | Dow Chemical (Midland, MI) | Sustained Release Polymer | 80.6 | 22.24 |
| Magnesium Stearate | Mallinckrodt (St. Louis, MO) | Lubricant | 2.5 | 0.69 |
| | | Total Mantle | 247.9 | 68.41 |
| | | Total Tablet | 362.4 | 100.00 |

The tablets were made according to the following steps. The core tablets were prepared using a wet granulation process. The granulation was performed in 2 batches at 494.88 g each. (N,N-Diethylcarbamoyl)methyl methyl (2E)but-2-ene-1,4-dioate was passed through a 1.0 mm mesh screen. Hydroxypropyl cellulose was passed through a 600 micron mesh screen. (N,N-Diethylcarbamoyl)methyl methyl (2E)but-2-ene-1,4-dioate and hydroxypropyl cellulose were combined in a 3 L bowl and mixed for 10 minutes using the Quintech granulator. The mixture was then transferred to a 2 L bowl granulated with purified water using the Quintech granulator. The wet granules were screened through a 2000 micron mesh screen and dried on trays in an oven at 30° C. for 4 hours 20 minutes. The dried granules were then passed through an 850 micron screen.

The core blend batch size was 1099.2 g. The hydroxypropylmethyl-cellulose (i.e., Hypromellose 2208 having 100000 mPa·s viscosity) and the silicon dioxide were combined, passed through a 600 micron mesh screen, and added to the dry granules in a 5 L cube blender and blended for 10 minutes at 25 rpm. Magnesium stearate was passed through a 600 micron screen and added to the blend before blending an additional 4 minutes at 25 rpm. Core tablets (114.5 mg) were compressed using a Manesty F3 tablet press with 6.0 mm round concave tooling. The core tablets had a final mean hardness between 8.1 to 10.2 kp (79-100 Newtons).

The mantle blend was prepared using a direct compression process and a batch size of 5.0 kg. The hypromellose 2208 (100 MPa·s viscosity) and lactose hydrate were combined and passed through a 600 micron mesh screen, placed in and blended on the Tumblemix 18 L Bin Blender for 8.5 minutes at 30 rpm. Magnesium stearate was passed through a 600 micron screen and added to the blend and blended an additional 3.5 minutes. The mantle blend was then applied to the core tablets using a Kikusui tablet press (Kikusui Seisakusho Ltd., Kyoto, Japan) specially designed for the manufacture of compression coated tablets. Compression was completed using 9.5 mm round concave tooling and approximately 1000 kp force. The final compression coated tablets had a total weight of 362.4 mg with a (N,N-Diethylcarbamoyl)methyl methyl (2E)but-2-ene-1,4-dioate loading of 100 mg (27.59%). The compression coated tablets had a final mean hardness between 10.9 to 14.0 kp (107-137 Newtons).

Example 11

In Vitro Dissolution Profile of Compression Coated Tablet Dosage Forms

A two-stage dissolution method was used to determine the in vitro dissolution profile of dosage forms prepared according to Examples 8, 9, and 10 in order to mimic the conditions of a dosage form as it transits the gastrointestinal tract. Thus, the dosage forms were first placed into a dissolution medium having a pH of 1.2, to mimic the conditions of the stomach, and then placed into a dissolution medium of pH 6.8, to mimic the conditions of the intestines. The dissolution vessel (USP, Type I, basket) initially contained 750 mL of 0.1 N hydrochloric acid (pH 1.2). After 2 hours of dissolution, 250 mL of 200 mM tribasic sodium phosphate was added to the vessel resulting in a pH adjustment from 1.2 to 6.8. The dissolution medium was kept at 37° C. and was agitated at 100 rpm.

For the tested dosage forms, samples of the dissolution medium were withdrawn at the indicated time points shown in the respective figures. The amount of (N,N-Diethylcarbamoyl)methyl methyl (2E)but-2-ene-1,4-dioate in the dissolution medium samples was determined by reverse phase HPLC using a C18 column and a 7 minute gradient method according to Table 14 where Mobile Phase A is water/0.1% $H_3PO_4$ and Mobile Phase B is water/acetonitrile/$H_3PO_4$ (10/90/0.1 by volume) with UV detection at 210 nm.

TABLE 14

HPLC Gradient Conditions

| Time (minute) | % Mobile Phase A | % Mobile Phase B |
|---|---|---|
| 0 | 85 | 15 |
| 5 | 35 | 65 |
| 5.5 | 85 | 15 |
| 7 | 85 | 15 |

Figure 5:
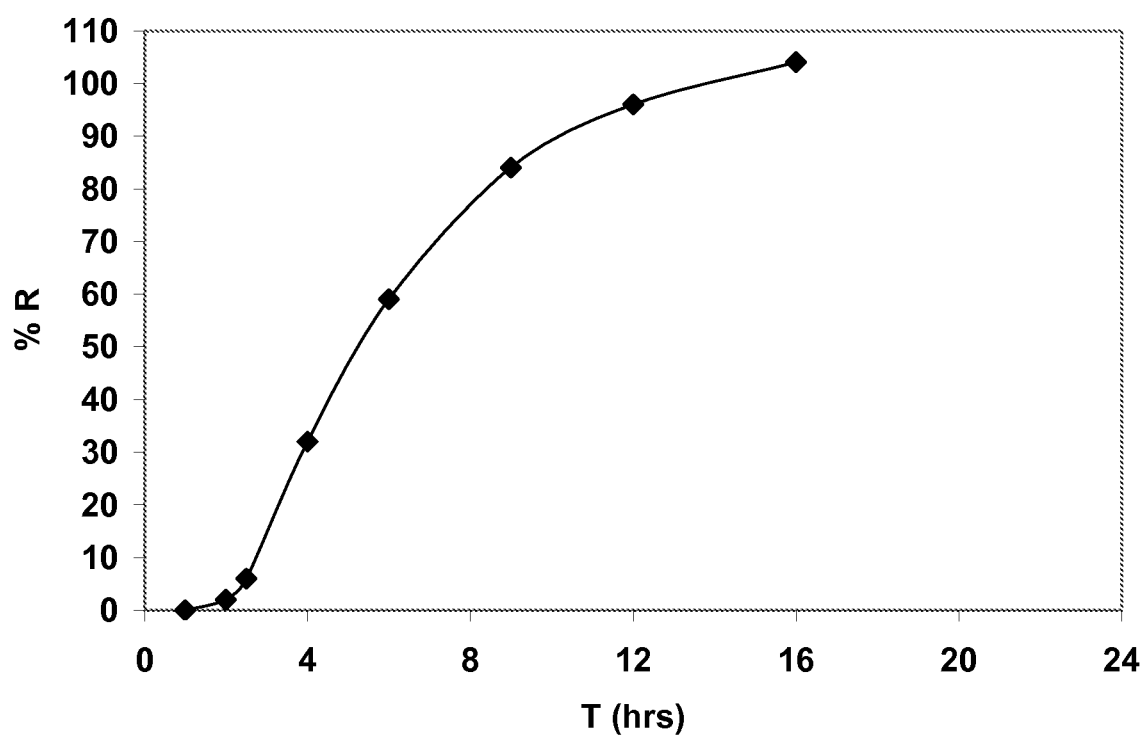
FIG. 5 shows the percent of prodrug released from the Example 8 dosage forms over time.

As shown in FIG. 5, for dosage forms prepared according to Example 8, drug release is delayed for approximately 2 hours, and thereafter the drug is released gradually, reaching more than 90% released at 16 hours.

Figure 6:
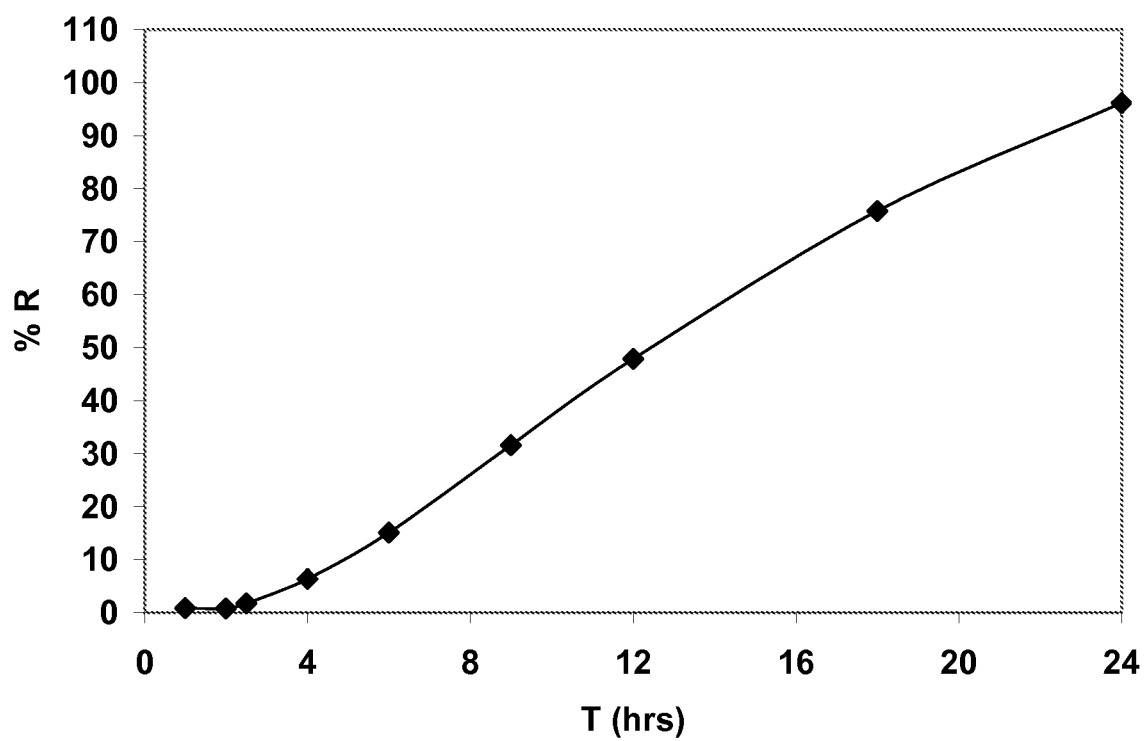
FIG. 6 shows the percent of prodrug released from the Example 9 dosage forms over time.

As shown in FIG. 6, for dosage forms prepared according to Example 9, drug release is delayed for approximately 2 hours, followed by near zero order release, reaching more than 90% released at 24 hours.

Figure 7:
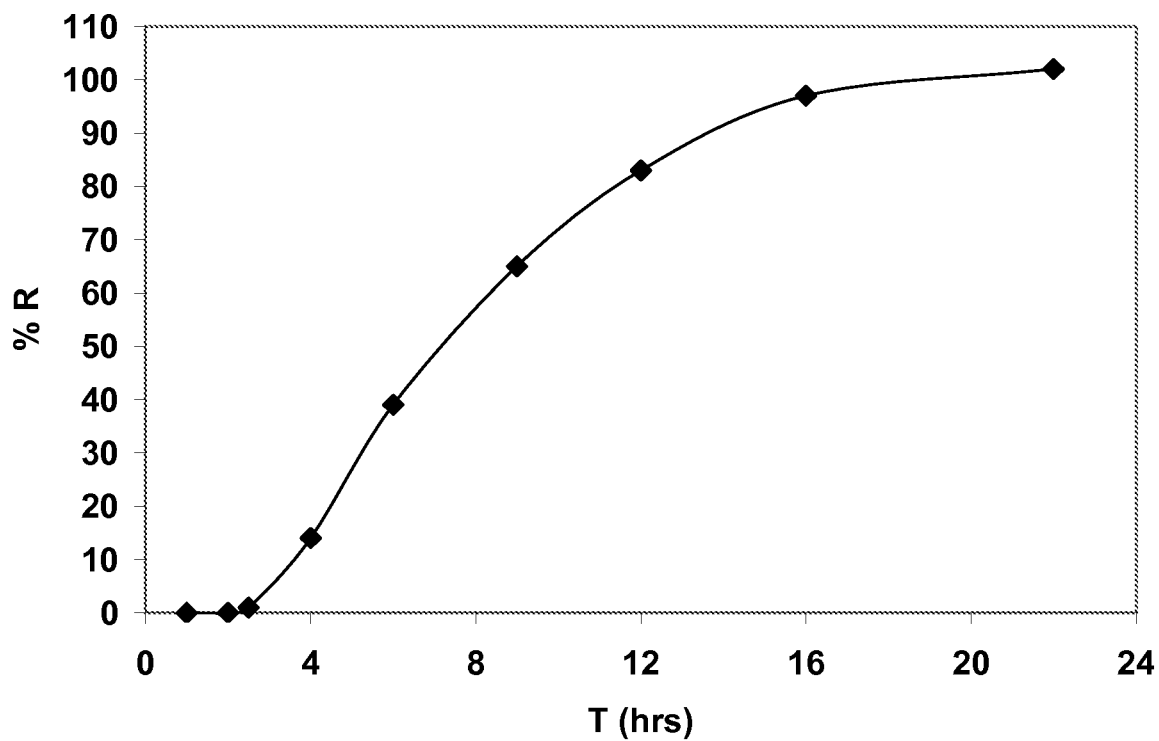
FIG. 7 shows the percent of prodrug released from the Example 10 dosage forms over time.

As shown in FIG. 7, for dosage forms prepared according to Example 10, drug release is delayed for approximately 2 hours, and thereafter the drug is released gradually, reaching more than 90% released at 16 hours.

Example 12

Preparation of Compression Coated Tablet Dosage Form

Non-Enteric Coated, 10% HPMC in the Core

To demonstrate the effect of increasing the percentage of sustained release polymer in the core on the in vitro dissolution profile, two different tablet formulations were made according to the procedure outlined in Example 8, but with differing levels of hypromellose 2208 (100000 MPa·s viscosity) in the core, i.e., compared to the Example 8 tablets. Thus, the Example 8 tablets contained 8 wt % HPMC in the core while the Example 12 tablets contained 10 wt % HPMC in the core, respectively. The tablet formulations, including the Example 8 tablet formulation for reference, are shown in Table 15.

TABLE 15

Composition of CCT Dosage Forms (Non-Enteric Coated, 8% and 10% HPMC in Core)

| | Quantity (mg/tablet) | Quantity (% w/w) | Quantity (mg/tablet) | Quantity (% w/w) |
|---|---|---|---|---|
| Component | Example 8 | | Example 12 | |
| (N,N-Diethylcarbamoyl)methyl methyl (2E)but-2-ene-1,4-dioate | 100.00 | 29.19 | 100.00 | 28.55 |
| Hydroxypropyl Cellulose | 3.12 | 0.91 | 3.10 | 0.88 |
| Hypromellose 2208 (100000 mPa · s) | 9.14 | 2.67 | 11.67 | 3.33 |
| Silicon Dioxide | 0.23 | 0.06 | 0.23 | 0.07 |
| Magnesium Stearate | 1.71 | 0.50 | 1.75 | 0.50 |
| Total Core | 114.20 | 33.33 | 116.75 | 33.33 |
| Lactose Hydrate | 157.60 | 46.00 | 161.12 | 46.00 |
| Hypromellose 2208 (100 mPa · s) | 68.52 | 20.00 | 70.05 | 20.00 |
| Magnesium Stearate | 2.28 | 0.67 | 2.33 | 0.67 |
| Total Mantle | 228.40 | 66.67 | 233.50 | 66.67 |
| Total Tablet | 342.60 | 100.00 | 350.25 | 100.00 |

Figure 8:
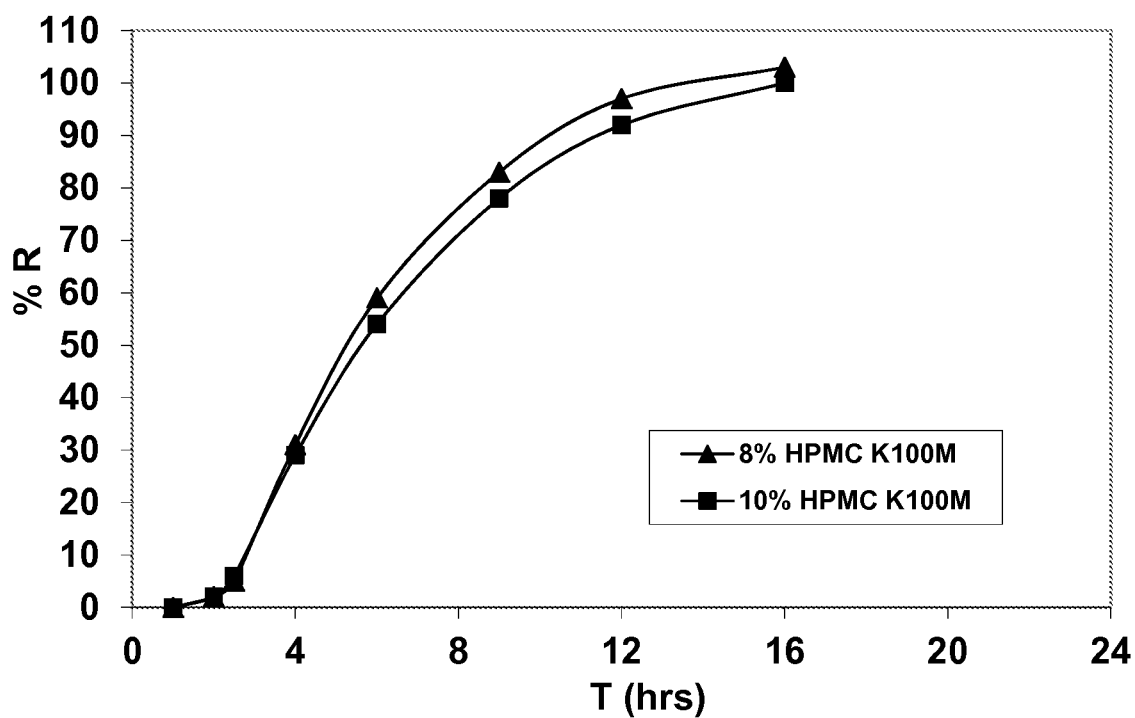
FIG. 8 shows the percent of prodrug released from the two Example 12 dosage forms over time.

The dissolution profiles from the three compression coated tablets were measured according to the method described in Example 11. FIG. 8 shows that the MHF prodrug release rate slows with increasing percentage of hypromellose 2208 (100000 mPa·s) in the core, but the initial delay before the start of prodrug release stays the same at approximately 2 hours, likely due to the unchanged mantle layer.

Example 13

Preparation of Sustained Release Tablet Dosage Forms (Non-Enteric Coated)

To demonstrate the effect of increasing the viscosity of sustained release polymer in the mantle on the in vitro dissolution profile, tablets were made with hypromellose 2208 of different viscosities in the mantle: Example 13a (4000 mPa·s), and Example 13b (a combination of 100 mPa·s and 4000 mPa·s to give an effective viscosity of ~2000 mPa·s). The formulation details are shown in Table 16.

TABLE 16

Composition of Sustained Release Tablet Dosage Forms (Non-Enteric Coated)

| Component | Quantity (mg/tablet) Example 13a | Quantity (% w/w) Example 13a | Quantity (mg/tablet) Example 13b | Quantity (% w/w) Example 13b |
|---|---|---|---|---|
| (N,N-Diethylcarbamoyl)methyl methyl (2E)but-2-ene-1,4-dioate | 200.00 | 32.00 | 200.00 | 32.00 |
| Hydroxypropyl Cellulose | 6.20 | 1.00 | 6.20 | 1.00 |
| Magnesium Stearate | 2.10 | 0.30 | 2.10 | 0.30 |
| Total Core | 208.30 | 33.30 | 208.30 | 33.30 |
| Lactose Hydrate | 308.30 | 49.30 | 308.30 | 49.30 |
| Hypromellose 2208 (100 mPa · s) | 0.00 | 0.00 | 52.05 | 8.35 |
| Hypromellose 2208 (4000 mPa · s) | 104.10 | 16.70 | 52.05 | 8.35 |
| Magnesium Stearate | 4.20 | 0.70 | 4.20 | 0.70 |
| Total Mantle | 416.60 | 66.70 | 416.60 | 66.70 |
| Total Tablet | 624.90 | 100.00 | 624.90 | 100.00 |

The tablets were made according to the following steps. The core tablets were prepared using a wet granulation process. The granulation batch size was 170 g. (N,N-Diethylcarbamoyl)methyl methyl (2E)but-2-ene-1,4-dioate was passed through the Quadro Comil U5 with an 813 micron screen at 2000 rpm. Hydroxypropyl cellulose was passed through a 500 micron mesh screen. (N,N-Diethylcarbamoyl)methyl methyl (2E)but-2-ene-1,4-dioate and hydroxypropyl cellulose were granulated with purified water using a Diosna P1/6 equipped with a 1 L bowl. The wet granules were screened through an 1180 micron mesh screen and dried on trays in an oven at 30° C. for 3 hours 48 minutes.

The core blend batch size was 20.0 g. The dried granules and magnesium stearate were combined in a glass bottle and blended in a Turbula mixer for 2 minutes. Core tablets (208.3 mg) were compressed using a Manesty FlexiTab single station tablet press with 5/16 inch (7.9 mm) round standard concave tooling at forces ranging from 9.9 to 14.0 kN. The core tablets had a final mean hardness of 8.4 kp (~82 Newtons).

The mantle blend was prepared using a direct compression process and a batch size of either 10 g (Example 13b) or 20 g (Example 13a). The hypromellose 2208 and lactose hydrate were passed through a 600 micron mesh screen, combined in a glass bottle and blended in a Turbula mixer for either 10 (Example 13a), or 5 (Example 13b) minutes. In each case, magnesium stearate was passed through a 250 micron screen and added to the blend and blended an additional 1.5 minutes. The mantle blend was then applied to the core tablets using the Carver Press with 7/16 inch (11.1 mm) round standard concave tooling. Half the mantle blend (208.3 mg) was weighed out, added to the die, and tamped slightly to flatten. Then, the core tablet was placed into the die and pressed down gently into the mantle blend. The second half of the mantle blend (208.3 mg) was then added on top of the core tablet and the mantle was compressed using 2.0 metric ton (MT) force. The final compression coated tablets had a total weight of 624.9 mg with a (N,N-Diethylcarbamoyl)methyl methyl (2E)but-2-ene-1,4-dioate loading of 200 mg (32.00%). The tablets had a final hardness of about 18.3 to 19.5 kp (~179 to 191 Newtons).

Figure 9:
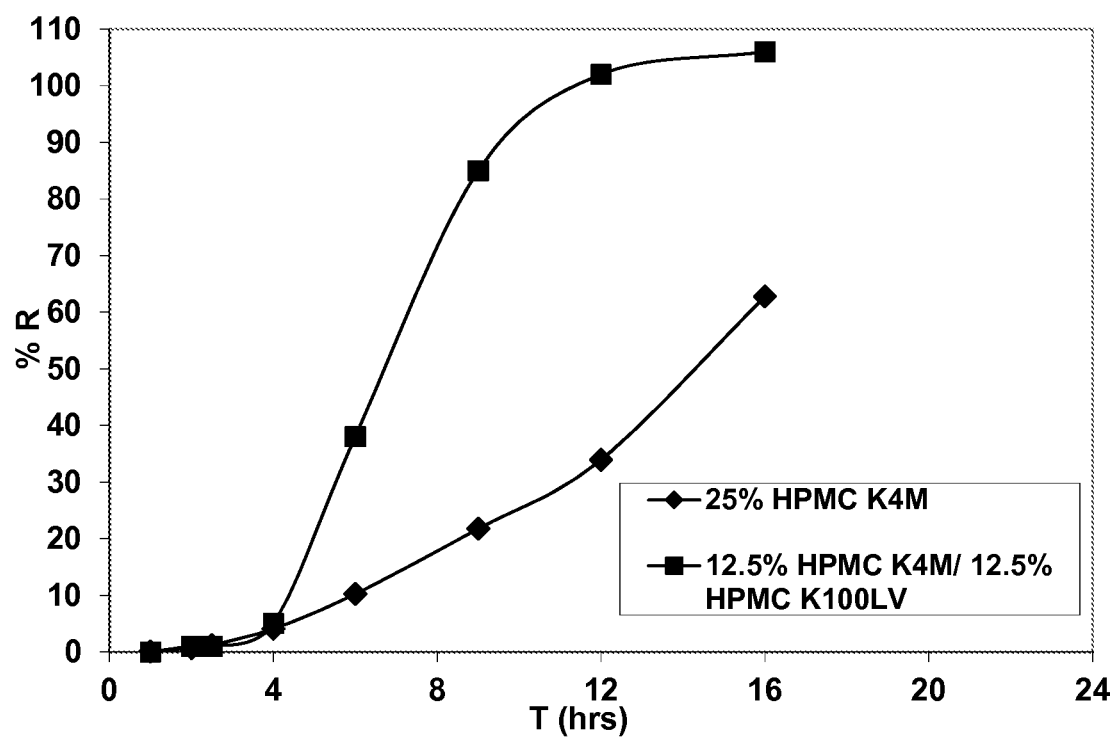
FIG. 9 shows the percent of prodrug released from the two Example 13 dosage forms over time.

The dissolution profiles from the two compression coated tablets were measured according to the method described in Example 11. FIG. 9 shows that the MHF prodrug release rate slows with increasing hypromellose viscosity and the delay time increases slightly with increasing hypromellose viscosity.

Example 14

Preparation of Sustained Release Tablet Dosage Forms

Non-Enteric Coated with 5 wt % Hypromellose 2208 (100000 mPa·s) in the Core and 40% Hypromellose 2208 (100 mPa·s) in the Mantle To demonstrate the effect of increasing the percentage of hypromellose 2208 (100 mPa·s viscosity) in the mantle on the in vitro dissolution profile and reducing the amount of hypromellose 2208 (100000 mPa·s) in the core, tablets were made according to the procedure outlined in Example 8, but with 5 wt % hypromellose 2208 (100000 mPa·s) in the core and 40% of hypromellose 2208 (100 MPa·s) in the mantle: The tablet formulation is shown in Table 17.

TABLE 17

Composition of SR Tablet Dosage Forms
[Non-Enteric Coated with 5 wt % hypromellose 2208 (100000 mPa · s) in the core and 40% hypromellose 2208 (100 MPa · s) in the mantle]

| Component | Quantity (mg/tablet) Example 14 | Quantity (% w/w) Example 14 |
|---|---|---|
| (N,N-Diethylcarbamoyl)methyl methyl(2E)but-2-ene-1,4-dioate | 100.00 | 30.17 |
| Hydroxypropyl Cellulose | 3.10 | 0.93 |
| Hypromellose 2208 (100000 mPa · s) | 5.52 | 1.66 |
| Silicon Dioxide | 0.22 | 0.07 |
| Magnesium Stearate | 1.66 | 0.50 |
| Total Core | 110.50 | 33.33 |
| Lactose Hydrate | 130.39 | 39.33 |
| Hypromellose 2208 (100 mPa · s) | 88.40 | 26.67 |
| Magnesium Stearate | 2.21 | 0.67 |
| Total Mantle | 221.00 | 66.67 |
| Total Tablet | 331.50 | 100.00 |

Figure 10:
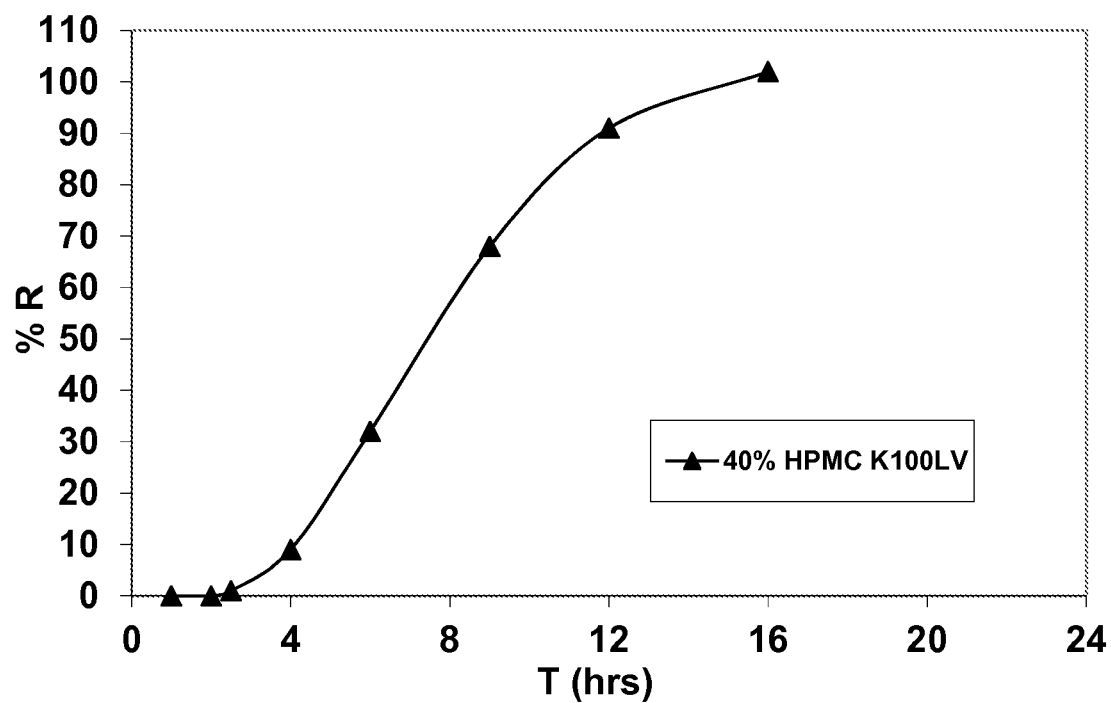
FIG. 10 shows the percent of prodrug released from the Example 14 dosage form over time.

The dissolution profile from the Example 14 compression coated tablets was measured according to the method described in Example 11. FIG. 10 shows that the delay to drug release is increased with increasing percentage of hypromellose 2208 (100 mPa·s) in the mantle, and the rate of MHS prodrug increases slightly with decreasing percentage of hypromellose 2208 (100000 mPa·s) in the core.

Example 15

Preparation of Sustained Release Tablet Dosage Forms

Non-Enteric Coated Formulation with No Hypromellose in the Core and Thin Mantle

To demonstrate the effect of decreasing the thickness of the mantle on the in vitro dissolution profile, the mantle to core weight ratio was decreased from 2 to 1.5. The tablet formulation is shown in Table 18.

TABLE 18

Composition of SR Tablet Dosage Form (Non-Enteric Coated)

| Component | Quantity (mg/tablet) Example 15 | Quantity (% w/w) |
|---|---|---|
| (N,N-Diethylcarbamoyl)methyl methyl(2E)but-2-ene-1,4-dioate | 100.00 | 38.37 |
| Hydroxypropyl Cellulose | 3.06 | 1.17 |
| Silicon Dioxide | 0.10 | 0.04 |
| Magnesium Stearate | 1.04 | 0.40 |
| Total Core | 104.20 | 40.00 |
| Lactose Hydrate | 107.8 | 41.40 |
| Hypromellose 2208 (100000 mPa·s) | 46.9 | 18.00 |
| Magnesium Stearate | 1.56 | 0.60 |
| Total Mantle | 156.40 | 66.70 |
| Total Tablet | 260.60 | 100.00 |

The tablets were made according to the following steps. The core tablets were prepared using a wet granulation process. The granulation batch size was 680 g. (N,N-Diethylcarbamoyl)methyl methyl (2E)but-2-ene-1,4-dioate was passed through the Quadro Comil U5 with an 813 micron screen at 2000 rpm. Hydroxypropyl cellulose was passed through a 600 micron mesh screen. (N,N-Diethylcarbamoyl)methyl methyl (2E)but-2-ene-1,4-dioate and hydroxypropyl cellulose were granulated with purified water using a Diosna P1/6 equipped with a 4 L bowl. The wet granules were screened through an 1180 micron mesh screen and dried on trays in an oven at 30° C. for 6 hours.

The core blend batch size was 30.0 g. The dried granules and the silicon dioxide were then passed through a 600 micron mesh screen, combined in a glass jar and blended in a Turbula mixer for 2 minutes. Magnesium stearate was passed through a 250 micron screen and added to the blend before blending an additional 1.5 minutes. Core tablets (104.2 mg) were compressed using a Manesty FlexiTab single station tablet press with ¼ inch (6.35 mm) round standard concave tooling at approximately 3 kN force. The core tablets had a final hardness of 6.2 to 7.0 kp (about 61 to 69 Newtons).

The mantle blend was prepared using a direct compression process and a batch size of 10 g. The hypromellose 2208 (100000 MPa·s) and lactose hydrate were passed through a 600 micron mesh screen, combined in a glass bottle and blended for 5 minutes in a Turbula mixer. Magnesium stearate was passed through a 250 micron screen and added to the blend and blended an additional 1.5 minutes. The mantle blend was then applied to the core tablets using the Carver Press with 5/16 inch (7.94 mm) round standard concave tooling. Half the mantle blend (78.2 mg) was weighed out, added to the die, and tamped slightly to flatten. Then, the core tablet was placed into the die and pressed down gently into the mantle blend. The second half of the mantle blend (78.2 mg) was then added on top of the core tablet and the mantle was compressed using 1.1 metric ton (MT) force. The final compression coated tablets had a total weight of 260.6 mg with a (N,N-Diethylcarbamoyl)methyl methyl (2E)but-2-ene-1,4-dioate loading of 100 mg (38.37%). The tablets had a final hardness ranging from 13.1 to 14.0 kp (about 128 to 137 Newtons).

Figure 11:
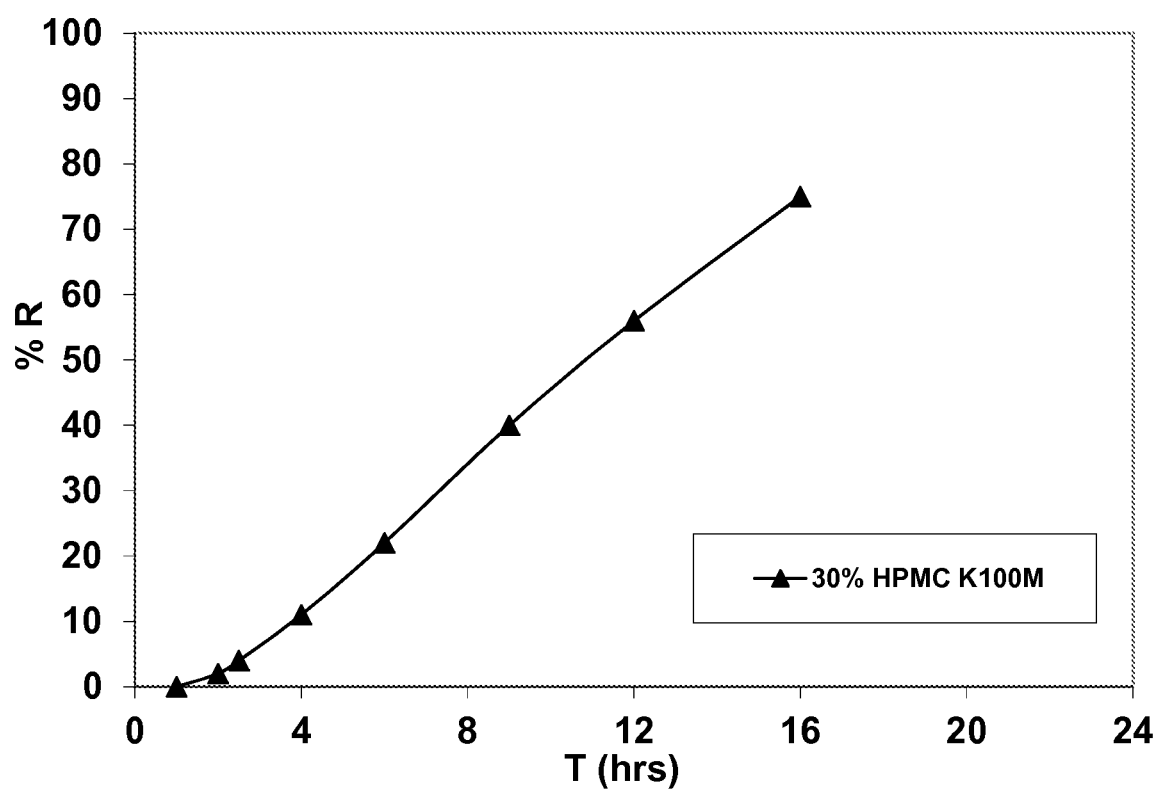
FIG. 11 shows the percent of prodrug released from the Example 15 dosage form over time.

The dissolution profile from the compression coated tablets was measured according to the method described in Example 11. FIG. 11 shows that the release of drug substance from the tablet increases with decreasing mantle to core weight ratio (compare with Example 9 and FIG. 6).

Example 16

Safety, Tolerability, and Pharmacokinetics of Example 10 Dosage Form

A randomized, double-blind crossover, food effect, single-dose study of the safety, tolerability, and pharmacokinetics of an oral dosage form of (N,N-Diethylcarbamoyl)methyl methyl (2E)but-2-ene-1,4-dioate in healthy adult subjects was conducted. Twelve healthy adult volunteers (males and females) participated in the study. All twelve subjects received a dosage form of Example 10, once in a fed condition and once in a fasted condition, with a two-week washout between treatments. The fasted dosing was achieved by dosing the subject following an overnight fast while the fed dosing was achieved by dosing the subject after consuming a high fat-content breakfast. The dosage form contained 100 mg of (N,N-Diethylcarbamoyl)methyl methyl (2E)but-2-ene-1,4-dioate (54 mg equivalents of methyl hydrogen fumarate).

Blood samples were collected from all subjects prior to dosing, and at 0.5, 1, 1.5, 2, 3, 4, 5, 6, 7, 8, 10, 12, 16, 24, 30, 36, 48, 60, 72, 84, 96, 108 and 120 hours after dosing. Urine samples were collected from all subjects prior to dosing, and complete urine output was obtained at the 0-4, 4-8, 8-12, 12-24, 24-36, 36-48, 48-72, 72-96 and 96-120 hour intervals after dosing. Blood samples were quenched immediately with acetonitrile and frozen. Sample aliquots were prepared for analysis of (i) methyl hydrogen fumarate, (ii) (N,N-Diethylcarbamoyl)methyl methyl (2E)but-2-ene-1,4-dioate, (iii) N,N diethyl-2-hydroxy acetamide and (iv) (2S,3S,4S,5R,6R)-6-[(N,N-diethylcarbamoyl)methoxy]-3,4,5-trihydroxy-2H-3,4,5,6-tetrahydropyran-2-carboxylic acid, the latter two being other potential metaboliltes of (N,N-Diethylcarbamoyl)methyl methyl (2E)but-2-ene-1,4-dioate, using sensitive and specific LC/MS/MS methods.

Figure 12:
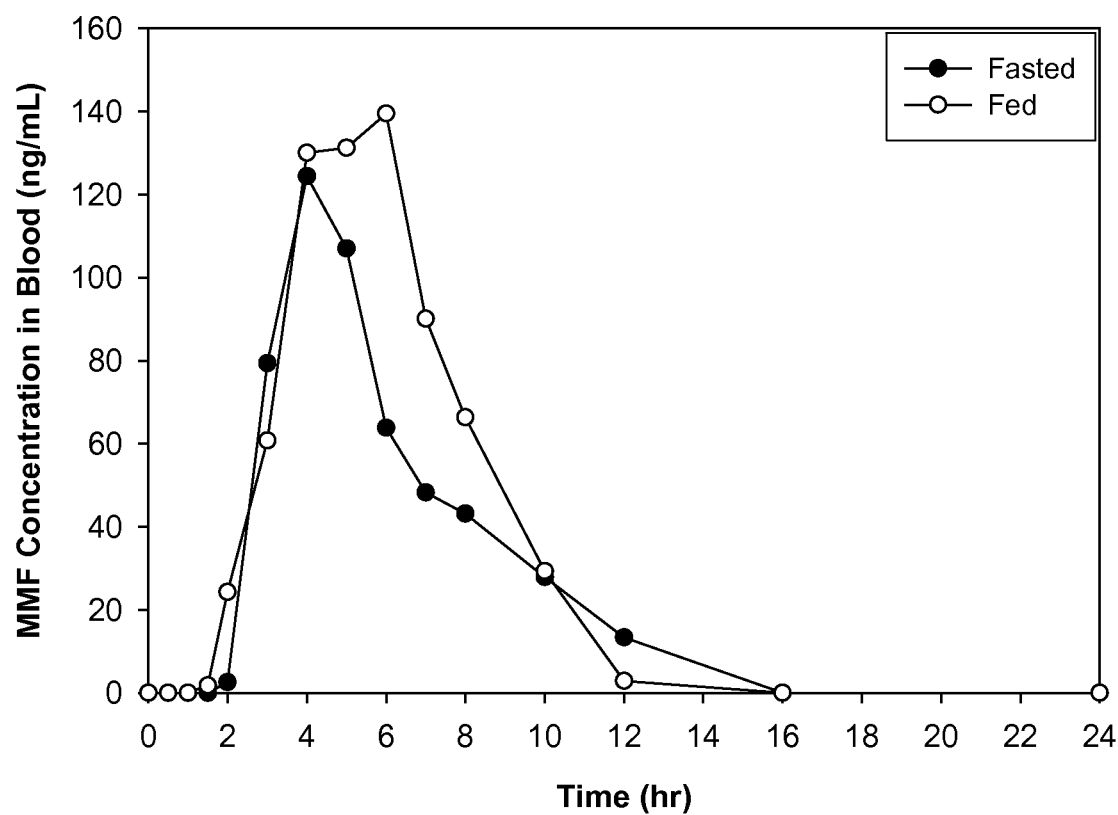
FIG. 12 shows the mean plasma concentration of MMF following oral dosing of a formulation prepared according to Example 10 to fasted and fed healthy adult patients.

The plasma concentration of MMF following oral dosing of the formulation prepared according to Example 10 to fasted and fed healthy adult patients is shown in FIG. 12. Table 19 shows the preliminary mean (SD) pharmacokinetic data for (N,N-diethylcarbamoyl)methyl methyl (2E)but-2-ene-1,4-dioate in fed and fasted patients.

TABLE 19

PK Data for Example 10 Dosage Form

| N | Food | Average $C_{max}$ (ng/mL) | $AUC_{inf}$ (ng·hr/mL) |
|---|---|---|---|
| 12 | Fasted | 143 (61.1) | 625 (216) |
| 12 | Fed | 217 (88.5) | 750 (242) |

MMF release from the formulation was sustained and minimally affected by food. The formulation produced mean (SD) maximum MMF concentrations (average Cmax) 143 (61) ng/mL fasted and 217 (89) ng/mL fed. MMF AUC was 625 (216) ng·h/mL fasted and 750 (242) ng·h/mL fed. Promoiety was cleared from blood with a half-life around 3 hours. (N,N-Diethylcarbamoyl)methyl methyl (2E)but-2-ene-1,4-dioate was well tolerated during the trial. All 12 subjects completed the dosing period. All adverse events were mild. Adverse events that were reported in more than one subject and that were more frequently for (N,N-Diethylcarbamoyl)methyl methyl (2E)but-2-ene-1,4-dioate than for placebo were flushing and feeling hot. A comparison of these adverse events to placebo is shown in Table 20.

TABLE 20

| | Comparison of Adverse Events | | | |
|---|---|---|---|---|
| | Flushing | | Feeling Hot | |
| | Fasted | Fed | Fasted | Fed |
| Placebo | 0 | 1 | 0 | 0 |
| Formulation | 0 | 1 | 0 | 0 |

Finally, it should be noted that there are alternative ways of implementing the embodiments disclosed herein. Accordingly, the present embodiments are to be considered as illustrative and not restrictive, and the claims are not to be limited to the details given herein, but may be modified within the scope and equivalents thereof.

The invention claimed is:

1. A method of systemically administering a therapeutically effective amount of (N,N-diethylcarbamoyl)methyl methyl (2E)but-2-ene-1,4-dioate to treat a disease in each patient of a population of patients in need of such treatment, comprising administering an oral sustained release tablet consisting of (i) a core comprising (N,N-diethylcarbamoyl) methyl methyl (2E)but-2-ene-1,4-dioate and hydroxypropyl methyl-cellulose, wherein hydroxypropyl methyl-cellulose is from 8% to 10% by weight of the core and (ii) a compression-coated mantle layer comprising a sustained release polymer layer of hydroxypropyl methylcellulose surrounding the core, wherein the hydroxypropyl methyl-cellulose is from 30% to 32.5% by weight of the mantle, wherein the tablet does not contain an enteric coating,
the disease is selected from multiple sclerosis and psoriasis; and
the tablet, when subjected to an in vitro dissolution test employing as a dissolution medium 750 mL of 0.1N hydrochloric acid, at pH 1.2, for a period of 2 hours, followed by addition of 250 mL of 200 mM tribasic sodium phosphate buffer resulting in an adjustment of the pH of the dissolution medium to 6.8, the dissolution medium being maintained at 37° C. and stirred at 100 rpm,
releases (i) less than 10 wt % of the dose over an initial 2 hours of the in vitro dissolution test; (ii) at least 90 wt % of the dose over not less than an initial 8 hours of the in vitro dissolution test; (iii) no more than 30 wt % of the dose in any one hour during the in vitro dissolution test; and (iv) no more than 40 wt % of the dose in any consecutive two hours during the in vitro dissolution test.

2. The method of claim 1, wherein administration of the oral sustained release tablet to each patient achieves, across the patient population, a maximum average concentration of monomethyl fumarate in the blood plasma of the patients is less than 500 ng/ml.

3. A method of systemically administering a therapeutically effective amount of (N,N-diethylcarbamoyl)methyl methyl (2E)but-2-ene-1,4-dioate to treat a disease in each patient of a population of patients in need of such treatment, comprising administering an oral sustained release tablet consisting of (i) a core comprising (N,N-diethylcarbamoyl) methyl methyl (2E)but-2-ene-1,4-dioate and hydroxypropyl methylcellulose, wherein hydroxypropyl methylcellulose is from 8% to 10% by weight of the core and (ii) a compression-coated mantle layer comprising a sustained release polymer layer of hydroxypropyl methylcellulose surrounding the core, wherein the hydroxypropyl methylcellulose is from 30% to 32.5% by weight of the mantle, wherein the tablet does not contain an enteric coating, to each patient to achieve across the population an average maximum rate of rise in monomethyl fumarate concentration in the blood plasma of patients of less than 0.25% wt % ng-eq of monomethyl fumarate dosed/ml/hr,
wherein the disease is selected from multiple sclerosis and psoriasis; and
the tablet, when subjected to an in vitro dissolution test employing as a dissolution medium 750 mL of 0.1N hydrochloric acid, at pH 1.2, for a period of 2 hours, followed by addition of 250 mL of 200 mM tribasic sodium phosphate buffer resulting in an adjustment of the pH of the dissolution medium to 6.8, the dissolution medium being maintained at 37° C. and stirred at 100 rpm,
releases (i) less than 10 wt % of the dose over an initial 2 hours of the in vitro dissolution test; (ii) at least 90 wt % of the dose over not less than an initial 8 hours of the in vitro dissolution test; (iii) no more than 30 wt % of the dose in any one hour during the in vitro dissolution test; and (iv) no more than 40 wt % of the dose in any consecutive two hours during the in vitro dissolution test.

4. The method of claim 3, wherein the average maximum rate of rise in monomethyl fumarate concentration in the blood plasma of the patients is less than 0.20 wt % ng-eq of monomethyl fumarate dosed/ml/hr or is less than 0.15 wt % ng-eq of monomethyl fumarate dosed/ml/hr.

5. The method of claim 3, wherein the average maximum rate of rise in monomethyl fumarate concentration in the blood plasma of the patients is less than 0.10 wt % ng-eq of monomethyl fumarate dosed/mL/hr.

6. The method of claim 3, wherein administration of the oral sustained release tablet achieves, across the patient population, an average maximum rate of rise in monomethyl fumarate concentration of less than 500 ng/mL/hr.

7. The method of claim 3, wherein administration of the oral sustained release tablet achieves, across the patient population, an average maximum rate of rise in monomethyl fumarate concentration of less than 400 ng/mL/hr.

8. The method of claim 1, wherein incidence of flushing in the population of patients is reduced.

9. The method of claim 1 or claim 3, where dosing occurs at a frequency of not more than twice per day.

10. The method of claim 9, wherein the dosing frequency is twice per day.

11. The method of claim 9, wherein the dosing frequency is once per day.

12. The method of claim 1, wherein, administration of the tablet to each patient achieves, across the patient population, a maximum average concentration of monomethyl fumarate in the blood plasma of the patients is less than 400 ng/ml.

* * * * *